US010801052B2

(12) United States Patent
Vincent et al.

(10) Patent No.: US 10,801,052 B2
(45) Date of Patent: Oct. 13, 2020

(54) COFACTOR REGENERATION SYSTEM

(71) Applicants: OXFORD UNIVERSITY INNOVATION LIMITED, Oxford, Oxfordshire (GB); HUMBOLDT-UNIVERSITAT ZU BERLIN, Berlin (DE)

(72) Inventors: Kylie Vincent, Oxford (GB); Lars Lauterbach, Berlin (DE); Oliver Lenz, Berlin (DE)

(73) Assignees: OXFORD UNIVERSITY INNOVATION LIMITED, Oxford, Oxfordshire (GB); HUMBOLDT-UNIVERSITAT ZU BERLIN, Berlin (DE)

( * ) Notice: Subject to any disclaimer, the term of this patent is extended or adjusted under 35 U.S.C. 154(b) by 40 days.

(21) Appl. No.: 14/349,126

(22) PCT Filed: Oct. 3, 2012

(86) PCT No.: PCT/GB2012/052451
§ 371 (c)(1),
(2) Date: Apr. 2, 2014

(87) PCT Pub. No.: WO2013/050760
PCT Pub. Date: Apr. 11, 2013

(65) Prior Publication Data

US 2015/0044723 A1 Feb. 12, 2015

(30) Foreign Application Priority Data

Oct. 3, 2011 (GB) .................................. 1116971.1

(51) Int. Cl.
*C12P 19/36* (2006.01)
*C12N 9/02* (2006.01)

(52) U.S. Cl.
CPC ............ *C12P 19/36* (2013.01); *C12N 9/0036* (2013.01); *C12N 9/0051* (2013.01); *C12Y 106/99001* (2013.01); *C12Y 108/01004* (2013.01)

(58) Field of Classification Search
CPC ........................................................ C12P 19/36
USPC ........................................................ 435/68.1
See application file for complete search history.

(56) References Cited

U.S. PATENT DOCUMENTS 5,538,867 A 7/1996 Durliat et al.

FOREIGN PATENT DOCUMENTS

WO 2006/084276 A2 1/2000
WO WO 00/53731 A2 9/2000

OTHER PUBLICATIONS

Kohlmann et al, Electroenzymatic synthesis. Journal of Molecular Catalysis B: Enzymatic 51 (2008) 57-72.*

Tran-Betcke et al, Cloning and nucleotide sequences of the genes for the subunits of NAD-reducing hydrogenase of Alcaligenes eutrophus H16. J. Bacteriol. 172:2920-2929(1990).*

Menon et al, Cloning, sequencing, and mutational analysis of the hyb operon encoding *Escherichia coli* hydrogenase 2. J Bacteriol. Jul. 1994; 176(14): 4416-4423.*

Alcohol dehydrogenase from ExPASy. Downloaded Sep. 10, 2016.*

Merritt et al, Reversible Oxidation of Cyclic Secondary Alcohols by Liver Alcohol Dehydrogenase. J. Biol. Chem. 1959, 234:2778-2782.*

Vincent et al, Enzymatic catalysis on conducting graphite particles. Nat Chem Biol. Dec. 2007;3(12):761-2. Epub Nov. 11, 2007.*

Fumarate reductase IUBMB Enzyme Nomenclature. Downloaded Jun. 6, 2017.*

Portet et al, Effect of Carbon Particle Size on Electrochemical Performance of EDLC, Journal of The Electrochemical Soceity, 155 7 A531-A536 2008.*

Enzyme Classification database search results for "NADH: acceptor oxido-reductase". Downloaded Dec. 13, 2017.*

Laurinavichene et al, Effect of redox potential on activity of hydrogenase 1 and hydrogenase 2 in *Escherichia coli*.. Arch Microbiol (2002) 178 :437-442.*

Guo et al, Protein tolerance to random amino acid change. Proc Natl Acad Sci U S A. Jun. 22, 2004;101(25):9205-9210. Epub Jun. 14, 2004.*

Reeve et al, A modular system for regeneration of NAD cofactors using graphite particles modified with hydrogenase and diaphorase moieties.Chem. Commun., 2012, 48, 1589-1591.*

Search Report issued in British Application No. GB 1116971.1, dated Feb. 12, 2012.

J. Ratzka et al.: "Stabilisation of the soluble hydrogenase from Ralstonia eutropha H16 for application as a cofactor re-generation catalyst"; Book of Poster abstracts, XV. International Symposium on Relations between Homogeneous and Heterogeneous Catalysis, Berlin, Sep. 11-16, 2011, p. 16.

(Continued)

*Primary Examiner* — Sheridan Swope
(74) *Attorney, Agent, or Firm* — Merchant & Gould P.C.

(57) ABSTRACT

The present invention relates to cofactor regeneration systems, components and uses thereof and methods for generating and regenerating cofactors. The cofactor regeneration system comprises a first electron transfer component selected from a polypeptide comprising a NADH:acceptor oxido-reductase or NADPH:acceptor oxido-reductase, a second electron transfer component selected from a hydrogenase moiety and/or non-biological nanoparticles and an electronically conducting surface. The first and second electron transfer components are immobilised on the electrically conducting surface, and the first and second electron transfer components do not occur together in nature as an enzyme complex.

9 Claims, 7 Drawing Sheets

Figure 1:
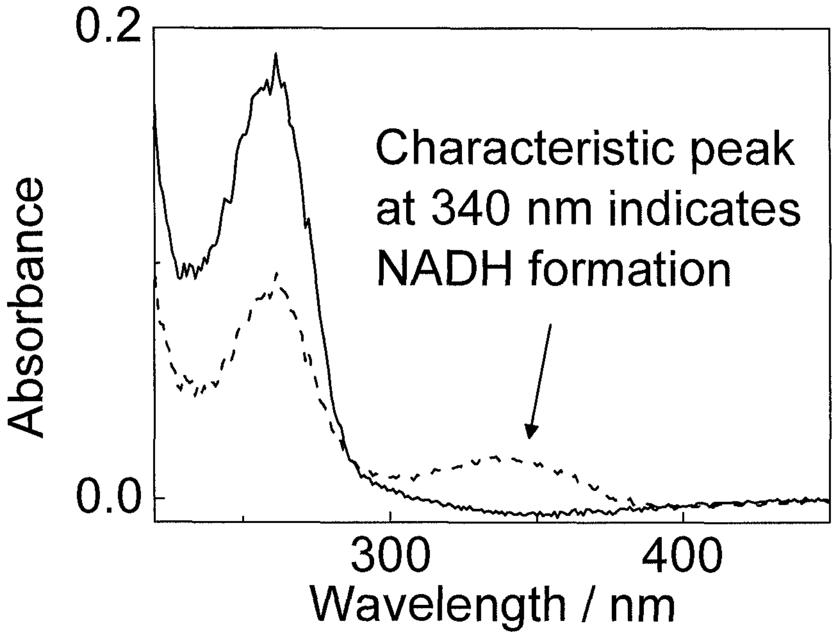

Specification includes a Sequence Listing.

(56) References Cited

OTHER PUBLICATIONS

M Zheng et al.: Effect of molecular mobility on coupled enzymatic reactions involving cofactor regeneration using nanoparticle-attached enzymes; Journal of Biotechnology, vol. 154, No. 4, Jul. 2011, pp. 274-280.

A Demir et al.: Selective oxidation and reduction reactions with cofactor regeneration medicated by galactitol-, lactate-, and formate dehydrogenases immobilized on magnetic nanoparticles; Journal of Biotechnology, vol. 152, No. 4, Apr. 2011, pp. 176-183.

I Okura et al.: "Regenerastion of NADH and Katone Hydrogenation by Hydrogen with the Combination of Hydrogenase and Alcohol Dehydrogenase"; Applied Biochemistry and Biotechnology, 1990, vol. 24-25, pp. 425-430.

Daniesson et al.: "Regeneration of NADH with Immobilized Systems of Alanine Dehydrogenase and Hydrogen Dehydrogenase"; Biotechnology Letters, 1982, vol. 4, No. 10, pp. 673-678.

B Payen et al.: "Use of Cytoplasmic Hydrogenase from Alcaligenes Eutrophus for NADH Regeneration"; Biotechnology Letters, 1983, vol. 5, No. 7, pp. 463-468.

JL Zhou et al.: "Progress of Electrochemical Biosensors Based on Nicotinamide Adenine Dinucleotide (phosphate)-Dependent Dehydrogenases"; Chinese Journal of Analytical Chemistry, 2009, vol. 37, No. 4, pp. 617-623.

Reeve et al.: "A modular system for regeneration of NAD cofactors using graphite particles modified with hydrogenase and diaphorase moieties"; CHemical Communications, 2012, vol. 48, pp. 1589-1591.

NAD-reducing hydrogenase hoxS subunit alpha, HoxF, Ralstonia eutropha, UNIPROT accession No. P22317, last modified Aug. 1, 1991.

Lauterbach et al. "Catalytic Properties of the Isolated Diaphorase Fragment of the NAD Reducing [NiFe]-Hydrogenase from Ralstonia eutropha." *PLoS One* 6(10):1-13 (2011).

Reeve et al. "A modular system for regeneration of NAD cofactors using graphite particles modified with hydrogenase and diaphorase moieties." *Chem. Commun.* 48:1589-1591 (2012).

Vincent et al. "Electrochemical Definitions of $O_2$ Sensitivity and Oxidative Inactivation in Hydrogenases." *JACS Articles.* 127:18179-18189 (2005).

International Search Report for corresponding international Patent Application No. PCT/GB2012/052451 dated Apr. 12, 2013.

Wichmann, R. et al. "Cofactor regeneration at the lab scale", Advances in Biochemical Engineering, Biotechnology, vol. 92, Jan. 1, 2005, pp. 225-260.

Kohlmann, et al. "Electroenzymatic synthesis", Journal of Molecular Catalysis. B., vol. 51, No. 3-4, Jan. 31, 2008, pp. 57-72.

Kashiwagi, Y. et al, "Preparative, electroenzymatic reduction of ketones on an all components-immobilized graphite felt electrode", Electrochimica ACTA, vol. 42, No. 13, Jan. 1. 1997, pp. 2267-2270.

Rundbäck, F. et al. "Coupling of permeabilized cells of *Gluconobacter oxydans* and *Ralstonia eutropha*for asymmetric ketone reduction using $H_2$ as reductant", Journal of Biotechnology, vol. 157, No. 1, Oct. 5, 2011, pp. 154-158.

Burgdorf et al., "The Soluble NAD-Reducing [NiFe]-Hydrogenase from Ralstonia eutropha H16 Consists of Six Subunits and Can Be Specifically Activated by NADPH.," Journal of Bacteriology, (May 2005), pp. 3122-3132.

Healy et al. "Electrically conducting particle networks in polymer electrolyte as three-dimensional electrodes for hydrogenase electrocatalysis," Electrochimica Acta, (2011), pp. 10786-10790.

Reeve et al. "Enzymes as modular catalysts for redox harl-reactions in H2-powered chemical synthesis: from biology to technology", Biochemical Journal 474: 215-230 (2017).

* cited by examiner (a)

(b)

COFACTOR REGENERATION SYSTEM

This application is a National Stage Application of PCT/GB2012/052451, filed 3 Oct. 2012, which claims benefit of Ser. No. 1116971.1, filed 3 Oct. 2011 in Great Britain and which applications are incorporated herein by reference. To the extent appropriate, a claim of priority is made to each of the above disclosed applications.

The work leading to this invention has received funding from the European Research Council under the European Union's Seventh Framework Programme (FP7/2007-2013)/ERC grant agreement No. 258600.10.

The present invention relates to a cofactor regeneration system, components and uses thereof, products comprising said cofactor regeneration system and components thereof, as well as methods for cofactor generation and regeneration.

Cofactors are non-protein chemical compounds that play an essential role in many enzyme catalysed biochemical reactions. Cofactors act to transfer chemical groups between enzymes. Nicotinamide adenine dinucleotide ($NAD^+$), and nicotinamide adenine dinucleotide phosphate ($NADP^+$) and the reduced forms of said molecules (NADH and NADPH, respectively) are biological cofactors which play a central role in the metabolism of cells acting as electron transfer agents. The oxidized forms $NAD^+$ and $NADP^+$ act as electron acceptors, becoming reduced in the process. NADH and NADPH, in turn, can act as reducing agents, becoming oxidized in the process.

Enzymes are commonly used as biocatalysts in the chemical and pharmaceutical industries. Redox enzymes—those that mediate oxidation or reduction reactions—form a significant subset of enzymes that are useful in industrial applications. However, most redox enzymes are dependent on expensive cofactors such as NADPH (approx. $500 for 0.75 g). To date, the use of NAD(P)H-dependent catalysts has been severely limited by the absence of industrially useful methods for recycling NAD(P)H. Currently, NADH is often regenerated using a formate dehydrogenase system. This process produces $CO_2$ which strongly affects the pH of the reaction solution. The formate dehydrogenase system is characterised by a low turnover frequency and a limited half-life. Also, formate (the substrate for cofactor regeneration) contaminates the product of the coupled enzyme reaction. NADPH is currently often regenerated using a glucose dehydrogenase system in which glucose and its oxidized form contaminate the product of the coupled enzyme system.

Electrochemical regeneration of cofactors at conventional electrodes requires a large overpotential (meaning loss of energy). Some modified electrodes have been reported, e.g. with poly(Neutral Red), but modifiers may be toxic or damaging to enzymes. Another major disadvantage is that bio-inactive forms (e.g. dimers) of $NAD^+$/NADH may be generated in the electrode reaction.

There is, therefore, a need to provide an alternative and/or improved cofactor regeneration system.

The present invention solves one or more of the above mentioned problems.

In one aspect, the invention provides a cofactor regeneration system comprising or consisting of:

i) a first electron transfer component selected from one or more polypeptides comprising a NADH:acceptor oxido-reductase or a NADPH:acceptor oxido-reductase, ii) a second electron transfer component selected from a hydrogenase moiety and/or non-biological nanoparticles; and, iii) an electronically conducting surface;

wherein the first and second electron transfer components are immobilised on the electrically conducting surface, and wherein the first and second electron transfer components do not occur together in nature as an enzyme complex.

The invention advantageously provides a highly efficient, rapid and/or robust cofactor regeneration system for biological cofactors. Said system provides a welcome replacement for the expensive and/or inefficient systems presently being used. As discussed above, extant methods of electrochemical cofactor regeneration require a fairly large overpotential (meaning loss of energy) to operate. The present invention advantageously utilizes catalysts that work at minimal, or undetectable, overpotential and is energetically efficient.

In addition, the invention advantageously provides a cofactor regeneration system which is modular in structure. Thus, the system can be tuned (by choice of different components of the system) for a specific application and/or condition(s). This provides a great deal of flexibility and allows optimization of the cofactor regeneration system depending on the application/conditions. For example, an oxygen ($O_2$)—tolerant hydrogenase may be selected as the second electron transfer component if the cofactor regeneration system is used to supply cofactors to enzymes requiring $O_2$, such as cytochrome P450 mono-oxygenases. In contrast, extant systems employing formate dehydrogenase (FDH) and/or glucose dehydrogenase (GDH) are limited to specific operating condition requirements (e.g. a narrow pH range).

Another advantage of the present invention is the ability to employ $H_2$ as the electron donor and/or $H^+$ as the electron sink. The system therefore does not require the addition of other soluble reagents or products, which are hard to separate after cofactor regeneration has taken place.

Examples of cofactors embraced by the present invention include nicotinamide adenine dinucleotide ($NAD^+$) and the reduced form of $NAD^+$, namely NADH, as well as nicotinamide adenine dinucleotide phosphate ($NADP^+$) and the reduced form of $NADP^+$, namely NADPH.

In one embodiment, said first electron transfer component comprises or consists of a NADH:acceptor oxido-reductase or NADPH:acceptor oxidoreductase. Said enzymes catalyze the oxidation of NADH and/or NADPH and/or the reduction of $NAD^+$ and/or $NADP^+$—the enzyme may act as an oxidizing agent or as a reducing agent, depending on the reaction conditions. By way of example, the ratio of $NAD^+$ to NADH and/or the ratio of $NADP^+$ to NADPH may influence the direction of the reaction i.e. whether the enzyme acts as a reducing agent or oxidizing agent. In one embodiment, the second electron transfer component comprises or consists of a hydrogenase in which case, the $H_2$ concentration may also influence the way the reaction proceeds. Suitable reaction conditions for regeneration of each of the above-mentioned cofactors are described below. Thus, in one embodiment, said NADH:acceptor oxido-reductase or NADPH:acceptor oxidoreductase may act as an oxidizing agent and/or a reducing agent.

In one embodiment, said NADH:acceptor oxido-reductase or NADPH:acceptor oxidoreductase comprises or consists of an amino acid sequence having at least 20% (such as at least 25%, 30%, 35%, 40%, 50%, 60%, 70%, 80%, 85%, 88%, 90% 92%, 94%, 96%, 98%, 99% or 100%) sequence identity to the amino acid sequence of *Ralstonia eutropha* diaphorase HoxF (SEQ ID NO: 1) and/or an amino acid sequence having at least 20% (such as at least 25%, 30%, 35%, 40%, 50%, 60%, 70%, 80%, 85%, 88%, 90% 92%, 94%, 96%, 98%, 99% or 100%) sequence identity to the amino acid sequence of *Ralstonia eutropha* diaphorase HoxU (SEQ ID NO: 2).

In one embodiment, said NADH:acceptor oxido-reductase or NADPH:acceptor oxidoreductase comprises or consists of an amino acid sequence having at least 20% (such as at least 25%, 30%, 35%, 40%, 50%, 60%, 70%, 80%, 85%, 88%, 90% 92%, 94%, 96%, 98%, 99% or 100%) sequence identity to the amino acid sequence of *Ralstonia eutropha* diaphorase HoxF (SEQ ID NO: 1) and/or an amino acid sequence having at least 20% (such as at least 25%, 30%, 35%, 40%, 50%, 60%, 70%, 80%, 85%, 88%, 90% 92%, 94%, 96%, 98%, 99% or 100%) sequence identity to the amino acid sequence of *Ralstonia eutropha* diaphorase HoxU (SEQ ID NO: 2) and/or an amino acid sequence having at least 20% (such as at least 25%, 30%, 35%, 40%, 50%, 60%, 70%, 80%, 85%, 88%, 90% 92%, 94%, 96%, 98%, 99% or 100%) sequence identity to the amino acid sequence of *Ralstonia eutropha* diaphorase HoxI (SEQ ID NO: 3).

In one embodiment, the NADH:acceptor oxido-reductase or NADPH:acceptor oxidoreductase may comprise or consist of flavoprotein (Fp) subcomplex of Complex I of *Bos taurus* (SEQ ID NO: 4 and/or SEQ ID NO: 5). Thus, in one embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the 51 kDa protein of *Bos taurus* Complex I (SEQ ID NO: 4) and/or an amino acid sequence having at least 70% (such as at least 75%, 80%, 85%, 90%, 95%, 96%, 98%, 99% or 100%) sequence identity to the amino acid sequence of the 24 kDa subcomplex of *Bos taurus* Complex I (SEQ ID NO: 5).

In another embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of *R. eutropha* $NAD^+$-dependent formate dehydrogenase diaphorase moiety FdsB (SEQ ID NO: 6) and/or an amino acid sequence having at least 70% (such as at least 75%, 80%, 85%, 90%, 95%, 96%, 98%, 99% or 100%) sequence identity to the amino acid sequence of the *R. eutropha* $NAD^+$-dependent formate dehydrogenase diaphorase moiety FdsG (SEQ ID NO: 7).

In another embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the NADPH oxidoreductase moiety from *Pyrococcus furiosus* soluble hydrogenase I gamma subunit (SEQ ID NO: 8) and/or an amino acid sequence having at least 70% (such as at least 75%, 80%, 85%, 90%, 95%, 96%, 98%, 99% or 100%) sequence identity to the amino acid sequence of the NADPH oxidoreductase moiety from *Pyrococcus furiosus* soluble hydrogenase 1 beta subunit (SEQ ID NO: 9).

In another embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the NADPH oxidoreductase moiety from *Pyrococcus furiosus* soluble hydrogenase II gamma subunit (SEQ ID NO: 10) and/or an amino acid sequence having at least 70% (such as at least 75%, 80%, 85%, 90%, 95%, 96%, 98%, 99% or 100%) sequence identity to the amino acid sequence of the NADPH oxidoreductase moiety from *Pyrococcus furiosus* soluble hydrogenase II beta subunit (SEQ ID NO: 11).

In one embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Rhodococcus opacus* soluble hydrogenase HoxF (SEQ ID NO: 12), and/or an amino acid sequence having at least 70% (such as at least 75%, 80%, 85%, 90%, 95%, 96%, 98%, 99% or 100%) sequence identity to the amino acid sequence of the diaphorase moiety of *Rhodococcus opacus* soluble hydrogenase HoxU (SEQ ID NO: 13).

In another embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Allochromatium vinosum* soluble hydrogenase HoxF (SEQ ID NO: 14), and/or an amino acid sequence having at least 70% (such as at least 75%, 80%, 85%, 90%, 95%, 96%, 98%, 99% or 100%) sequence identity to the amino acid sequence of the diaphorase moiety of *Allochromatium vinosum* soluble hydrogenase HoxU (SEQ ID NO: 15).

In another embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Thiocapsa roseopersicina* Hox1F (SEQ ID NO: 16), and/or an amino acid sequence having at least 70% (such as at least 75%, 80%, 85%, 90%, 95%, 96%, 98%, 99% or 100%) sequence identity to the amino acid sequence of the diaphorase moiety of *Thiocapsa roseopersicina* soluble hydrogenase Hox1U (SEQ ID NO: 17).

In one embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Thiocapsa roseopersicina* Hox2F (SEQ ID NO: 18), and/or an amino acid sequence having at least 70% (such as at least 75%, 80%, 85%, 90%, 95%, 96%, 98%, 99% or 100%) sequence identity to the amino acid sequence of the diaphorase moiety of *Thiocapsa roseopersicina* soluble hydrogenase Hox2U (SEQ ID NO: 19).

In another embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Synechocystis* sp. PCC 6803 HoxF (SEQ ID NO: 20), and/or an amino acid sequence having at least 70% (such as at least 75%, 80%, 85%, 90%, 95%, 96%, 98%, 99% or 100%) sequence identity to the amino acid sequence of the diaphorase moiety of *Synechocystis* sp. PCC 6803 HoxU (SEQ ID NO: 21).

In one embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Synechococcus elongates* PCC 6301 HoxF (SEQ ID NO: 22), and/or an amino acid sequence having at least 70% (such as at least 75%, 80%, 85%, 90%, 95%, 96%, 98%, 99% or 100%) sequence identity to the amino acid sequence of the diaphorase moiety of *Synechococcus elongates* PCC 6301 HoxU (SEQ ID NO: 23).

In one embodiment, said NADH:acceptor oxido-reductase or NADPH:acceptor oxidoreductase comprises or consists of an amino acid sequence having at least 70% (such as at least 75%, 80%, 85%, 90%, 95%, 96%, 98%, 99% or 100%) sequence identity to the amino acid sequence of the diaphorase moiety of *Rhodobacter capsulatus* SB1003 formate dehydrogenase beta subunit FdsB (SEQ ID NO: 66), and/or an amino acid sequence having at least 70% (such as at least 75%, 80%, 85%, 90%, 95%, 96%, 98%, 99% or 100%) sequence identity to the amino acid sequence of the diaphorase moiety of *Rhodobacter capsulatus* SB1003 formate dehydrogenase gamma subunit FdsG (SEQ ID NO: 67)

Conventional methods for determining amino acid sequence identity are discussed in more detail later in the specification.

In one embodiment, the cofactor regeneration system comprises one or more (such as two, three, four, five, six, seven, eight, nine, or ten or more) different NADH:acceptor oxido-reductase or NADPH:acceptor oxidoreductases. All of the above mentioned NADH:acceptor oxido-reductases or NADPH:acceptor oxidoreductases are suitable in this regard. Any combination of the above-mentioned NADH: acceptor oxido-reductases or NADPH:acceptor oxidoreductases may be employed in the first electron transfer component of the present invention.

The first electron transfer component of the present invention may comprise or consist of one or more (such as two, three, four, five, six, seven or more) polypeptides in addition to the NADH:acceptor oxido-reductase or NADPH:acceptor oxidoreductase. In one embodiment, the first electron transfer component further comprises or consists of a polypeptide having at least 70% (such as at least 75%, 80%, 85%, 90%, 95%, 96%, 98%, 99% or 100%) sequence identity to the amino acid sequence of *Ralstonia eutropha* soluble hydrogenase moiety HoxHY (SEQ ID NOs: 24 and/or 25). In one embodiment said HoxH sequence (SEQ ID NO: 24) is selected from *Ralstonia eutropha* soluble hydrogenase moiety variant HoxH_I64A (SEQ ID NO: 68). Said variant contains a substitution in the active site of the enzyme, which renders it non-functional. Without wishing to be bound by theory, the present inventors believe that the presence of a HoxHY component in the first electron transfer component increases the stability of the NADH:acceptor oxido-reductase or NADPH:acceptor oxidoreductase leading to increased efficiency/activity of the system. Additional methods for increasing the stability of proteins/protein complexes are known in the art, and may be routinely employed by a skilled person in connection with the present invention.

In one embodiment, the first electron transfer component of the present invention may comprise or consist of a HoxHYFU tetramer, such as the HoxHYFU tetramer of *Ralstonia eutropha* (i.e. SEQ ID NOs: 24, 25, 1, 2). Thus, in one embodiment, the first electron component of the present invention comprises or consists of an amino acid sequence having at least 70% (such as at least 75%, 80%, 85%, 90%, 95%, 96%, 98%, 99% or 100%) sequence identity to the amino acid sequence of a *Ralstonia eutropha* HoxHYFU tetramer (SEQ ID NOs: 24, 25, 1, 2).

The invention also provides for individual components, such as the first and second electron transfer components, and an electronically conducting surface for use in the cofactor regeneration system of the invention.

Thus, in one aspect, the invention provides a *Ralstonia eutropha* diaphorase variant, wherein said diaphorase variant comprises or consists of an amino acid sequence having at least 70% (such as at least 75%, 80%, 85%, 90%, 95%, 96%, 98%) and less than 100% (such as less than 99%, 98%, 97%, 96%, 95%, 90%, 85%, 80%, 75%) sequence identity to the amino acid sequence of *Ralstonia eutropha* diaphorase HoxF (SEQ ID NO: 1), and/or an amino acid sequence having at least 70% (such as at least 75%, 80%, 85%, 90%, 95%, 96%, 98%) and less than 100% (such as less than 99%, 98%, 97%, 96%, 95%, 90%, 85%, 80%, 75%) sequence identity to the amino acid sequence of *Ralstonia eutropha* diaphorase HoxU (SEQ ID NO: 2), and/or an amino acid sequence having at least 70% (such as at least 75%, 80%, 85%, 90%, 95%, 96%, 98%) and less than 100% (such as less than 99%, 98%, 97%, 96%, 95%, 90%, 85%, 80%, 75%) sequence identity to the amino acid sequence of *Ralstonia eutropha* diaphorase HoxI (SEQ ID NO: 3).

In one embodiment, the cofactor regeneration system of the present invention comprises the *Ralstonia eutropha* HoxF diaphorase variants described herein. In particular, the first electron transfer component of the cofactor regeneration system described herein embraces the diaphorase variants of the present invention.

In one embodiment, the diaphorase variant has an increased catalytic activity for $NAD^+$ and/or $NADP^+$ reduction and/or NADH and/or NADPH oxidation compared to *Ralstonia eutropha* diaphorase comprising or consisting of SEQ ID NO:1 and/or SEQ ID NO: 2 and/or SEQ ID NO: 3. In one embodiment, catalytic activity may embrace $K_M$ and/or $k_{cat}$. In one embodiment, increased catalytic activity embraces increased affinity, and/or reduction and/or oxidation capacity for $NAD^+$, $NADP^+$, NADH and/or NADPH.

In one embodiment, the diaphorase variant has an increased catalytic activity ($k_{cat}$ and/or $K_M$) for $NADP^+$ reduction and/or NADPH oxidation compared to *Ralstonia eutropha* diaphorase comprising or consisting of SEQ ID NO:1 and/or SEQ ID NO: 2 and/or SEQ ID NO: 3. In one embodiment, the catalytic activity of said diaphorase for $NADP^+$ and/or NADPH is increased by a factor of at least 5 (such as at least 5, 10, 20, 30, 40, 50, 100, 200, 300, 400, 600, 800, 1000, 5000, 10000 or 100000). In one embodiment, the catalytic activity of said diaphorase for $NADP^+$ and/or NADPH is increased by a factor of between 5-100000.

In one embodiment, the diaphorase variant has an increased catalytic activity ($k_{cat}$ and/or $K_M$) for $NAD^+$ reduction and/or NADH oxidation compared to *Ralstonia eutropha* diaphorase comprising or consisting of SEQ ID NO:1 and/or SEQ ID NO: 2 and/or SEQ ID NO: 3. In one embodiment, the catalytic activity of said diaphorase for $NAD^+$ and/or NADH is increased by a factor of at least 5 (such as at least 5, 10, 20, 30, 40, 50, 100, 200, 300, 400, 600, 800, 1000, 5000, 10000 or 100000). In one embodiment, the catalytic efficiency of said diaphorase for $NAD^+$ and/or NADH is increased by a factor of between 5-100000.

The Michaelis constant $K_M$ is a standard means of characterising an enzyme's affinity for a substrate. $K_M$ represents the concentration of substrate at which the enzyme has half of its maximum activity. In other words, a low $K_M$ indicates that the enzyme reaches half of its maximum activity at low levels of substrate. It is understood by those skilled in the art, that the $K_M$ value decreases as affinity increases. Thus, an increase in affinity is characterised by a decrease in the $K_M$ value. In one embodiment, the $K_M$ of said diaphorase variant for $NADP^+$ and/or $NAD^+$ and/or NADPH and/or NADH is reduced compared to the wild-type *Ralstonia eutropha* diaphorase comprising or consisting of SEQ ID NO:1 and/or SEQ ID NO: 2 and/or SEQ ID NO: 3.

Methods for measuring affinity ($K_M$) are routine to those skilled in the art. Briefly, affinity of the diaphorase for NADH and/or NADPH can be measured under anaerobic conditions at 30° C. in 50 mM Tris-HCl buffer, pH 8.0, containing 1 mM NADH or 1 mM NADPH, 5 mM benzyl viologen (oxidized), 90 μM dithionite, and 10 to 50 pmol of enzyme. The absorption is monitored spectrophotometrically at 578 nm ($\varepsilon$=8.9 $mM^{-1}$ $cm^{-1}$ for benzyl viologen). Individual data points of the activity measurements are used for the determination of $K_M$ by non linear regression. An electrochemical method can be used to determine $K_M$. Briefly, the diaphorase moiety is adsorbed onto a pyrolytic graphite electrode which is immersed in an electrochemical cell solution containing buffered electrolyte (eg 50 mM phosphate at pH 7.0). The electrode is held at a constant potential of −412 mV while the concentration of $NAD^+$ or $NADP^+$ is increased by injections into the solution. Since the electrocatalytic current magnitude recorded at the electrode is directly proportional to catalytic activity of the immobilised enzyme film, a plot of (substrate concentration)/(current magnitude) vs (substrate concentration) is analogous to a Hanes or Woolf plot of (substrate concentration)/(activity) vs (substrate concentration), and the intercept on the (substrate concentration) axis is equal to ($-K_M$). $k_{cat}$ is the catalytic conversion of product under optimum conditions with substrate saturated enzyme. [L. Lauterbach, Z. Idris, K. A. Vincent, O. Lenz "Catalytic properties of the isolated diaphorase fragment of the $NAD^+$-reducing [NiFe]-hydrogenase from *Ralstonia eutropha*" PLoS ONE doi:10.1371/journal.pone.0025939.]

An improved affinity (lower $K_M$) of the diaphorase variant for NADPH and/or $NADP^+$ indicates an improved catalytic activity for oxidation/reduction of NADPH/$NADP^+$. Thus, in one embodiment, reference herein to increased or improved affinity also embraces an increased or improved oxidation/reduction activity. Thus, in one embodiment the diaphorase variant has an increased and/or improved oxidation/reduction activity when compared to wild-type *Ralstonia eutropha* diaphorase comprising or consisting of SEQ ID NO:1 and/or SEQ ID NO: 2 and/or SEQ ID NO:3.

The turnover number $k_{cat}$ gives a measure of the number of substrate molecules turned over per enzyme moiety per second. An improved turnover number $k_{cat}$ of the diaphorase variants for $NADP^+$ and/or $NAD^+$ and/or NADPH and/or NADH indicates an increased frequency for oxidation of NADPH and/or NADH and/or reduction of $NAD^+$ and/or $NADP^+$. In one embodiment, the diaphorase variant has an increased turnover number ($k_{cat}$) for $NAD^+$, $NADP^+$, NADH and/or NADPH compared to *Ralstonia eutropha* diaphorase comprising or consisting of SEQ ID NO:1 and/or SEQ ID NO: 2 and/or SEQ ID NO:3.

An improved turnover number ($k_{cat}$) of the diaphorase variant for NADPH and/or $NADP^+$ indicates an improved catalytic activity for oxidation/reduction of NADPH/$NADP^+$. Thus, in one embodiment, reference herein to increased turnover number $k_{cat}$ also embraces an increased or improved oxidation/reduction capacity. Thus, in one embodiment the diaphorase variant has an increased and/or improved oxidation/reduction capacity when compared to wild-type *Ralstonia eutropha* diaphorase comprising or consisting of SEQ ID NO:1 and/or SEQ ID NO: 2 and/or SEQ ID NO:3.

An improved turnover number ($k_{cat}$) of the diaphorase variant for NADH and/or $NAD^+$ indicates an improved catalytic activity for oxidation/reduction of NADH/$NAD^+$. Thus, in one embodiment, reference herein to increased turnover number $k_{cat}$ also embraces an increased or improved oxidation/reduction capacity. Thus, in one embodiment the diaphorase variant has an increased and/or improved oxidation/20 reduction capacity when compared to wild-type *Ralstonia eutropha* diaphorase comprising or consisting of SEQ ID NO:1 and/or SEQ ID NO: 2 and/or SEQ ID NO:3.

In one embodiment, said diaphorase variant comprises or consists of an amino acid sequence having at least 70% (such as at least 75%, 80%, 85%, 90%, 95%, 96%, 98%, 99% or 100%) sequence identity to the amino acid sequence selected from the group consisting of SEQ ID NOs: 54-65== and/or an amino acid having at least 70% (such as at least 75%, 80%, 85%, 90%, 95%, 96%, 98%, 99%, 100%) sequence identity to the amino acid sequence of *Ralstonia eutropha* diaphorase HoxU (SEQ ID NO: 2), and/or an amino acid having at least 70% (such as at least 75%, 80%, 85%, 90%, 95%, 96%, 98%, 99%, 100%) sequence identity to the amino acid sequence of *Ralstonia eutropha* diaphorase HoxI (SEQ ID NO: 3).

In one embodiment, said diaphorase variant comprises or consists of an amino acid sequence which differs from the amino acid sequence of SEQ ID NO:1 at position 326 by having an amino acid selected from the group consisting of K (lysine), S (serine), A (alanine), N (asparagine), R (arginine) or H (histidine). In one embodiment, the amino acid is K (lysine), and this diaphorase variant corresponds to SEQ ID NO: 54.

In another embodiment, said diaphorase variant comprises or consists of an amino acid sequence which differs from the amino acid sequence of SEQ ID NO:1 at position 401 by having an amino acid selected from the group consisting of K (lysine), S (serine), A (alanine), N (asparagine) R (arginine) or H (histidine). In one embodiment, the amino acid is K (lysine), and this diaphorase variant corresponds to SEQ ID NO: 55.

In another embodiment, said diaphorase variant comprises or consists of an amino acid sequence which differs from the amino acid sequence of SEQ ID NO:1 at position 467 by having an amino acid selected from the group consisting of S (serine), K (lysine), A (alanine), N (asparagine), R (arginine) or H (histidine). In one embodiment, the amino acid is S (serine), and this diaphorase variant corresponds to SEQ ID NO: 56.

In another embodiment, said diaphorase variant comprises or consists of an amino acid sequence which differs from the amino acid sequence of SEQ ID NO:1 at position 340 by having an amino acid selected from the group consisting of A (alanine), K (lysine), S (serine), N (asparagine), R (arginine) or H (histidine). In one embodiment, the amino acid is A (alanine), and this diaphorase variant corresponds to SEQ ID NO: 57.

In another embodiment, said diaphorase variant comprises or consists of an amino acid sequence which differs from the amino acid sequence of SEQ ID NO:1 at position 341 by having an amino acid selected from the group consisting of A (alanine), K (lysine), S (serine), N (asparagine), R (arginine) or H (histidine). In one embodiment, the amino acid is A (alanine), and this diaphorase variant corresponds to SEQ ID NO: 58. In another embodiment, the amino acid is H (histidine), and this diaphorase variant corresponds to SEQ ID NO: 65.

In one embodiment, the diaphorase variant of the present invention comprises or consists of an amino acid sequence which differs from the amino acid sequence of SEQ ID NO:1 at one or more (such as 2, 3, 4, 5, or 6) amino acid positions. In other words, said amino acid sequence may have mutations (e.g. substitutions and/or deletions), such as one or more (such as 2, 3, 4, 5, or 6) of the above-mentioned amino acid mutations.

By way of example, SEQ ID NO 59 differs from the amino acid sequence of SEQ ID NO:1 at positions 340 and 341 by having A (alanine) amino acid substitutions at said positions. SEQ ID NO 60 has amino acid substitutions at positions 340 (alanine) and 401 (lysine). SEQ ID NO 61 has amino acid substitutions at positions 326 (lysine) and 401 (lysine). SEQ ID NO 62 has amino acid substitutions at positions 467 (serine) and 401 (lysine). SEQ ID NO 63 has amino acid substitutions at positions 340 (asparagine) and 467 (serine). SEQ ID NO 64 has amino acid substitutions at positions 341 (alanine) and 467 (serine).

The above-mentioned variants advantageously have a greater affinity and/or turnover number for $NADP^+$/NADPH and therefore have an improved $NADP^+$/NADPH catalytic activity compared to *Ralstonia eutropha* diaphorase HoxF and/or HoxU and/or HoxI (SEQ ID NO: 1 and/or SEQ ID NO:2 and/or SEQ ID NO:3). Other diaphorase variants embraced by the present invention include variants comprising amino acid substitutions and/or deletions which serve to decrease the negative charges surrounding the active site and/or increase the positive charges surrounding the active site. Without wishing to be bound by theory, the Inventors believe that such variants advantageously are able to accommodate the additional negatively charged phosphate group of $NADP^+$ resulting in an improvement in affinity and/or oxidation and/or reduction capacity of the diaphorase variant compared to the wild-type diaphorase.

In one embodiment, the second electron transfer component of the cofactor regeneration system of the present invention comprises or consists of a hydrogenase moiety, wherein said hydrogenase moiety comprises or consists of an amino acid sequence having at least 70% (such as at least 75%, 80%, 85%, 90%, 95%, 96%, 98%, 99% or 100%) sequence identity to the amino acid sequence of *Ralstonia eutropha* soluble hydrogenase moiety (SEQ ID NOs: 24 and/or 25).

In one embodiment, the second electron transfer component of the cofactor regeneration system of the present invention comprises or consists of a hydrogenase moiety, wherein said hydrogenase moiety comprises or consists of an amino acid sequence having at least 70% (such as at least 75%, 80%, 85%, 90%, 95%, 96%, 98%, 99% or 100%) sequence identity to the amino acid sequence of *Ralstonia eutropha* membrane-bound hydrogenase moiety (SEQ ID NOs: 26 and/or 27 and/or 28).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Ralstonia eutropha* regulatory hydrogenase moiety (SEQ ID NOs: 29, and/or 30).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Escherichia coli* hydrogenase 1 (SEQ ID NOs: 31 and/or 32).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Escherichia coli* hydrogenase 2 (SEQ ID NOs: 33 and/or 34).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Aquifex aeolicus* hydrogenase 1 (SEQ ID NO:35 and/or 36).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Hydrogenovibrio marinus* hydrogenase (SEQ ID NOs: 37 and/or 38).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Thiocapsa roseopersicina* hydrogenase (SEQ ID NOs: 39 and 40).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Alteromonas macleodii* hydrogenase (SEQ ID NOs:41 and/or 42).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Rhodococcus opacus* soluble hydrogenase moiety (SEQ ID NOs: 43 and/or 44).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Allochromatium vinosum* membrane bound hydrogenase (SEQ ID NOs: 45 and/or 46).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Desulfovibrio fructosovorans* membrane bound hydrogenase (SEQ ID NOs: 47 and/or 48).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Clostridium pasteurianum* iron-iron hydrogenase (SEQ ID NOs: 49).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Clostridium acetobutylicum* iron-iron hydrogenase (SEQ ID NOs: 50).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Chlamydomonas reinhardtii* iron-iron hydrogenase (SEQ ID NOs: 51).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Desulfomicrobium baculatum* nickel-iron selenium hydrogenase (SEQ ID NOs: 52 and/or 53).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Desulfovibrio vulgaris* Nickel Iron hydrogenase pdb 1H2A (SEQ ID NOs: 69 and/or 70).

In another embodiment, said hydrogenase moiety may comprise or consist of an amino acid sequence having at least 70% (such as at least 75%, 80%, 85%, 90%, 95%, 96%, 98%, 99% or 100%) sequence identity to the amino acid sequence of *Desulfovibrio gigas* Periplasmic [NiFe] hydrogenase (SEQ ID NOs: 71 and/or 72).

In one embodiment of the present invention, the second electron transfer component is a hydrogenase moiety, wherein said hydrogenase moiety does not comprise (or lacks) a flavin mononucleotide (FMN) prosthetic group and/or a flavin adenine dinucleotide (FAD) prosthetic group. In one embodiment of the present invention, the hydrogenase moiety which does not comprise (or lacks) a FMN group and/or FAD group has increased stability compared to a hydrogenase comprising a FMN and/or a FAD group. Accordingly, use of such a hydrogenase (i.e. lacking a FMN and/or FAD prosthetic group) as the second electron transfer component in a cofactor regeneration system of the present invention may be advantageous because it increases the robustness/stability of the overall system. Examples of hydrogenases lacking a FMN prosthetic group include *Ralstonia eutropha* membrane-bound hydrogenase (SEQ ID NOs: 26-28), *Ralstonia eutropha* regulatory hydrogenase (SEQ ID NOs:29-30), *Escherichia coli* hydrogenase 1 (SEQ ID NOs:31-32), *Escherichia coli* hydrogenase 2 (SEQ ID NOs:33-34), *Aquifex aeolicus* hydrogenase 1 (SEQ ID NOs: 35-36), *Hydrogenovibrio marinus* membrane-bound hydrogenase (SEQ ID NOs: 37-38), *Desulfovibrio vulgaris* Nickel Iron hydrogenase (SEQ ID NOs: 69-70) and *Desulfovibrio gigas* Periplasmic [NiFe] hydrogenase (SEQ ID NOs:71-72).

In one embodiment, the second electron transfer component comprises or consists of non-biological nanoparticles. Suitable non-biological nanoparticles include metal nanoparticles (such as platinum or palladium nanoparticles), or nanoparticles of a metal oxide, or nanoparticles of a metal sulphide (such as molybdenum disulfide). The non-biological nanoparticles of the present invention are able to catalyse the interconversion of $H^+$ and $H_2$ close to the thermodynamic potential of the $2H^+/H_2$ couple under the experimental conditions. For example, the $2H^+/H_2$ couple potential is −0.413 V at 25° C., pH 7.0 and 1 bar $H_2$. In one embodiment, the second electron transfer component (i.e. the non-biological nanoparticles and/or the hydrogenase) operates in H2 oxidation at less than 100 mV more positive than the $2H^+/H_2$ couple potential, and/or operates in H+ reduction at less than 100 mV more negative than the $2H^+/H_2$ couple potential. Methods for determining overpotential are routine to those skilled in the art. Briefly, the catalyst (hydrogenase or non-biological nanoparticle) is attached to an electrode such that the catalyst can exchange electrons directly with the electrode. The electrode is immersed in an electrochemical cell solution containing buffered electrolyte (for example 50 mM phosphate at pH 7.0) saturated with $H_2$ (ie in equilibrium with a gas atmosphere comprising 100% $H_2$) and the electrode potential is cycled between lower and upper limiting potentials, eg −0.6 V vs the standard hydrogen electrode (SHE) and 0.2 V vs SHE. A catalyst which operates at minimal overpotential shows an electrocatalytic $H^+$ reduction current and/or an electrocatalytic $H_2$ oxidation current close to (ie within 100 mV below or above) the thermodynamic potential of the $2H^+/H_2$ couple under the experimental conditions. For example, the $2H^+/H_2$ couple potential is −0.413 V at 25° C., pH 7.0 and 1 bar $H_2$ or −0.36 V at 30° C., pH 6.0 and 1 bar $H_2$. Reference: Vincent, K. A., Parkin, A., Lenz, O., Albracht, S. P. J., Fontecilla-Camps, J. C., Cammack, R., Friedrich, B., Armstrong, F. A., 'Electrochemical Definitions of $O_2$ Sensitivity and Oxidative Inactivation in Hydrogenases' *Journal of the American Chemical Society* (2005) 127, 18179-18189.

In one embodiment of the present invention, the first and second electron transfer components do not occur together in nature as an enzyme complex. In other words, the first and second transfer components are not naturally associated with each other, and said first and second electron transfer components do not transfer electrons to and/or accept electrons from each other in the "natural" cellular environment. First and second electron transfer components of the present invention are therefore selected from components which do not occur together in a wild-type enzyme complex.

Thus, by way of example, the first and second electron transfer components may be selected from (or derived from) different bacterial species or from different bacterial genera. In another embodiment, the first and second electron transfer components may be selected from (or derived from) the same bacterial genus or species, but said first and second electron transfer components are selected from (or derived from) different enzymes. Taking *Ralstonia eutropha* as an example, the first electron transfer component may comprise the diaphorase HoxF and/or HoxU, and/or HoxH and/or HoxY and/or HoxI (SEQ ID NOs: 1 and/or 2, 24, 25 and/or 3). In this scenario, the second electron transfer component may comprise any suitable hydrogenase moiety such as the membrane bound hydrogenase moiety HoxGKZ (SEQ ID NOs: 26-28), or the regulatory hydrogenase moiety HoxBC (SEQ ID NOs: 29-30), but may not comprise the soluble hydrogenase moiety HoxHY (SEQ ID NOs: 24-25), which is normally associated with the diaphorase HoxFU. Thus, the individual components of the cofactor regeneration system can be tuned (by choice of different components of the system) for a specific application and/or condition(s). The Inventors have realized that by selecting components which are not naturally associated with each other in nature allows optimization of the cofactor regeneration system depending on the application/conditions. For example, an oxygen ($O_2$)-tolerant hydrogenase may be selected as the second electron transfer component if the cofactor regeneration system is used to supply cofactors to enzymes requiring $O_2$, such as cytochrome P450 monoxygenases.

In another aspect the invention provides a cofactor regeneration system comprising or consisting of:

i) a first electron transfer component selected from a polypeptide comprising a diaphorase variant as described herein, and ii) a second electron transfer component selected from a hydrogenase moiety and/or non-biological nanoparticles, and iii) an electronically conducting surface;

wherein the first and second electron transfer components are immobilised on the electrically conducting surface.

Suitable second electron transfer components i.e. hydrogenase moieties and non-biological particles are described above, and may be used in the present aspect of the invention.

As described herein, the cofactor regeneration system of the present invention may comprise an electronically conducting surface wherein the first and second electron transfer components are immobilised on the electronically conducting surface. In one embodiment, the term "immobilised" embraces adsorption, entrapment and/or cross-linkage. Adsorption generally relies on a non-covalent interaction. Thus, in one embodiment, the term "immobilised" refers to a non-covalent attachment. In another embodiment, the first and second electron transfer components are covalently bonded to the electronically conducting surface. Such an interaction may be referred to as "cross-linked" attachment. Entrapment refers to the first and second electron transfer components being trapped within the electronically conducting surface (e.g. because the electronically conducting surface is porous). Thus, in one embodiment, the term "immobilised" refers to entrapment. Entrapment may embrace non-covalent and/or covalent attachment. A combination of the above mentioned immobilisation means may also be used. In one embodiment, the electronically conducting surface of the present invention serves to transfer electrons between said first and second electron transfer components of the cofactor regeneration system.

In one embodiment, the electronically conducting surface of the cofactor regeneration system comprises or consists a carbon material, such as graphite particles, carbon nanotubes, carbon black, activated carbon, carbon nanopowder vitreous carbon (glassy carbon), carbon fibres, carbon cloth, carbon felt, carbon paper, graphene, glassy carbon, highly ordered pyrolytic graphite or edge oriented pyrolytic graphite;

Other suitable electronically conducting surface materials may comprise or consist of gold, silver, tungsten, iridium, metal oxide nanoparticles such as titanium oxide, indium oxide, tin oxide, indium tin oxide, and metal sulphide nanoparticles such as (boron) doped diamond. Electronically conducting surfaces combining one or more of the abovementioned materials are also embraced by the present invention.

In one embodiment of the present invention, the cofactor regeneration system advantageously comprises or consists of particles (e.g. beads) which can easily be removed from a reaction mixture, for example by sedimentation, filtration and/or centrifugation. The cofactor regeneration system comprising said particles can therefore advantageously be readily separated from a reaction mixture (e.g. by sedimentation, filtration and/or centrifugation) and re-used. In another embodiment, if the electronically conducting surface utilised is carbon cloth, carbon felt, carbon paper, (or similar material) for example, then the cofactor regeneration system can be readily separated from a reaction mixture by simply removing said carbon cloth/felt or paper from said reaction mixture.

In one embodiment, the term 'electronically conducting surface' of the present invention embraces one or more electronically conducting surfaces (e.g. a carbon material as described herein) connected/coupled via an electronically conducting linker (e.g. a wire). By way of example, two carbon particles may be connected via said electronically conducting linker, with the first and second electron transfer components of the present invention immobilised on said carbon particles. The electronically conducting linker may be made from one of the non-carbon materials described herein (e.g. gold, silver, tungsten, iridium etc) or another metal such as copper or aluminium. In one embodiment, the first electron transfer component of the present invention is immobilised to an electronically conducting carbon surface and the second electron transfer component is attached to a second electronically conducting carbon surface, wherein said carbon surfaces are connected via an electronically conducting linker. In other words, the electronically conducting surface of the present invention embraces one or more electronically conducting surfaces (e.g. a carbon material as described herein) coupled/connected/inter-linked by an electronically conducting linker (e.g. a wire made of gold, silver, tungsten, iridium) or another metal such as copper or aluminium.

In one embodiment, the cofactor regeneration system of the present invention further comprises or consists of one or more cofactors selected from $NAD^+$, NADH, $NADP^+$ and/or NADPH.

In use, electrons flow between the first and second electron transfer components of the cofactor regeneration system of the present invention. In one embodiment, electrons flow from the first electron transfer component to the second transfer component. Alternatively, electrons may flow from the second transfer component to the first electron transfer component. In use, the flow of electrons may be reversed, depending on reaction conditions. In use, electrons may flow directly between the first and second electron transfer components or indirectly via the electronically conducting surface of the present invention.

In one embodiment, the cofactor regeneration system of the present invention further comprises an oxidoreductase selected from a dehydrogenase, reductase, oxidase, synthase, transhydrogenase, dioxygenase, mono-oxygenase cytochrome p450 monooxygenase and/or ene reductase. Variants, derivatives and functional fragments of the aforementioned oxidoreductases are also embraced by the present invention. In one embodiment, the cofactor regeneration system of the present invention further comprises a variant of the aforementioned oxidoreductases, wherein said variant retains at least some of the activity/functionality of the native/wild-type enzyme. In one embodiment, the variant oxidoreductase has increased/improved activity/functionality when compared to the native/wild-type enzyme.

In one embodiment said oxidoreductase selected from a dehydrogenase, reductase, oxidase, synthase, transhydrogenase, dioxygenase, mono-oxygenase, cytochrome p450 monooxygenase and/or ene reductase is immobilised on said electronically conducting surface. Suitable immobilisation methods are described above. Alternatively, the aforementioned oxidoreductases may be immobilised on a separate/distinct electronically conducting surface from the first and second electron transfer components of the cofactor regeneration system. In another embodiment, said oxidoreductases selected from a dehydrogenase, reductase, oxidase, synthase, transhydrogenase, dioxygenase, mono-oxygenase, cytochrome p450 monooxygenase and/or ene reductase are not immobilised, but are present in a solution containing the cofactor regeneration system of the present invention. This approach would be particularly suited to those proteins/protein complexes which cannot be readily be immobilised. By way of example, multi-redox component cytochrome P450 mono-oxygenases or dioxygenases may be provided in a solution with the cofactor regeneration system of the present invention.

In one aspect, the present invention provides a cofactor regeneration system and components thereof (as defined above) for use in a method for generating a cofactor.

In another aspect, the present invention provides a cofactor regeneration system and components thereof (as defined above) for use in a method for regenerating a cofactor.

Thus, in one aspect the invention provides a method for (re)generating a cofactor comprising or consisting of adding to the cofactor regeneration system described herein, a cofactor selected from $NAD^+$, NADH, $NADP^+$ and/or NADPH.

In one embodiment, the NADH, NAD, NADPH or NADP added is present at a concentration of 1 μM to 1M (such as 1 μM to 800 mM, 1 μM to 600 mM, 1 μM to 400 mM, 1 μM to 200 mM, 1 μM to 100 mM, 1 μM to 10 mM, or 1 μM to 1 mM). In another embodiment, the NADH, NAD, NADPH or NADP added is present at a concentration of 1 μM to 10 mM (such as 5 μM to 10 mM, 10 μM to 10 mM, 25 μM to 10 mM, 50 μM to 10 mM, 100 μM to 10 mM, 250 μM to 10 mM, 500 μM to 10 mM or 1 mM to 10 mM). In one embodiment, the NADH, NAD, NADPH or NADP added is present at a concentration of 0.2 mM or 1-2 mM.

In one embodiment, the invention provides a method for (re)generating $NAD^+$ comprising or consisting of: adding to the cofactor regeneration system described herein, NADH and a gas atmosphere comprising an inert gas. The NADH added may be present at a concentration of 1 μM to 1M (such as 1 μM to 800 mM, 1 μM to 600 mM, 1 μM to 400 mM, 1 μM to 200 mM, 1 μM to 100 mM, 1 μM to 10 mM, or 1 μM to 1 mM) or 1 μM to 10 mM (such as 5 μM to 10 mM, 10 μM to 10 mM, 25 μM to 10 mM, 50 μM to 10 mM, 100 μM to 10 mM, 250 μM to 10 mM, 500 μM to 10 mM or 1 mM to 10 mM). The inert gas may be selected, for example, from $N_2$ or Argon (Ar). In one embodiment the inert gas is present at a concentration of 80-100% (i.e. the gas is present in the headspace of a suitable container comprising the cofactor regeneration system)

In another embodiment, the invention provides a method for (re)generating NADH comprising or consisting of: adding to the cofactor regeneration system described herein, $NAD^+$ and a gas atmosphere comprising H2 and O2. The $NAD^+$ added may be present at a concentration of 1 μM to 1M (such as 1 μM to 800 mM, 1 μM to 600 mM, 1 μM to 400 mM, 1 μM to 200 mM, 1 μM to 100 mM, 1 μM to 10 mM, or 1 μM to 1 mM) or 1 μM to 10 mM (such as 5 μM to 10 mM, 10 μM to 10 mM, 25 μM to 10 mM, 50 μM to 10 mM, 100 μM to 10 mM, 250 μM to 10 mM, 500 μM to 10 mM or 1 mM to 10 mM). In one embodiment, the $H_2$ is present at a concentration of 1-100%, with the remaining gas comprising an inert gas. In one embodiment, the $H_2$ is present at a concentration of 80-100% and the $O_2$ is present at a concentration of 0-20% (i.e. the gas is present in the headspace of a suitable container comprising the cofactor regeneration system). In another embodiment, the $H_2$ is present at a concentration of 1-4% and the $O_2$ is present at a concentration of 96-99% (i.e. the gas is present in the headspace of a suitable container comprising the cofactor regeneration system). In one embodiment, the $H_2$ is present at a concentration of 1-4% in air, or at a concentration of 70-99% in air.

In another embodiment, the invention provides a method for (re)generating NADP comprising or consisting of: adding to the cofactor regeneration system described herein, NADPH and a gas atmosphere comprising an inert gas. The NADPH added may be present at a concentration of 1 μM to 1M (such as 1 μM to 800 mM, 1 μM to 600 mM, 1 μM to 400 mM, 1 μM to 200 mM, 1 μM to 100 mM, 1 μM to 10 mM, or 1 μM to 1 mM) or 1 μM to 10 mM (such as 5 μM to 10 mM, 10 μM to 10 mM, 25 μM to 10 mM, 50 μM to 10 mM, 100 μM to 10 mM, 250 μM to 10 mM, 500 μM to 10 mM or 1 mM to 10 mM). The inert gas may be selected, for example, from $N_2$ or Argon (Ar). In one embodiment the inert gas is present at a concentration of 80-100% (i.e. the gas is present in the headspace of a suitable container comprising the cofactor regeneration system).

In another embodiment, the invention provides a method for (re)generating NADPH comprising or consisting of: adding to the cofactor regeneration system described herein, $NADP^+$ and a gas atmosphere comprising $H_2$. The $NADP^+$ added may be present at a concentration of 1 μM to 1M (such as 1 μM to 800 mM, 1 μM to 600 mM, 1 μM to 400 mM, 1 μM to 200 mM, 1 μM to 100 mM, 1 μM to 10 mM, or 1 μM to 1 mM) or 1 μM to 10 mM (such as 5 μM to 10 mM, 10 μM to 10 mM, 25 μM to 10 mM, 50 μM to 10 mM, 100 μM to 10 mM, 250 μM to 10 mM, 500 μM to 10 mM or 1 mM to 10 mM)). In one embodiment, the $H_2$ is present at a concentration of 1-100% (i.e. the gas is present in the headspace of a suitable container comprising the cofactor regeneration system). In one embodiment, the $H_2$ is present at a concentration of 80-100%. In one embodiment, the $H_2$ is present at less than 3%, such as 2% or 1%.

Other inert gases suitable for use in the methods of the present invention include Helium (He), Neon (Ne), Krypton (Kr), Xenon (Xe), Radon (Rn) and/or Sulfur hexafluoride ($SF_6$). In one embodiment, the gas phase in contact with the cofactor regeneration system of the present invention comprises or consists of one or more gases that are not considered inert gases. Examples of such 'non-inert' gases include ammonia ($NH_3$), carbon dioxide ($CO_2$), and/or hydrogen sulphide ($H_2S$).

In one embodiment, the methods described herein further comprises or consists of harvesting the (re)generated cofactor by removing the cofactor regeneration particles by filtration or by centrifugation, or by allowing the particles to settle and decanting off the solution (i.e. sedimentation). Filtration methods are known to those skilled in the art, and any such method may be used. By way of example, a simple filter paper may be used to remove the cofactor regeneration particles.

In another aspect, the invention provides use of a cofactor regeneration system as described herein, or a diaphorase variant for use in a cofactor regeneration system of the present invention, for generating a cofactor.

In another aspect, the invention provides use of a cofactor regeneration system as described herein, or a diaphorase variant for use in a cofactor regeneration system of the present invention, for regenerating a cofactor.

In one embodiment, the invention provides use of a cofactor regeneration system or use of a diaphorase variant, as described herein, in a synthetic reaction. In one embodiment the synthetic reaction is an enzyme-catalyzed synthetic reaction. Suitable applications for the cofactor regeneration system of the present invention include synthetic processes wherein cofactor-dependent oxidoreductases are used as catalysts.

In another aspect, the invention provides a synthetic reaction comprising or consisting of the cofactor regeneration system as described herein, or the diaphorase variant as described herein.

In one embodiment, the synthetic reaction further comprises an oxidoreductase which is dependent on NAD+, NADH, NADP+ and/or NADPH. Examples of oxidoreductases include dehydrogenase, reductase, oxidase, synthase, transhydrogenase, dioxygenase, mono-oxygenase, cytochrome p450 monooxygenase and/or ene reductase.

In one embodiment, said oxidoreductase is immobilised on the electronically conducting surface of the present invention along with the first and second electron transfer components of the cofactor regeneration system of the present invention. Suitable methods for immobilisation have been described elsewhere in the present specification and apply equally hereto. Thus, immobilisation embraces covalent and non-covalent attachments including adsorption, entrapment and/or cross-linkage. Alternatively, the aforementioned oxidoreductases may be immobilised on a separate/distinct electronically conducting surface from the first and second electron transfer components of the cofactor regeneration system. In another embodiment, said oxidoreductases selected from a dehydrogenase, reductase, oxidase, synthase, transhydrogenase, dioxygenase, monooxygenase, cytochrome p450 monooxygenase and/or ene reductase are not immobilised, but are present in a solution containing the cofactor regeneration system of the present invention. This approach would be particularly suited to those proteins/protein complexes which cannot be readily be immobilised. By way of example, multi-redox component cytochrome P450 mono-oxygenases or dioxygenases may be provided in a solution with the cofactor regeneration system of the present invention In one embodiment, the cofactor regeneration system of the present invention is employed to supply NADH to an NADH-dependant oxidoreductase (such as a NADH-dependent dehydrogenase) which is immobilised on the electronically conducting surface of the present invention (i.e. in addition to the first and second electron transfer components of the present invention).

In one embodiment, the cofactor regeneration system of the present invention is employed to supply NADH to an NADH-dependant oxidoreductase requiring $O_2$ (such as a NADH-dependent cytochrome P450 mono-oxygenase) which is immobilised on the electronically conducting surface of the present invention (i.e. in addition to the first and second electron transfer components of the present invention).

In one embodiment, the cofactor regeneration system of the present invention is employed to supply of $NAD^+$ to an $NAD^+$-dependant oxidoreductase (such as a $NAD^+$-dependent dehydrogenase) which is immobilised on the electronically conducting surface of the present invention (i.e. in addition to the first and second electron transfer components of the present invention).

In one embodiment, the cofactor regeneration system of the present invention is employed to supply of $NADP^+$ to an $NADP^+$-dependant oxidoreductase (such as a $NADP^+$-dependent aldehyde dehydrogenase) which is immobilised on the electronically conducting surface of the present invention (i.e. in addition to the first and second electron transfer components of the present invention).

In one embodiment, the cofactor regeneration system of the present invention is employed to supply of NADPH to an NADPH-dependent oxidoreductase (such as a NADPH-dependent carbonyl reductase or a NADPH-dependent cytochrome P450 mono-oxygenase) which is immobilised on the electronically conducting surface of the present invention (i.e. in addition to the first and second electron transfer components of the present invention).

In a further aspect, the invention provides a kit comprising or consisting of the cofactor regeneration system as described herein, or the diaphorase variant as described herein, and a cofactor selected from $NAD^+$, NADH, $NADP^+$ and/or NADPH. In one embodiment, the kit further comprises an oxidoreductase such as a dehydrogenase, a monooxygenase and/or a cytochrome p450 monooxygenase.

In another aspect of the present invention, there is provided a DNA sequence that encodes the first and/or second electron transfer components of the cofactor regeneration system of the present invention. In one embodiment, the present invention provides a DNA sequence of any of the SEQ ID NOs (i.e. any of SEQ ID NOs 1-72) representing the first and second electron transfer components described herein. In one embodiment, the DNA sequence is prepared as part of a DNA vector, wherein the vector comprises a promoter and terminator.

In one embodiment, the vector has a promoter selected from:

| Promoter | Induction Agent | Typical Induction Condition |
|---|---|---|
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |
| AcoE | Acetoin | 0.15% (0.05-0.5%) |
| SH promoter | self inducing during growth in Fructose-Glycerol-minimal medium | |

The DNA construct of the present invention may be designed in silico, and then synthesised by conventional DNA synthesis techniques.

The above-mentioned DNA sequence information is optionally modified for codon-biasing according to the ultimate host cell (e.g. *E. coli*) expression system that is to be employed.

Methods for expression of proteins in cellular (e.g. microbial) expression systems are well known and routine to those skilled in the art. In one embodiment, the first and second electron transfer components of the present inventions are encoded and expressed from the same vector in an appropriate host cell (e.g. a microbial cell, such as *E. coli*). In another embodiment, the first and second electron transfer components of the present invention are encoded and expressed from different/separate vectors in the same or different host cells. The extraction of the first and electron transfer components from said host cells post-expression can be achieved through routine methods known to those skilled in the art.

In one embodiment, the first and second electron transfer components of the present invention are expressed in the same host cell (e.g. a microbial host cell, such as *E. coli*) as an oxidoreductase selected from a dehydrogenase, reductase, oxidase, synthase, transhydrogenase, dioxygenase, mono-oxygenase, cytochrome p450 monooxygenase and/or ene reductase. Said oxidoreductase may be expressed from the same and/or a different/separate vector from the first and/or second electron transfer components.

Reeve, N. A., Lauterbach, L., Ash, P. A., Lenz, O., Vincent, K. A., 'A modular system for regeneration of NAD cofactors using graphite particles modified with hydrogenase and diaphorase moieties' Chem. Commun. 2012, 48 (10), 1589-1591 is incorporated herein, in its entirety, by reference thereto.

DEFINITIONS

Sequence Homology:

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position—Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes). Alignment Scores for Determining Sequence Identity

|  | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{\begin{array}{c}\text{[length of the longer sequence plus the}\\ \text{number of gaps introduced into the longer}\\ \text{sequence in order to align the two sequences]}\end{array}}\times 100$$

"R" is the standard nomenclature for a degeneracy of A or G at this position in a nucleotide sequence.

The present invention will now be described, by way of example only, with reference to the accompanying Examples and Figures, in which:

FIG. 1 shows UV-visible spectra demonstrating generation of NADH from a solution of $NAD^+$ (1 mM) saturated with $H_2$ by a cofactor regeneration system of the present invention consisting of pyrolytic graphite particles modified with *Ralstonia eutropha* soluble hydrogenase diaphorase domain (component (i)), and *Escherichia coli* hydrogenase 2 (component (ii)). The solution also contained potassium phosphate buffer, 50 mM, pH 7.0. The reaction was carried out at 20° C. The characteristic peak at 340 nm indicates NADH formation. Solid line: before addition of $H_2$; dashed line: 4.5 hours after addition of $H_2$.

Figure 2:
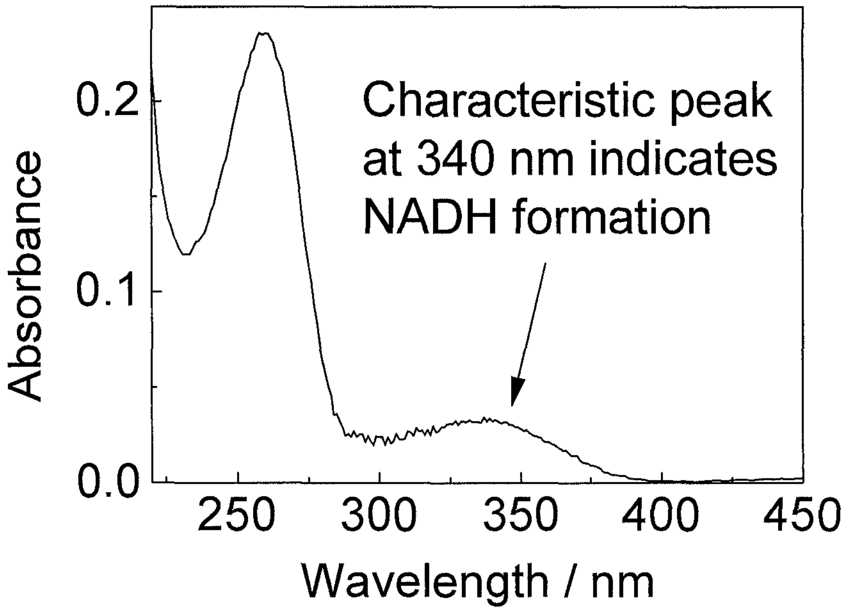

FIG. 2 shows a UV-visible spectrum demonstrating generation of NADH from a solution of $NAD^+$ (1 mM) saturated with a gas mixture of 99% $H_2$: 1% $O_2$ by a cofactor regeneration system of the present invention consisting of pyrolytic graphite particles modified with *Ralstonia eutropha* soluble hydrogenase HoxFU diaphorase domain (component (i)), and *Ralstonia eutropha* membrane-bound hydrogenase (component (ii)). The solution also contained potassium phosphate buffer, 50 mM, pH 7.0. The reaction was carried out at 20° C. The characteristic peak at 340 nm indicates NADH formation.

Figure 3:
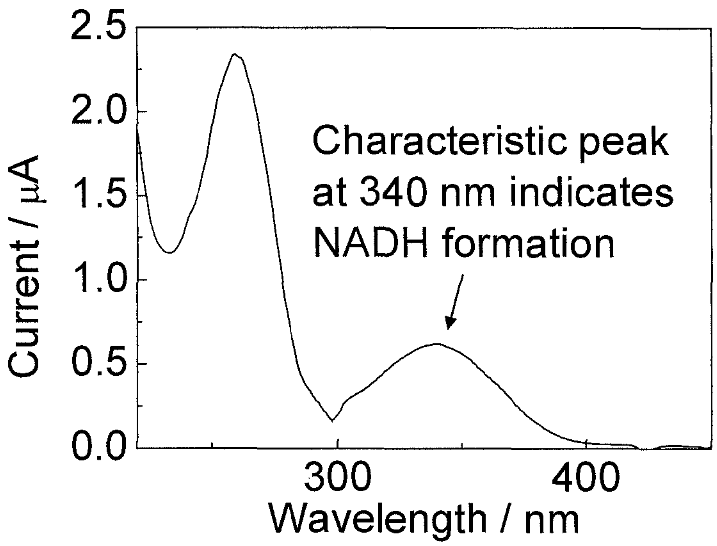

FIG. 3 shows a UV-visible spectrum demonstrating generation of NADH from a solution of $NAD^+$ (2 mM) by a cofactor regeneration system of the present invention consisting of pyrolytic graphite particles modified with *Ralstonia eutropha* HoxFU (component (i)) and *Escherichia coli* hydrogenase-1 (component (ii)). A gas mixture of 1% $O_2$ and 99% $H_2$ was continually flowed through the head space of the reaction vial. The solution also contained bis-Tris buffer, 50 mM, pH 6. The reaction was carried out at 20° C. The peak at 340 nm indicates NADH formation.

Figure 4:
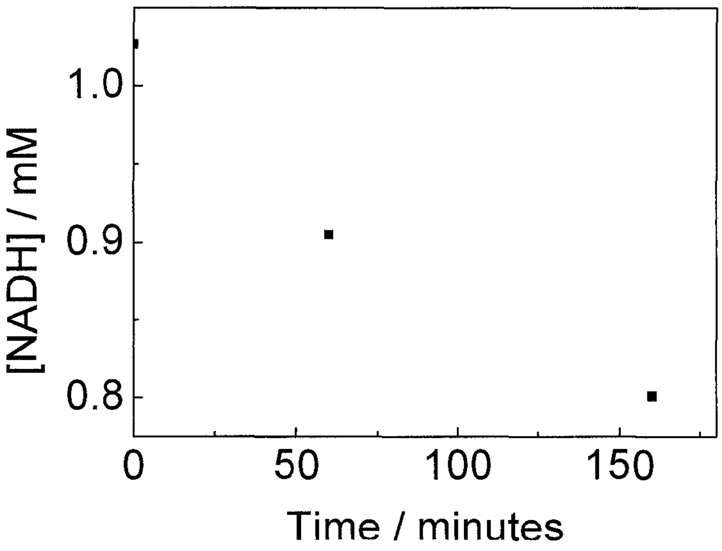

FIG. 4 shows a plot of NADH concentration over time during generation of $NAD^+$ from a solution of NADH (1 mM) saturated with $N_2$ by a cofactor regeneration system of the present invention consisting of pyrolytic graphite particles modified with *Escherichia coli* hydrogenase 2 (component (ii)) and *Ralstonia eutropha* H16 soluble hydrogenase diaphorase domain (HoxFU, component (i)). The solution also contained potassium phosphate buffer, 50 mM, pH 7.0. The reaction was carried out at 20° C. Samples were removed for analysis at the time points indicated. The concentration of NADH was determined by comparison of the ratio of absorbance at 260 nm to absorbance at 340 nm with the ratio for samples of known concentration ratio of NAD to NADH.

Figure 5:
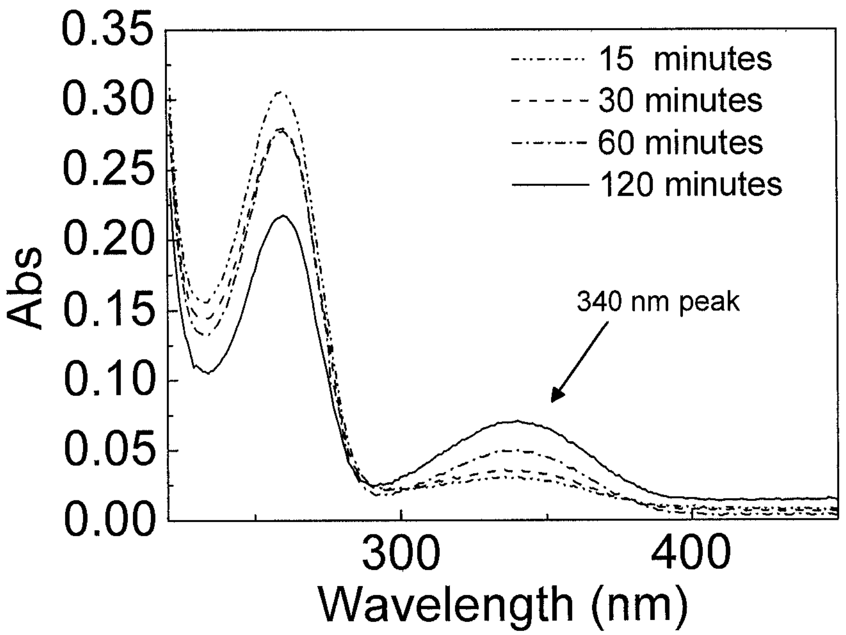

FIG. 5 shows UV-visible spectra demonstrating generation of NADH from a solution of $NAD^+$ (0.8 mM) saturated with $H_2$ by a cofactor regeneration system of the present invention consisting of pyrolytic graphite particles first modified with platinum (component (ii)), and then with *Ralstonia eutropha* soluble hydrogenase diaphorase domain (component (i)). The solution also contained potassium phosphate buffer, 50 mM, pH 7.0. The reaction was carried out at 20° C. The characteristic peak at 340 nm indicates NADH formation.

Figure 6:
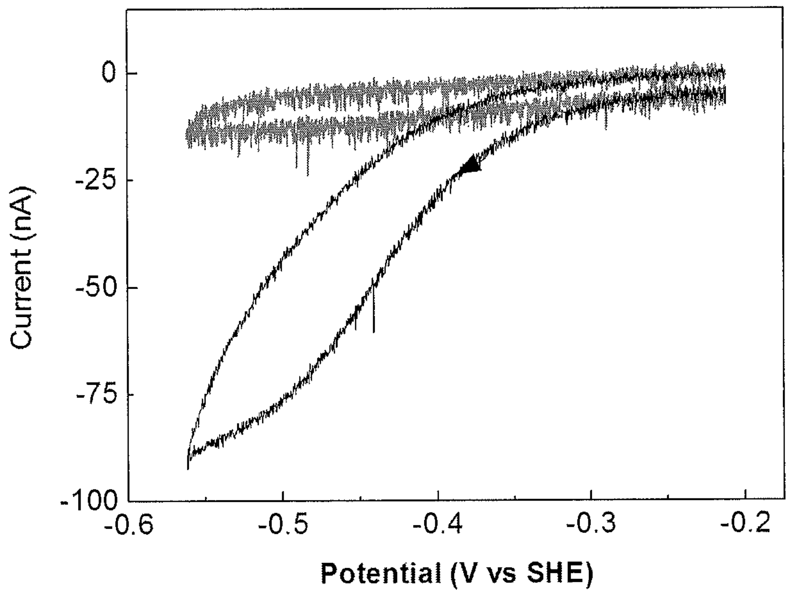

FIG. 6 shows a cyclic voltammogram demonstrating the response of an unmodified electrode (upper two lines) and an electrode modified with the HoxFUHY tetramer of *Ralstonia eutropha* soluble hydrogenase bearing a site directed mutation in the $NAD^+$ binding pocket which was intended to increase affinity for $NADP^+$ (lower two lines). Reduction of $NADP^+$ at minimal overpotential demonstrates the capacity for regenerating NADPH with electrons from $H_2$ using the cofactor regeneration system of the present invention with a variant of *Ralstonia eutropha* HoxFU diaphorase dimer in place of the native diaphorase dimer. The electrode is pyrolytic graphite 'edge', and is immersed in a solution containing 2 mM $NADP^+$ in Tris-HCl buffer, pH 8.0, at 30° C.

Figure 7:
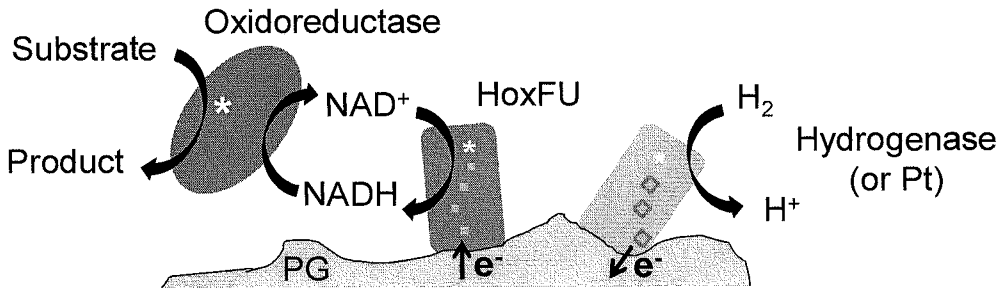

FIG. 7 shows a schematic of NADH regeneration using electrons from $H_2$ by pyrolytic graphite (PG) particles modified with a diaphorase (HoxFU subunits of *Ralstonia eutropha* soluble hydrogenase, component (i)) and a hydrogenase or Pt (component (ii)); ■ represents an iron sulfur electron relay cluster; * represents a catalytic active site. By appropriate choice of enzymes and conditions, the direction of catalysis can be reversed. In this schematic, NADH is supplied to an NADH-dependent oxidoreductase to support the transformation of substrate to product.

Figure 8:
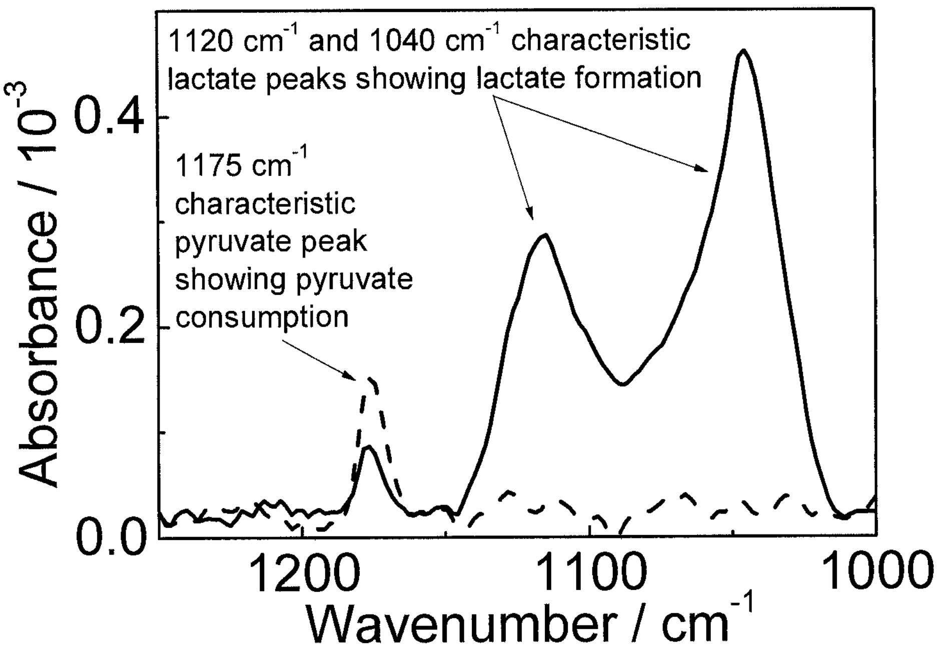

FIG. 8 shows that cofactor regeneration particles of the present invention can supply NADH to a cofactor dependent dehydrogenase. Attentuated Total Reflectance (ATR)-Infrared (IR) spectra of the supernatant solution before (dashed) and 7 hours after (solid) initiation by $H_2$ show conversion of pyruvate to lactate by lactate dehydrogenase (0.5 mg/ml). The dehydrogenase was supplied only with pyruvate (3 mM), $NAD^+$ (0.2 mM) and pyrolytic graphite particles modified with HoxFU and *E. coli* Hydrogenase-2 in pH 7.0, 50 mM potassium phosphate buffer. ATR-IR spectra were recorded using a Bio-Rad FTS-6000 FTIR spectrometer equipped with a diamond attenuated total reflectance accessory (DurasamplIR II, SensiR Technologies). The peak at 1175 $cm^{-1}$ demonstrates pyruvate consumption. The peaks at 1120 $cm^{-1}$ and 1040 $cm^{-1}$ demonstrate lactate formation.

Figure 9:
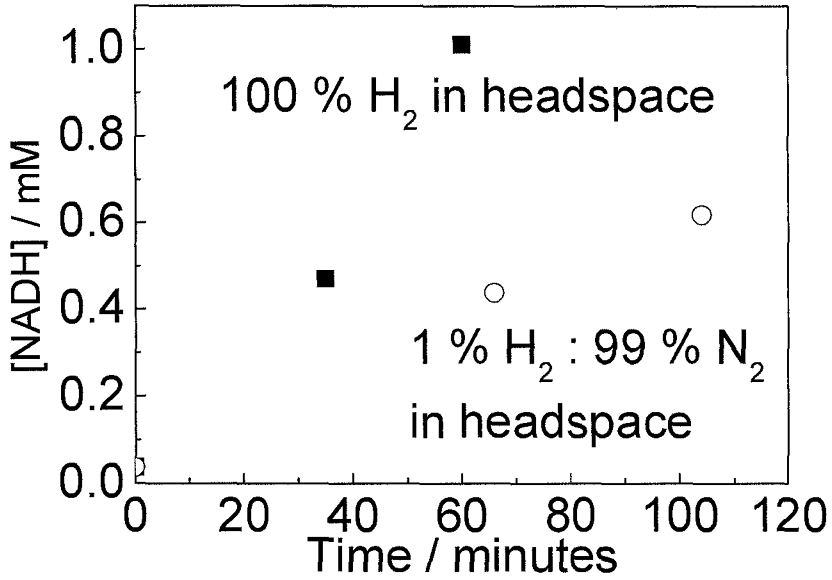

FIG. 9 shows a plot of NADH concentration over time during generation of NADH from a solution of $NAD^+$ (1 mM) by a cofactor regeneration system of the present invention consisting of pyrolytic graphite particles modified with *Ralstonia eutropha* soluble hydrogenase diaphorase domain HoxFU (component (i)), and *Escherichia coli* hydrogenase 2 (component (ii)). ○ represents a data series from an experiment performed under a gas mixture of 99% $N_2$: 1% $H_2$ at 1 bar. ■ represents a data series from an experiment performed under 100% $H_2$ at 1 bar. The solution also contained potassium phosphate buffer, 50 mM, pH 7.0. The reaction was carried out at 20° C. Aliquots were taken at the times indicated; a ratio of the UV-Vis spectra peaks at 260 nm and 340 nm was used to calculate the concentration of NADH by comparison with a standard curve. 100% conversion of $NAD^+$ to NADH is achieved after 60 minutes at 100% $H_2$.

Figure 10:
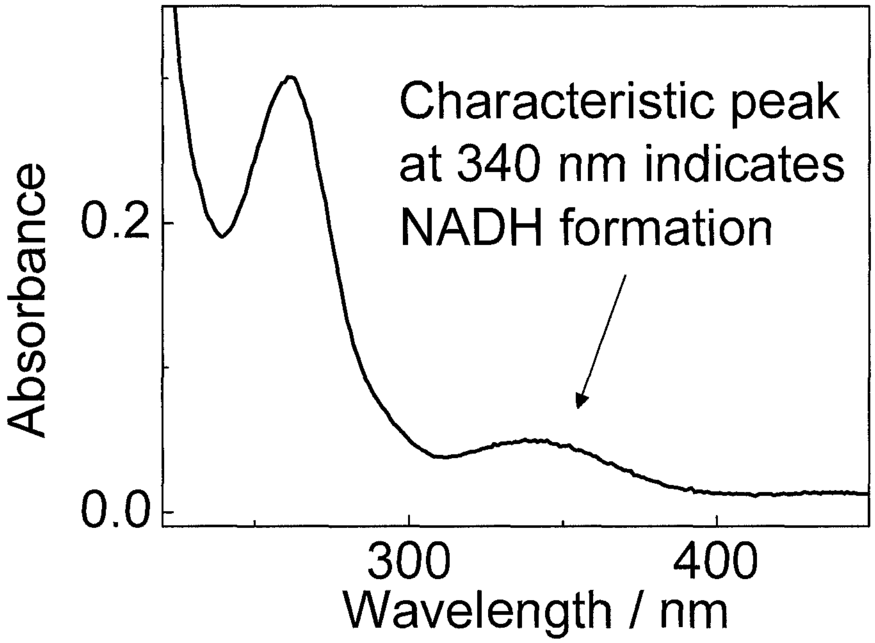

FIG. 10 shows a UV-visible spectrum demonstrating generation of NADH from a solution of $NAD^+$ (0.8 mM) saturated with $H_2$ at 1 bar by a cofactor regeneration system of the present invention consisting of pyrolytic graphite particles modified with soluble extract of *Ralstonia eutropha* HoxHYFU I64A variant in which the hydrogenase activity of HoxHY subunits is inactivated (component (i)), and *Desulfovibrio vulgaris* Miyazaki F Nickel-Iron hydrogenase (component (ii)). The solution also contained bis-Tris buffer, 100 mM, pH 6.0. The reaction was carried out at 20° C. The characteristic peak at 340 nm indicates NADH formation.

Figure 11:
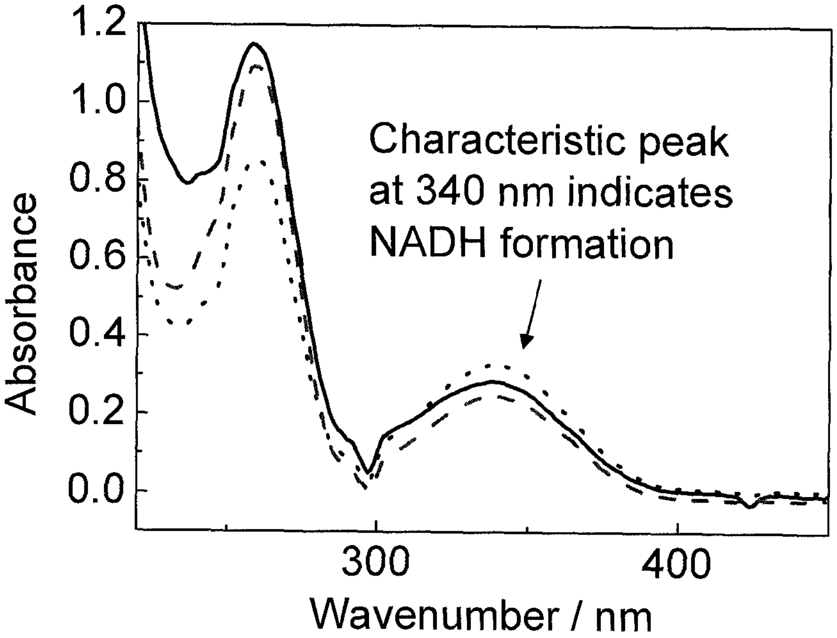

FIG. 11 shows UV-visible spectra demonstrating generation of NADH from a solution of $NAD^+$ (2 mM) saturated with $H_2$ at 1 bar by a cofactor regeneration system of the present invention consisting of carbon paper (solid line); carbon nanotubes (dotted line) or carbon nanopowder (dashed line) modified with *Ralstonia eutropha* HoxFU (component (i)) and *Desulfovibrio vulgaris* Miyazaki F hydrogenase (component (ii)). The solution also contained mixed buffer, 100 mM, pH 7.0. The reaction was carried out at 20° C. The characteristic peak at 340 nm indicates NADH formation.

Figure 12:
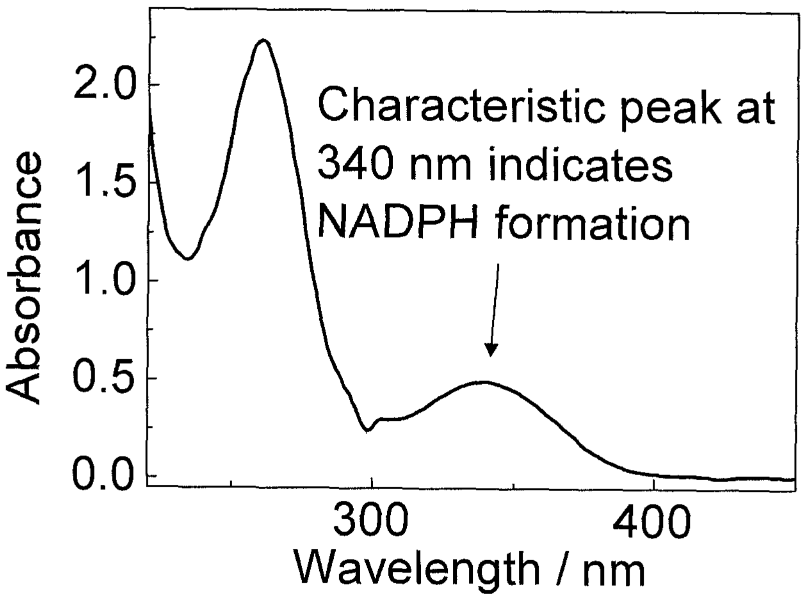

FIG. 12 shows a UV-visible spectrum demonstrating generation of NADPH from a solution of $NADP^+$ (2 mM) saturated with $H_2$ at 1 bar by a cofactor regeneration system of the present invention consisting of pyrolytic graphite particles modified with a variant of *Ralstonia eutropha* soluble hydrogenase (D467S E341A) (component (i)), and *Desulfovibrio vulgaris* Miyazaki F hydrogenase (component (ii)). The solution also contained bis-Tris buffer, 100 mM, pH 6.0. The reaction was carried out at 20° C. The characteristic peak at 340 nm indicates NADPH formation.

Figure 13:
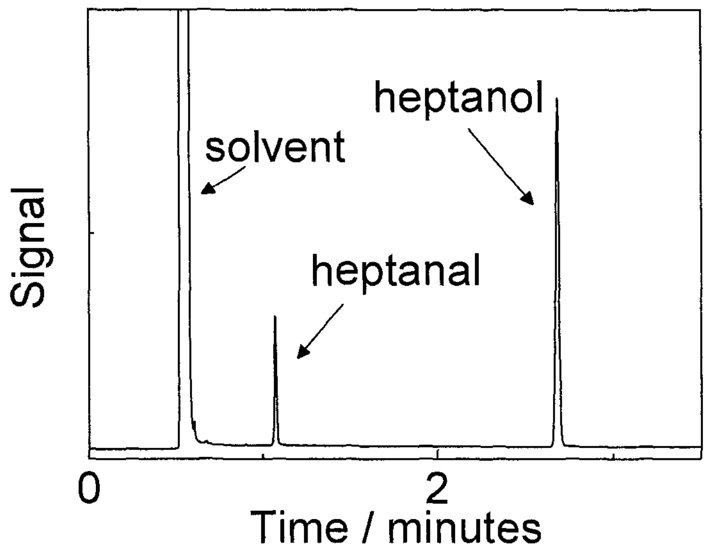
Figure 13:
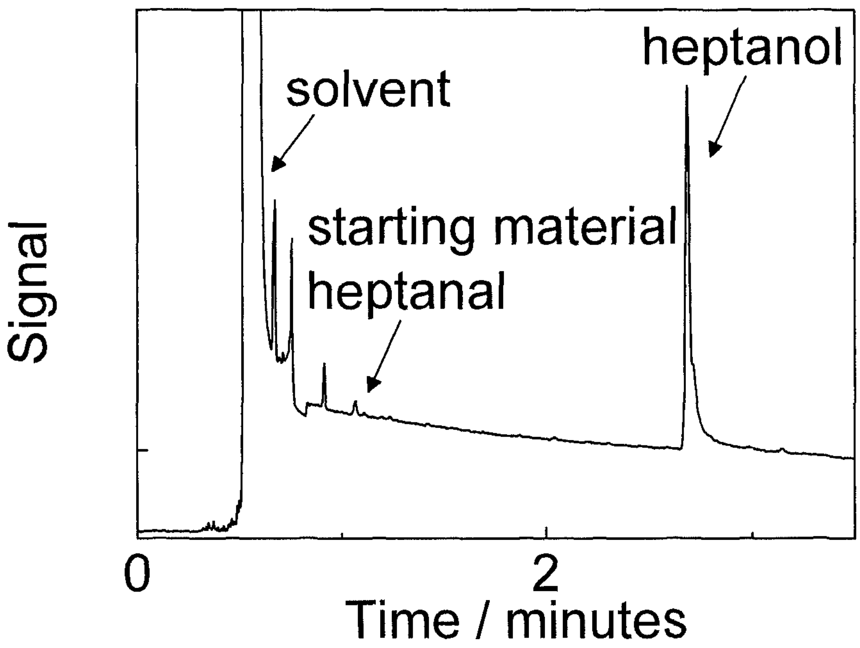

FIG. 13(*a*) shows a gas chromatogram of heptanal and heptanol standards. Heptanol and heptanal were extracted with ethyl acetate (300 μL) from an aqueous solution containing heptanol (1 mM), heptanal (1 mM) in pH 6, 100 mM bis-Tris buffer (1 mL).

FIG. 13(*b*) shows that cofactor regeneration particles of the present invention can supply NADH to a cofactor dependent dehydrogenase. Pyrolytic graphite particles were modified with soluble extract of *Ralstonia eutropha* soluble hydrogenase I64A variant (component (i)) and *Desulfovibrio vulgaris* Miyazaki F hydrogenase (component (ii)). *Saccharomyces cerevisiae* (yeast) alcohol dehydrogenase was included in the reaction solution (1500 Units) and was supplied with heptanal (10 mM) and $NAD^+$ (2 mM). The solution also contained bis-Tris buffer, 100 mM, pH 6.0. The reaction was carried out at 20° C. under a $H_2$ atmosphere at 1 bar. At the end of the experiment the heptanal and heptanol were extracted using ethyl acetate (300 μL). The gas chromatogram was collected on a ThermoFinnigan Trace GC. Comparison with the chromatogram of panel (a) confirms conversion of heptanal to heptanol.

KEY TO SEQ ID NOS

SEQ ID NO: 1 *Ralstonia eutropha* soluble hydrogenase diaphorase HoxF

SEQ ID NO: 2 *Ralstonia eutropha* soluble hydrogenase diaphorase HoxU

SEQ ID NO: 3 *Ralstonia eutropha* soluble hydrogenase diaphorase HoxI

SEQ ID NO: 4 flavoprotein (Fp) subcomplex of *Bos taurus* Complex 1, 51 kDa

SEQ ID NO: 5 flavoprotein (Fp) subcomplex of *Bos taurus* Complex 1, 24 kDa

SEQ ID NO: 6 *Ralstonia eutropha* $NAD^+$-dependent formate dehydrogenase, diaphorase moiety (FdsB)

SEQ ID NO: 7 *Ralstonia eutropha* $NAD^+$-dependent formate dehydrogenase, diaphorase moiety (FdsG)

SEQ ID NO: 8 NADPH oxidoreductase moiety from *Pyrococcus furiosus* soluble hydrogenase I gamma subunit SEQ ID NO: 9 NADPH oxidoreductase moiety from *Pyrococcus furiosus* soluble hydrogenase 1 beta subunit SEQ ID NO: 10 NADPH oxidoreductase moiety from *Pyrococcus furiosus* soluble hydrogenase II gamma subunit SEQ ID NO: 11 NADPH oxidoreductase moiety from *Pyrococcus furiosus* soluble hydrogenase II beta subunit SEQ ID NO: 12 Diaphorase moiety of *Rhodococcus opacus* SH HoxF SEQ ID NO: 13 Diaphorase moiety of *Rhodococcus opacus* SH HoxU SEQ ID NO: 14 Diaphorase moiety of *Allochromatium vinosum* SH, HoxF SEQ ID NO: 15 Diaphorase moiety of *Allochromatium vinosum* SH, HoxU SEQ ID NO: 16 Diaphorase moiety of *Thiocapsa roseopersicina* Hox1F SEQ ID NO: 17 Diaphorase moiety of *Thiocapsa roseopersicina* Hox1U SEQ ID NO: 18 Diaphorase moiety of *Thiocapsa roseopersicina* Hox2F SEQ ID NO: 19 Diaphorase moiety of *Thiocapsa roseopersicina* Hox2U SEQ ID NO: 20 Diaphorase moiety of *Synechocystis* sp. PCC 6803 HoxF SEQ ID NO: 21 Diaphorase moiety of *Synechocystis* sp. PCC 6803 HoxU SEQ ID NO: 22 Diaphorase moiety of *Synechococcus elongatus* PCC 6301 HoxF SEQ ID NO: 23 Diaphorase moiety of *Synechococcus elongatus* PCC 6301 HoxU SEQ ID NO: 24 *Ralstonia eutropha* soluble hydrogenase moiety (HoxH)

SEQ ID NO: 25 *Ralstonia eutropha* soluble hydrogenase moiety (HoxY)

SEQ ID NO: 26 *Ralstonia eutropha* membrane-bound hydrogenase moiety (HoxG)

SEQ ID NO: 27 *Ralstonia eutropha* membrane-bound hydrogenase moiety (HoxK)

SEQ ID NO: 28 *Ralstonia eutropha* membrane-bound hydrogenase moiety (HoxZ)

SEQ ID NO: 29 *Ralstonia eutropha* regulatory hydrogenase moiety (HoxB)

SEQ ID NO: 30 *Ralstonia eutropha* regulatory hydrogenase moiety (HoxC)

SEQ ID NO: 31 *Escherichia coli* hydrogenase 1 (large subunit)

SEQ ID NO: 32 *Escherichia coli* hydrogenase 1 (small subunit)

SEQ ID NO: 33 *Escherichia coli* hydrogenase 2 (large subunit)

SEQ ID NO: 34 *Escherichia coli* hydrogenase 2 (small subunit)

SEQ ID NO: 35 *Aquifex aeolicus* hydrogenase 1 (large subunit)

SEQ ID NO: 36 *Aquifex aeolicus* hydrogenase 1 (small subunit)

SEQ ID NO: 37 *Hydrogenovibrio marinus* hydrogenase (large subunit)

SEQ ID NO: 38 *Hydrogenovibrio marinus* hydrogenase (small subunit)

SEQ ID NO: 39 *Thiocapsa roseopersicina* hydrogenase HupL

SEQ ID NO: 40 *Thiocapsa roseopersicina* hydrogenase HupS

SEQ ID NO: 41 *Alteromonas macleodii* hydrogenase small subunit

SEQ ID NO: 42 *Alteromonas macleodii* hydrogenase large subunit

SEQ ID NO: 43 *Rhodococcus opacus* SH hydrogenase moiety HoxH

SEQ ID NO: 44 *Rhodococcus opacus* SH hydrogenase moiety HoxY

SEQ ID NO: 45 *Allochromatium vinosum* Membrane Bound Hydrogenase large subunit

SEQ ID NO: 46 *Allochromatium vinosum* Membrane Bound Hydrogenase small subunit

SEQ ID NO: 47 *Desulfovibrio fructosovorans* nickel-iron hydrogenase large subunit SEQ ID NO: 48 *Desulfovibrio fructosovorans* nickel-iron hydrogenase small subunit SEQ ID NO: 49 *Clostridium pasteurianum* iron-iron hydrogenase 1

SEQ ID NO: 50 *Clostridium acetobutylicum* iron-iron hydrogenase

SEQ ID NO: 51 *Chlamydomonas reinhardtii* iron-iron hydrogenase

SEQ ID NO: 52 *Desulfomicrobium baculatum* nickel-iron-selenium hydrogenase large subunit SEQ ID NO: 53 *Desulfomicrobium baculatum* nickel-iron-selenium hydrogenase small subunit SEQ ID NO: 54 *Ralstonia eutropha* diaphorase HoxF SH variant D326K (strain SH1344)

SEQ ID NO: 55 *Ralstonia eutropha* diaphorase HoxF SH variant D401K, strain SH1370

SEQ ID NO: 56 *Ralstonia eutropha* diaphorase HoxF SH variant D467S, strain SH1383

SEQ ID NO: 57 *Ralstonia eutropha* diaphorase HoxF SH variant D340A, strain SH841

SEQ ID NO: 58 *Ralstonia eutropha* diaphorase HoxF SH variant E341A, strain SH821

SEQ ID NO: 59 *Ralstonia eutropha* diaphorase HoxF SH variant SH D340A/E341A

SEQ ID NO: 60 *Ralstonia eutropha* diaphorase HoxF SH variant D340A/D401K

SEQ ID NO: 61 *Ralstonia eutropha* diaphorase HoxF SH variant D326K D401K

SEQ ID NO: 62 *Ralstonia eutropha* diaphorase HoxF SH variant D467S D401K

SEQ ID NO: 63 *Ralstonia eutropha* diaphorase HoxF SH variant D340N D467S

SEQ ID NO: 64 *Ralstonia eutropha* diaphorase HoxF SH variant E341A D467S

SEQ ID NO: 65 *Ralstonia eutropha* diaphorase HoxF SH variant E341H

SEQ ID NO: 66 *Rhodobacter capsulatus* diaphorase moiety of formate NAD+-reducing formate dehydrogenase from SB 1003, beta subunit FdsB SEQ ID NO: 67 *Rhodobacter capsulatus* diaphorase moiety of formate NAD+-reducing formate dehydrogenase SB 1003, gamma subunit FdsG:

SEQ ID NO: 68 *Ralstonia eutropha* soluble hydrogenase moiety variant HoxH_I64A

SEQ ID NO: 69 *Desulfovibrio vulgaris* Nickel Iron hydrogenase Small subunit, pdb 1H2A, Chain S SEQ ID NO: 70 *Desulfovibrio vulgaris* Nickel Iron hydrogenase Large subunit, pdb 1H2A, Chain L SEQ ID NO: 71 *Desulfovibrio gigas* Periplasmic [NiFe] hydrogenase Small subunit SEQ ID NO: 72 *Desulfovibrio gigas* Periplasmic [NiFe] hydrogenase Large subunit SEQ ID NO: 73 *Ralstonia eutropha* hoxF nucleotide sequence SEQ ID NO: 74 *Ralstonia eutropha* hoxU nucleotide sequence SEQ ID NO: 75 *Ralstonia eutropha* hoxK nucleotide sequence SEQ ID NO: 76 *Ralstonia eutropha* hoxG nucleotide sequence SEQ ID NO: 77 *Ralstonia eutropha* hoxZ nucleotide sequence

EXAMPLES

Example 1

NADH Cofactor Regeneration System

All steps were carried out in an anaerobic glove box (Glove Box Technology or MBraun) under an atmosphere of $N_2$. Particles of pyrolytic graphite were prepared by abrasion of a piece of pyrolytic graphite with emery paper. These particles were immersed in 50 mM potassium phosphate buffer and suspended by sonication (5 minutes, ultrasonic bath). An aliquot of the particle suspension was removed. To this aliquot was added an aliquot of *Escherichia coli* hydrogenase 2 (component (ii), $10^{-12}$ moles) and an aliquot of *Ralstonia eutropha* diaphorase (component (i), HoxFU, $10^{-11}$ moles). The particles and enzymes were left at 4° C. for 10 minutes to allow the enzyme components to adsorb onto the particles. Centrifugation (5 minutes, benchtop centrifuge) was used to separate the particles and to remove excess unadsorbed enzyme. The enzyme-modified particles were then resuspended in 1 mM $NAD^+$ in potassium phosphate buffer (50 mM, pH 7.0). The particle suspension was placed in a vial sealed with a septum and the headspace of the vial was exchanged for $H_2$ gas via inlet and outlet needles. Aliquots were removed at specific time intervals for analysis for $NAD^+$/NADH content. Each aliquot was centrifuged to remove particles, removed from the anaerobic glove box, and examined using ultra-violet/visible spectroscopy. NADH generation was observed.

Example 2

$NAD^+$ Cofactor Regeneration System

All steps were carried out in an anaerobic glove box (Glove Box Technology or MBraun) under an atmosphere of $N_2$. Pyrolytic graphite particles modified with *Escherichia coli* hydrogenase 2 (component (ii)) and *Ralstonia eutropha* diaphorase (HoxFU, component (i)) were prepared as described in Example 1. After collection of the enzyme-modified particles by centrifugation, the particles were resuspended in 1 mM NADH in potassium phosphate buffer (50 mM, pH 7.0). The particle suspension was placed in a vial sealed with a septum containing $N_2$ gas. Aliquots were removed at specific time intervals for analysis for $NAD^+$/NADH content. Each aliquot was centrifuged to remove particles and examined using ultra-violet/visible spectroscopy. NAD+ generation was observed.

Example 3

Preparation of Wild-Type and Variant *R. eutropha* Diaphorase (HoxFU)

For purification of wild type HoxFU and variants, *R. eutropha* cells containing plasmid pHoxFU harboring the genes hoxFUIhypA2B2F2CDEX (the hoxF gene was equipped at the 3' end with a sequence encoding the Strep-tag II peptide) were grown heterotrophically in a mineral salts medium containing a mixture of 0.2% (w/v) fructose and 0.2% (v/v) glycerol supplemented with 1 μM $NiCl_2$ and 1 μM $ZnCl_2$. (Lauterbach et al. PLoS ONE doi:10.1371/journal.pone.0025939). Cells were harvested at an optical density at 436 nm of 9 to 11 and washed with 50 mM potassium phosphate (K-$PO_4$) buffer, pH 7.0 containing 50 mM succinate. The resulting cell pellet was resuspended in two volumes of resuspension buffer (50 mM Tris-HCl, 150 mM KCl, 5% glycerol, pH 8.0 containing Protease Inhibitor (EDTA-free, Roche). After two passages through a chilled French pressure cell at 6.2 MPa, the suspension was centrifuged at 100,000×g for 45 min. The soluble extract was applied to a 2 mL Strep-Tactin Superflow column (IBA), washed with 6 mL of resuspension buffer and eluted with the same buffer containing 5 mM desthiobiotin (Lauterbach et al. PLoS ONE doi:10.1371/journal.pone.0025939). Fractions containing HoxFU protein were pooled, concentrated and subsequently used for immobilization on graphite particles.

Diaphorase (HoxFU) variants were isolated as described above except that the hoxF sequence on plasmid pHoxFU was altered by genetic engineering which resulted in the production of HoxFU variants containing specific amino acid exchanges, to improve, inter alia, the NADP(H) binding affinity.

Example 4

Preparation of Soluble Extract HoxHYFUI2 (SH I64A)

The *R. eutropha* HF210 strains with the plasmid pGE747 for production of the SHI64 derivative were grown heterotrophically in a mineral salts medium containing a mixture of 0.2% (w/v) fructose and 0.2% (v/v) glycerol (FGN medium), which were harvested at an optical density at 436 nm of 9 to 11. For preparing soluble extract HoxHYFUI2 of the SHI64 derivative, the cells were resuspended in two volumes of 50 mm Tris-HCl, 150 mm KCl, pH 8.0 buffer containing a protease inhibitor cocktail (EDTA-free Protease Inhibitor, Roche). Cells were broken by two passages through a chilled French pressure cell at 6.2 MPa and the resulting suspension was centrifuged at 100,000 g for 45 min. The supernatant (soluble extract) was applied for preparing particles.

Example 5

Use of Cofactor Regeneration System of the Present Invention to Regenerate NADH for a Dehydrogenase Pyrolytic graphite particles modified with *Escherichia coli* hydrogenase 2 (component (ii)) and *Ralstonia eutropha* diaphorase (HoxFU, component (i)) were prepared in an anaerobic glove box (Glove Box Technology or MBraun) as described in Example 1. After collection of the enzyme-modified particles by centrifugation, the particles were added to a solution containing S-Lactate dehydrogenase (Sigma, 0.5 mg/mL) and pyruvate (3 mM). To this suspension was added $NAD^+$ (0.2 mM), and the suspension was equilibrated with $H_2$ gas at atmospheric pressure. The formation of lactate was detected by Attentuated Total Reflectance Fourier Transform InfraRed spectroscopy using a diamond Attentuated Total Reflectance accessory (DurasampIIR II, SensIR Technologies).

Example 6

Use of Cofactor Regeneration System to Supply NADH to an NADH-Dependent Dehydrogenase Enzyme The product of the dehydrogenase enzyme is a high value fine chemical or pharmaceutical product. A reactor is supplied with particles modified with *E. coli* hydrogenase 2 (component (ii)) and *R. eutropha* HoxFU (component (i)). The reactor is also supplied with the dehydrogenase enzyme, the substrate of the dehydrogenase enzyme (500 mM), $NAD^+$ (1 mM), and $H_2$. After a certain period of time, the product of the dehydrogenase reaction is collected from the reactor (eg by solvent extraction).

Example 7

Regeneration of NADH for Supply to a Dehydrogenase

The cofactor regeneration system of the present invention is placed in a solution of $NAD^+$ (eg 0.2 mM) under an atmosphere comprising mainly $H_2$ (eg $H_2$ gas, or 90% $H_2$/10% $N_2$). An NADH-dependent dehydrogenase (eg lactate dehydrogenase) is added to the solution (or is attached to the electronically conducting surface). The substrate for the dehydrogenase (eg pyruvate for lactate dehydrogenase) is placed in the solution. The product of the dehydrogenase reaction (eg S-lactate for S-lactate dehydrogenase) can be collected continuously or batchwise.

Example 8

Regeneration of NADH for Supply to a P450 Monoxygenase

The cofactor regeneration system of the present invention is placed in a solution (free or immobilised on an electrically conducting surface) of $NAD^+$ (eg 0.2 mM) under an atmosphere comprising mainly $H_2$ with a small amount of $O_2$ (eg 99% $H_2$/1% $O_2$). An NADH-dependent cytochrome P450 mono-oxygenase enzyme is added to the solution (or is attached to the electronically conducting surface). The substrate for the cytochrome P450 mono-oxygenase is placed in the solution. The product of the cytochrome P450 mono-oxygenase reaction can be collected continuously or batchwise.

Example 9

Regeneration of $NAD^+$ for Supply to a Dehydrogenase

The cofactor regeneration system of the present invention is placed in a solution of NADH (eg 0.2 mM) under an under an inert atmosphere (eg $N_2$, argon) or an atmosphere containing low level $H_2$ (eg 1%). An $NAD^+$-dependent dehydrogenase (eg alcohol dehydrogenase) is added to the solution (or is attached to the electronically conducting surface). The substrate for the dehydrogenase (eg ethanol for alcohol dehydrogenase) is placed in the solution. The product of the dehydrogenase reaction (eg acetaldehyde for alcohol dehydrogenase) can be collected continuously or batchwise.

Example 10

NADPH Cofactor Regeneration System

All steps were carried out in an anaerobic glove box (Glove Box Technology or MBraun) under an atmosphere of N2. Particles of pyrolytic graphite were prepared by abrasion of a piece of pyrolytic graphite with emery paper. These particles were immersed in 100 mM bis-Tris buffer, pH 6.0 and suspended by sonication (5 minutes, ultrasonic bath). An aliquot of the particle suspension was removed. To this aliquot was added an aliquot of *D. vulgaris* Miyazaki F hydrogenase (component (ii)) and an aliquot of a variant of *Ralstonia eutropha* diaphorase (HoxHYFU, D467S E341A) (component (i)). The particles and enzymes were left at 4° C. for 10 minutes to allow the enzyme components to adsorb onto the particles. Centrifugation (5 minutes, benchtop centrifuge) was used to separate the particles and to remove excess unadsorbed enzyme. The enzyme-modified particles were then resuspended in 2 mM $NADP^+$ in bis-Tris buffer (100 mM, pH 6.0). The particle suspension was placed in a vial sealed with a septum and the headspace of the vial was exchanged for $H_2$ gas via inlet and outlet needles. Aliquots were removed at specific time intervals for analysis for $NADP^+$/NADPH content. Each aliquot was centrifuged to remove particles, removed from the anaerobic glove box, and examined using ultra-violet/visible spectroscopy. NADPH generation was observed.

Example 11

Use of Cofactor Regeneration System of the Present Invention to Regenerate NADH for Yeast Alcohol Dehydrogenase Pyrolytic graphite particles modified with *Escherichia coli* hydrogenase 2 (component (ii)) and a soluble extract of *Ralstonia eutropha* diaphorase (HoxHYFU, I64A variant, component (i)) were prepared in an anaerobic glove box (Glove Box Technology or MBraun) according to the methodology described in Example 1. After collection of the enzyme-modified particles by centrifugation, the particles were then added to a solution containing yeast alcohol dehydrogenase and heptanal (10 mM). To this suspension was added $NAD^+$ (2 mM), and the suspension was equilibrated with $H_2$ gas at atmospheric pressure. Ethyl acetate was added to the final solution to extract the product. After thorough mixing, the organic and aqueous phases were separated by centrifugation. The formation of 1-heptanol in the organic phase was confirmed by gas chromatography detection.

Example 12

NADH Cofactor Regeneration System with Co-Expressed Soluble Extract

Cells from a strain of *Ralstonia eutropha* H16 incorporating plasmids encoding the membrane bound hydrogenase and HoxFU are broken open. The membrane bound hydrogenase is solubilized from the membrane by the addition of detergent Triton X-100 to crude cell extracts. A subsequent high-speed centrifugation step leads to a soluble extract containing both membrane bound hydrogenase (component (ii)) and HoxFU (component (i)). A soluble cell extract of an

*Escherichia coli* strain with overexpressed alcohol dehydrogenase is added to the *Ralstonia eutropha* soluble extract. Carbon-based particles are added to the soluble extract and left for 30 minutes at 4° C. The particle suspension is warmed to 30° C. and the substrate for the alcohol dehydrogenase is added to a concentration of 500 mM. $NAD^+$ is also added to a concentration of 1 mM and $H_2$ gas is gently bubbled into the solution. After 10 hours the product of the alcohol dehydrogenase reaction is collected by solvent extraction.

The invention claimed is:

1. A system for the regeneration of the cofactors nicotinamide adenine dinucleotide (NAD+), the reduced form of NAD+ (NADH), nicotinamide adenine dinucleotide phosphate (NADP+), and the reduced form of NADP+ (NADPH), the system comprising:

i) a first electron transfer component comprising a diaphorase, wherein said diaphorase comprises a first polypeptide comprising a sequence having at least 94% identity to SEQ ID NO: 1 and a second polypeptide comprising a sequence having at least 80% identity to SEQ ID NO: 2, wherein the combination of the first and second sequences provides oxidoreductase activity;

ii) a second electron transfer component comprising a hydrogenase, wherein said hydrogenase comprises a first polypeptide comprising a sequence having at least 95% identity to SEQ ID NO: 33 and a second polypeptide comprising a sequence having at least 90% identity to SEQ ID NO: 34, wherein the combination of the first and second sequences provides hydrogenase activity; and, iii) an electronically conducting surface wherein said electronically conducting surface is a carbon particle;

wherein the first and second electron transfer components are immobilised on the carbon particle, wherein the first and second electron transfer components do not occur together in nature as an enzyme complex, and wherein, when the cofactor regeneration system is in use, electrons flow:

from the first electron transfer component via the carbon particle to the second electron transfer component; or from the second electron transfer component via the carbon particle to the first electron transfer component.

2. The cofactor regeneration system according to claim 1, wherein the diaphorase has increased oxidoreductase activity compared to Ralstonia eutropha diaphorase consisting of SEQ ID NO: 1 and SEQ ID NO: 2.

3. The cofactor regeneration system according to claim 2, wherein the catalytic activity of said diaphorase is increased by a factor of at least 50.

4. The cofactor regeneration system according to claim 1, wherein the hydrogenase does not comprise a flavin mononucleotide (FMN) prosthetic group, does not comprise a flavin adenine dinucleotide (FAD) prosthetic group, or does not comprise a FMN prosthetic group and does not comprise a FAD prosthetic group.

5. The cofactor regeneration system according to claim 1, further comprising NAD+.

6. A kit comprising the cofactor regeneration system according to claim 1, and a cofactor selected from NAD, NADH, NADP and/or NADPH.

7. The cofactor regeneration system according to claim 1, further comprising NADH.

8. The cofactor regeneration system according to claim 1, further comprising NADP+.

9. The cofactor regeneration system according to claim 1, further comprising NADPH.

* * * * *

SEQUENCE LISTING

```
<160> NUMBER OF SEQ ID NOS: 77

<210> SEQ ID NO 1
<211> LENGTH: 602
<212> TYPE: PRT
<213> ORGANISM: Ralstonia eutropha

<400> SEQUENCE: 1

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
```

```
                325                 330                 335

Ile Cys Gly Asp Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Asp Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600


<210> SEQ ID NO 2
<211> LENGTH: 234
<212> TYPE: PRT
<213> ORGANISM: Ralstonia eutropha

<400> SEQUENCE: 2

Met Ser Ile Gln Ile Thr Ile Asp Gly Lys Thr Leu Thr Thr Glu Glu
1               5                   10                  15

Gly Arg Thr Leu Val Asp Val Ala Ala Glu Asn Gly Val Tyr Ile Pro
            20                  25                  30

Thr Leu Cys Tyr Leu Lys Asp Lys Pro Cys Leu Gly Thr Cys Arg Val
        35                  40                  45

Cys Ser Val Lys Val Asn Gly Asn Val Ala Ala Ala Cys Thr Val Arg
    50                  55                  60

Val Ser Lys Gly Leu Asn Val Glu Val Asn Asp Pro Glu Leu Val Asp
65                  70                  75                  80

Met Arg Lys Ala Leu Val Glu Phe Leu Phe Ala Glu Gly Asn His Asn
                85                  90                  95
```

-continued

```
Cys Pro Ser Cys Glu Lys Ser Gly Arg Cys Gln Leu Gln Ala Val Gly
            100                 105                 110

Tyr Glu Val Asp Met Met Val Ser Arg Phe Pro Tyr Arg Phe Pro Val
        115                 120                 125

Arg Val Val Asp His Ala Ser Glu Lys Ile Trp Leu Glu Arg Asp Arg
    130                 135                 140

Cys Ile Phe Cys Gln Arg Cys Val Glu Phe Ile Arg Asp Lys Ala Ser
145                 150                 155                 160

Gly Arg Lys Ile Phe Ser Ile Ser His Arg Gly Pro Glu Ser Arg Ile
                165                 170                 175

Glu Ile Asp Ala Glu Leu Ala Asn Ala Met Pro Pro Glu Gln Val Lys
            180                 185                 190

Glu Ala Val Ala Ile Cys Pro Val Gly Thr Ile Leu Glu Lys Arg Val
        195                 200                 205

Gly Tyr Asp Asp Pro Ile Gly Arg Arg Lys Tyr Glu Ile Gln Ser Val
    210                 215                 220

Arg Ala Arg Ala Leu Glu Gly Glu Asp Lys
225                 230


<210> SEQ ID NO 3
<211> LENGTH: 167
<212> TYPE: PRT
<213> ORGANISM: Ralstonia eutropha

<400> SEQUENCE: 3

Met Lys Glu Gln Glu Ile Asp Arg Ile Ala Thr Met Ile Tyr Glu Ala
1               5                   10                  15

Pro Leu Gly Glu Tyr Ile Gly Arg Asp Gly Ala Ala Ile Leu Ala Glu
            20                  25                  30

His Ala Ala Glu Ala Arg Leu Leu Lys Gly Asp Glu Phe Leu Tyr Arg
        35                  40                  45

Arg Gly Asp Val Thr Ser Ser Phe Tyr Ile Val Thr Asp Gly Arg Leu
    50                  55                  60

Ala Leu Val Arg Glu Lys Thr Asn Glu Arg Thr Ala Pro Ile Val His
65                  70                  75                  80

Val Leu Glu Lys Gly Asp Leu Val Gly Glu Leu Gly Phe Ile Asp Gln
                85                  90                  95

Thr Pro His Ser Leu Ser Val Arg Ala Leu Gly Asp Ala Ala Val Leu
            100                 105                 110

Ser Phe Ser Ala Glu Ser Ile Lys Pro Leu Ile Thr Glu His Pro Glu
        115                 120                 125

Leu Ile Phe Asn Phe Met Arg Ala Val Ile Lys Arg Val His His Val
    130                 135                 140

Val Val Thr Val Gly Glu His Glu Arg Glu Leu Gln Glu Tyr Ile Ser
145                 150                 155                 160

Thr Gly Gly Arg Gly Arg Gly
                165


<210> SEQ ID NO 4
<211> LENGTH: 464
<212> TYPE: PRT
<213> ORGANISM: Bos taurus

<400> SEQUENCE: 4

Met Leu Ala Ala Arg Arg Leu Leu Gly Gly Ser Leu Pro Ala Arg Val
1               5                   10                  15
```

-continued

```
Ser Val Arg Phe Ser Gly Asp Thr Thr Ala Pro Lys Lys Thr Ser Phe
            20                  25                  30

Gly Ser Leu Lys Asp Glu Asp Arg Ile Phe Thr Asn Leu Tyr Gly Arg
        35                  40                  45

His Asp Trp Arg Leu Lys Gly Ala Gln Ser Arg Gly Asp Trp Tyr Lys
    50                  55                  60

Thr Lys Glu Ile Leu Leu Lys Gly Pro Asp Trp Ile Leu Gly Glu Val
65                  70                  75                  80

Lys Thr Ser Gly Leu Arg Gly Arg Gly Gly Ala Gly Phe Pro Thr Gly
                85                  90                  95

Leu Lys Trp Ser Phe Met Asn Lys Pro Ser Asp Gly Arg Pro Lys Tyr
            100                 105                 110

Leu Val Val Asn Ala Asp Glu Gly Glu Pro Gly Thr Cys Lys Asp Arg
        115                 120                 125

Glu Ile Ile Arg His Asp Pro His Lys Leu Val Glu Gly Cys Leu Val
    130                 135                 140

Gly Gly Arg Ala Met Gly Ala Arg Ala Ala Tyr Ile Tyr Ile Arg Gly
145                 150                 155                 160

Glu Phe Tyr Asn Glu Ala Ser Asn Leu Gln Val Ala Ile Arg Glu Ala
                165                 170                 175

Tyr Glu Ala Gly Leu Ile Gly Lys Asn Ala Cys Gly Ser Gly Tyr Asp
            180                 185                 190

Phe Asp Val Phe Val Val Arg Gly Ala Gly Ala Tyr Ile Cys Gly Glu
        195                 200                 205

Glu Thr Ala Leu Ile Glu Ser Ile Glu Gly Lys Gln Gly Lys Pro Arg
    210                 215                 220

Leu Lys Pro Pro Phe Pro Ala Asp Val Gly Val Phe Gly Cys Pro Thr
225                 230                 235                 240

Thr Val Ala Asn Val Glu Thr Val Ala Val Ser Pro Thr Ile Cys Arg
                245                 250                 255

Arg Gly Gly Ala Trp Phe Ala Ser Phe Gly Arg Glu Arg Asn Ser Gly
            260                 265                 270

Thr Lys Leu Phe Asn Ile Ser Gly His Val Asn Asn Pro Cys Thr Val
        275                 280                 285

Glu Glu Glu Met Ser Val Pro Leu Lys Glu Leu Ile Glu Lys His Ala
    290                 295                 300

Gly Gly Val Thr Gly Gly Trp Asp Asn Leu Leu Ala Val Ile Pro Gly
305                 310                 315                 320

Gly Ser Ser Thr Pro Leu Ile Pro Lys Ser Val Cys Glu Thr Val Leu
                325                 330                 335

Met Asp Phe Asp Ala Leu Ile Gln Ala Gln Thr Gly Leu Gly Thr Ala
            340                 345                 350

Ala Val Ile Val Met Asp Arg Ser Thr Asp Ile Val Lys Ala Ile Ala
        355                 360                 365

Arg Leu Ile Glu Phe Tyr Lys His Glu Ser Cys Gly Gln Cys Thr Pro
    370                 375                 380

Cys Arg Glu Gly Val Asp Trp Met Asn Lys Val Met Ala Arg Phe Val
385                 390                 395                 400

Arg Gly Asp Ala Arg Pro Ala Glu Ile Asp Ser Leu Cys Glu Ile Ser
                405                 410                 415

Lys Gln Ile Glu Gly His Thr Ile Cys Ala Leu Gly Asp Gly Ala Ala
            420                 425                 430

Trp Pro Val Gln Gly Leu Ile Arg His Phe Arg Pro Glu Leu Glu Glu
```

```
        435                 440                 445

Arg Met Gln Gln Phe Ala Gln Gln His Gln Ala Arg Gln Ala Ala Phe
    450                 455                 460


<210> SEQ ID NO 5
<211> LENGTH: 249
<212> TYPE: PRT
<213> ORGANISM: Bos taurus

<400> SEQUENCE: 5

Met Phe Leu Ser Ala Ala Leu Arg Ala Arg Ala Ala Gly Leu Ala Ala
1               5                   10                  15

His Trp Gly Lys His Ile Arg Asn Leu His Lys Thr Ala Val Gln Asn
            20                  25                  30

Gly Ala Gly Gly Ala Leu Phe Val His Arg Asp Thr Pro Glu Asn Asn
        35                  40                  45

Pro Glu Thr Pro Phe Asp Phe Thr Pro Glu Asn Tyr Lys Arg Ile Glu
    50                  55                  60

Ala Ile Val Lys Asn Tyr Pro Glu Gly His Lys Ala Ala Ala Val Leu
65                  70                  75                  80

Pro Val Leu Asp Leu Ala Gln Arg Gln Asn Gly Trp Leu Pro Ile Ser
                85                  90                  95

Ala Met Asn Lys Val Ala Glu Ile Leu Gln Val Pro Pro Met Arg Val
            100                 105                 110

Tyr Glu Val Ala Thr Phe Tyr Thr Met Tyr Asn Arg Lys Pro Val Gly
        115                 120                 125

Lys Tyr His Ile Gln Val Cys Thr Thr Thr Pro Cys Met Leu Arg Asn
    130                 135                 140

Ser Asp Ser Ile Leu Glu Ala Ile Gln Lys Lys Leu Gly Ile Lys Val
145                 150                 155                 160

Gly Glu Thr Thr Pro Asp Lys Leu Phe Thr Leu Ile Glu Val Glu Cys
                165                 170                 175

Leu Gly Ala Cys Val Asn Ala Pro Met Val Gln Ile Asn Asp Asn Tyr
            180                 185                 190

Tyr Glu Asp Leu Thr Pro Lys Asp Ile Glu Glu Ile Ile Asp Glu Leu
        195                 200                 205

Lys Ala Gly Lys Ile Pro Lys Pro Gly Pro Arg Ser Gly Arg Phe Ser
    210                 215                 220

Cys Glu Pro Ala Gly Gly Leu Thr Ser Leu Thr Glu Pro Pro Lys Gly
225                 230                 235                 240

Pro Gly Phe Gly Val Gln Ala Gly Leu
                245


<210> SEQ ID NO 6
<211> LENGTH: 520
<212> TYPE: PRT
<213> ORGANISM: Ralstonia eutropha

<400> SEQUENCE: 6

Met Ile Thr Ile Thr Thr Ile Phe Val Pro Arg Asp Ser Thr Ala Leu
1               5                   10                  15

Ala Leu Gly Ala Asp Asp Val Ala Arg Ala Ile Ala Arg Glu Ala Ala
            20                  25                  30

Ala Arg Asn Glu His Val Arg Ile Val Arg Asn Gly Ser Arg Gly Met
        35                  40                  45

Phe Trp Leu Glu Pro Leu Val Glu Val Gln Thr Gly Ala Gly Arg Val
```

-continued

```
    50                  55                  60

Ala Tyr Gly Pro Val Ser Ala Ala Asp Val Pro Gly Leu Phe Asp Ala
65                  70                  75                  80

Gly Leu Leu Gln Gly Gly Glu His Ala Leu Ser Gln Gly Val Thr Glu
                85                  90                  95

Glu Ile Pro Phe Leu Lys Gln Gln Glu Arg Leu Thr Phe Ala Arg Val
            100                 105                 110

Gly Ile Thr Asp Pro Leu Ser Leu Asp Asp Tyr Arg Ala His Glu Gly
        115                 120                 125

Phe Ala Gly Leu Glu Arg Ala Leu Ala Met Gln Pro Ala Glu Ile Val
    130                 135                 140

Gln Glu Val Thr Asp Ser Gly Leu Arg Gly Arg Gly Gly Ala Ala Phe
145                 150                 155                 160

Pro Thr Gly Ile Lys Trp Lys Thr Val Leu Gly Ala Gln Ser Ala Val
                165                 170                 175

Lys Tyr Ile Val Cys Asn Ala Asp Glu Gly Asp Ser Gly Thr Phe Ser
            180                 185                 190

Asp Arg Met Val Met Glu Asp Asp Pro Phe Met Leu Ile Glu Gly Met
        195                 200                 205

Thr Ile Ala Ala Leu Ala Val Gly Ala Glu Gln Gly Tyr Ile Tyr Cys
    210                 215                 220

Arg Ser Glu Tyr Pro His Ala Ile Ala Val Leu Glu Ser Ala Ile Gly
225                 230                 235                 240

Ile Ala Asn Ala Ala Gly Trp Leu Gly Asp Asp Ile Arg Gly Ser Gly
                245                 250                 255

Lys Arg Phe His Leu Glu Val Arg Lys Gly Ala Gly Ala Tyr Val Cys
            260                 265                 270

Gly Glu Glu Thr Ala Leu Leu Glu Ser Leu Glu Gly Arg Arg Gly Val
        275                 280                 285

Val Arg Ala Lys Pro Pro Leu Pro Ala Leu Gln Gly Leu Phe Gly Lys
    290                 295                 300

Pro Thr Val Ile Asn Asn Val Ile Ser Leu Ala Thr Val Ala Gly Glu
305                 310                 315                 320

Ser Trp Arg Ala Ala Glu Tyr Tyr Arg Asp Tyr Gly Met Gly Arg Ser
                325                 330                 335

Arg Gly Thr Leu Pro Phe Gln Leu Ala Gly Asn Ile Lys Gln Gly Gly
            340                 345                 350

Leu Val Glu Lys Ala Phe Gly Val Thr Leu Arg Glu Leu Leu Val Asp
        355                 360                 365

Tyr Gly Gly Gly Thr Arg Ser Gly Arg Ala Ile Arg Ala Val Gln Val
    370                 375                 380

Gly Gly Pro Leu Gly Ala Tyr Leu Pro Glu Ser Arg Phe Asp Val Pro
385                 390                 395                 400

Leu Asp Tyr Glu Ala Tyr Ala Ala Phe Gly Gly Val Val Gly His Gly
                405                 410                 415

Gly Ile Val Val Phe Asp Glu Thr Val Asp Met Ala Lys Ala Gly Pro
            420                 425                 430

Tyr Ala Met Glu Phe Cys Ala Ile Glu Ser Cys Gly Lys Cys Thr Pro
        435                 440                 445

Cys Arg Ile Gly Ser Thr Arg Gly Val Glu Val Met Asp Arg Ile Ile
    450                 455                 460

Ala Gly Glu Gln Pro Val Lys His Val Ala Leu Val Arg Asp Leu Cys
465                 470                 475                 480
```

```
Asp Thr Met Leu Asn Gly Ser Leu Cys Ala Met Gly Gly Met Thr Pro
                485                 490                 495

Tyr Pro Val Leu Ser Ala Leu Asn Glu Phe Pro Glu Asp Phe Gly Leu
            500                 505                 510

Ala Ser Asn Pro Ala Lys Ala Ala
        515                 520


<210> SEQ ID NO 7
<211> LENGTH: 176
<212> TYPE: PRT
<213> ORGANISM: Ralstonia eutropha

<400> SEQUENCE: 7

Met Pro Glu Ile Ser Pro His Ala Pro Ala Ser Ala Asp Ala Thr Arg
1               5                   10                  15

Ile Ala Ala Ile Val Ala Ala Arg Gln Asp Ile Pro Gly Ala Leu Leu
            20                  25                  30

Pro Ile Leu His Glu Ile Gln Asp Thr Gln Gly Tyr Ile Pro Asp Ala
        35                  40                  45

Ala Val Pro Val Ile Ala Arg Ala Leu Asn Leu Ser Arg Ala Asp Val
    50                  55                  60

His Gly Val Ile Thr Phe Tyr His His Phe Arg Gln Gln Pro Ala Gly
65                  70                  75                  80

Arg His Val Val Gln Val Cys Arg Ala Glu Ala Cys Gln Ser Val Gly
                85                  90                  95

Ala Glu Ala Leu Ala Glu His Ala Gln Arg Ala Leu Gly Cys Gly Phe
            100                 105                 110

His Glu Thr Thr Ala Asp Gly Gln Val Thr Leu Glu Pro Val Tyr Cys
        115                 120                 125

Leu Gly Gln Cys Ala Cys Gly Pro Ala Val Met Val Gly Glu Gln Leu
    130                 135                 140

His Gly Tyr Val Asp Ala Arg Arg Phe Asp Ala Leu Val Arg Ser Leu
145                 150                 155                 160

Arg Glu Ser Ser Ala Glu Lys Thr Thr Glu Ala Ala Glu Ala Gln Ala
                165                 170                 175


<210> SEQ ID NO 8
<211> LENGTH: 292
<212> TYPE: PRT
<213> ORGANISM: Pyrococcus furiosus

<400> SEQUENCE: 8

Met Met Leu Pro Lys Glu Ile Met Met Pro Asn Asp Asn Pro Tyr Ala
1               5                   10                  15

Leu His Arg Val Lys Val Leu Lys Val Tyr Ser Leu Thr Glu Thr Glu
            20                  25                  30

Lys Leu Phe Leu Phe Arg Phe Glu Asp Pro Glu Leu Ala Glu Lys Trp
        35                  40                  45

Thr Phe Lys Pro Gly Gln Phe Val Gln Leu Thr Ile Pro Gly Val Gly
    50                  55                  60

Glu Val Pro Ile Ser Ile Cys Ser Ser Pro Met Arg Lys Gly Phe Phe
65                  70                  75                  80

Glu Leu Cys Ile Arg Lys Ala Gly Arg Val Thr Thr Val Val His Arg
                85                  90                  95

Leu Lys Pro Gly Asp Thr Val Leu Val Arg Gly Pro Tyr Gly Asn Gly
            100                 105                 110
```

```
Phe Pro Val Asp Glu Trp Glu Gly Met Asp Leu Leu Leu Ile Ala Ala
        115                 120                 125

Gly Leu Gly Thr Ala Pro Leu Arg Ser Val Phe Leu Tyr Ala Met Asp
    130                 135                 140

Asn Arg Trp Lys Tyr Gly Asn Ile Thr Phe Ile Asn Thr Ala Arg Tyr
145                 150                 155                 160

Gly Lys Asp Leu Leu Phe Tyr Lys Glu Leu Glu Ala Met Lys Asp Leu
                165                 170                 175

Ala Glu Ala Glu Asn Val Lys Ile Ile Gln Ser Val Thr Arg Asp Pro
            180                 185                 190

Asn Trp Pro Gly Leu Lys Gly Arg Pro Gln Gln Phe Ile Val Glu Ala
        195                 200                 205

Asn Thr Asn Pro Lys Asn Thr Ala Val Ala Ile Cys Gly Pro Pro Arg
    210                 215                 220

Met Tyr Lys Ser Val Phe Glu Ala Leu Ile Asn Tyr Gly Tyr Arg Pro
225                 230                 235                 240

Glu Asn Ile Phe Val Thr Leu Glu Arg Arg Met Lys Cys Gly Ile Gly
                245                 250                 255

Lys Cys Gly His Cys Asn Val Gly Thr Ser Thr Ser Trp Lys Tyr Ile
            260                 265                 270

Cys Lys Asp Gly Pro Val Phe Thr Tyr Phe Asp Ile Val Ser Thr Pro
        275                 280                 285

Gly Leu Leu Asp
    290
```

<210> SEQ ID NO 9
<211> LENGTH: 367
<212> TYPE: PRT
<213> ORGANISM: Pyrococcus furiosus

<400> SEQUENCE: 9

```
Met Arg Tyr Val Lys Leu Pro Lys Glu Asn Thr Tyr Glu Phe Leu Glu
1               5                   10                  15

Arg Leu Lys Asp Trp Gly Lys Leu Tyr Ala Pro Val Lys Ile Ser Asp
            20                  25                  30

Lys Phe Tyr Asp Phe Arg Glu Ile Asp Asp Val Arg Lys Ile Glu Phe
        35                  40                  45

His Tyr Asn Arg Thr Ile Met Pro Pro Lys Lys Phe Phe Phe Lys Pro
    50                  55                  60

Arg Glu Lys Leu Phe Glu Phe Asp Ile Ser Lys Pro Glu Tyr Arg Glu
65                  70                  75                  80

Val Ile Glu Glu Val Glu Pro Phe Ile Ile Phe Gly Val His Ala Cys
                85                  90                  95

Asp Ile Tyr Gly Leu Lys Ile Leu Asp Thr Val Tyr Leu Asp Glu Phe
            100                 105                 110

Pro Asp Lys Tyr Tyr Lys Val Arg Arg Glu Lys Gly Ile Ile Ile Gly
        115                 120                 125

Ile Ser Cys Met Pro Asp Glu Tyr Cys Phe Cys Asn Leu Arg Glu Thr
    130                 135                 140

Asp Phe Ala Asp Asp Gly Phe Asp Leu Phe Phe His Glu Leu Pro Asp
145                 150                 155                 160

Gly Trp Leu Val Arg Val Gly Thr Pro Thr Gly His Arg Leu Val Asp
                165                 170                 175

Lys Asn Ile Lys Leu Phe Glu Glu Val Thr Asp Lys Asp Ile Cys Ala
```

```
            180                 185                 190

Phe Arg Asp Phe Glu Lys Arg Arg Gln Gln Ala Phe Lys Tyr His Glu
        195                 200                 205

Asp Trp Gly Asn Leu Arg Tyr Leu Leu Glu Leu Glu Met Glu His Pro
    210                 215                 220

Met Trp Asp Glu Glu Ala Asp Lys Cys Leu Ala Cys Gly Ile Cys Asn
225                 230                 235                 240

Thr Thr Cys Pro Thr Cys Arg Cys Tyr Glu Val Gln Asp Ile Val Asn
                245                 250                 255

Leu Asp Gly Val Thr Gly Tyr Arg Glu Arg Arg Trp Asp Ser Cys Gln
            260                 265                 270

Phe Arg Ser His Gly Leu Val Ala Gly Gly His Asn Phe Arg Pro Thr
        275                 280                 285

Lys Lys Asp Arg Phe Arg Asn Arg Tyr Leu Cys Lys Asn Ala Tyr Asn
    290                 295                 300

Glu Lys Leu Gly Leu Ser Tyr Cys Val Gly Cys Gly Arg Cys Thr Ala
305                 310                 315                 320

Phe Cys Pro Ala Asn Ile Ser Phe Val Gly Asn Leu Arg Arg Ile Leu
                325                 330                 335

Gly Leu Glu Glu Asn Lys Cys Pro Pro Thr Val Ser Glu Glu Ile Pro
            340                 345                 350

Lys Arg Gly Phe Ala Tyr Ser Ser Asn Ile Arg Gly Asp Gly Val
        355                 360                 365


<210> SEQ ID NO 10
<211> LENGTH: 288
<212> TYPE: PRT
<213> ORGANISM: Pyrococcus furiosus

<400> SEQUENCE: 10

Met Asn Pro Tyr Arg Ser Tyr Asp Ala Arg Ile Ile Glu Val Lys Glu
1               5                   10                  15

Leu Thr Ser Arg Glu Lys Leu Phe Ser Leu Lys Phe Leu Asp Asn Glu
            20                  25                  30

Ile Glu Glu Asn Phe Thr Phe Lys Pro Gly Gln Phe Val Ile Val Asp
        35                  40                  45

Ile Arg Gly Phe Gly Glu Phe Pro Ile Ser Leu Cys Ser Ser Pro Thr
    50                  55                  60

Arg Arg Pro Ile Gln Leu Cys Ile Arg Arg Val Gly Arg Met Thr Lys
65                  70                  75                  80

Phe Ile His Lys Met Asn Glu Gly Asp Ile Ile Gly Ile Arg Gly Pro
                85                  90                  95

Tyr Gly Asn Gly Phe Pro Met Asp Leu Met Glu Gly Ser Asn Leu Ile
            100                 105                 110

Leu Ile Ala Gly Gly Leu Gly Met Ala Pro Leu Arg Ser Val Leu Trp
        115                 120                 125

Tyr Ala Ile Asp Ser Gly Lys Tyr Glu Lys Ile Tyr Leu Phe Tyr Gly
    130                 135                 140

Thr Lys Ser Tyr Glu Asp Ile Leu Phe Arg Asp Glu Ile Ile His Leu
145                 150                 155                 160

Leu Lys His Gly Glu Lys Leu Asn Cys His Val Lys Leu Ala Tyr Glu
                165                 170                 175

Val Glu Thr Pro Ser Cys Ile Tyr Leu Glu Arg Gly Phe Ser Glu Lys
            180                 185                 190
```

```
Val Cys Lys Gly Val Val Thr Asp Leu Phe Arg Gly Glu Glu Phe Asp
        195                 200                 205

Val Glu Asn Ser Tyr Ala Leu Ile Cys Gly Pro Pro Val Met Tyr Lys
    210                 215                 220

Tyr Val Ile Arg Glu Leu Leu Asp Arg Gly Leu Ser Pro Gly Arg Ile
225                 230                 235                 240

Tyr Met Thr Leu Glu Arg Arg Met Arg Cys Gly Val Gly Lys Cys Gly
                245                 250                 255

His Cys Ile Val Gly Thr Ser Val Ser Ile Lys Tyr Ile Cys Lys Asp
            260                 265                 270

Gly Pro Val Phe Thr Tyr Trp Asp Ala Leu Ser Thr Arg Gly Leu Ile
        275                 280                 285


<210> SEQ ID NO 11
<211> LENGTH: 334
<212> TYPE: PRT
<213> ORGANISM: Pyrococcus furiosus

<400> SEQUENCE: 11

Met Arg Tyr Val Lys Leu His Ser Glu Tyr Phe Pro Glu Phe Phe Asn
1               5                   10                  15

Arg Leu Lys Glu Val Gly Arg Val Tyr Gly Pro Val Arg His Asn Ser
            20                  25                  30

Thr Tyr Arg Phe Glu Glu Val Asn Ser Ile Asp Glu Leu Ser Leu Asp
        35                  40                  45

Tyr Thr Arg Thr Ile Leu Pro Pro Lys Lys Phe Phe Ile Arg Pro Arg
    50                  55                  60

Asp Ala Met Phe Lys Ile Gln Lys Asn Glu Val Thr Glu Val Asp Gly
65                  70                  75                  80

Asp Gly Lys Phe Val Leu Phe Gly Val His Ser Cys Asp Ile His Gly
                85                  90                  95

Ile Lys Ile Leu Asp Lys Val Tyr Leu Ser Asn Pro Pro Asp Pro Tyr
            100                 105                 110

Tyr Glu Arg Arg Arg Lys Asn Ala Phe Ile Val Gly Ile Ser Cys Met
        115                 120                 125

Pro Asp Glu Tyr Cys Phe Cys Lys Ser Leu Gly Thr Asp Phe Ala Met
    130                 135                 140

Asp Gly Phe Asp Ile Phe Leu His Glu Leu Pro Asp Gly Trp Leu Val
145                 150                 155                 160

Arg Val Gly Ser Val Lys Gly His Glu Phe Val Trp Glu Asn Gln Asp
                165                 170                 175

Ile Phe Asp Asp Val Thr Glu Glu Asp Leu Arg Asn Phe Lys Glu Phe
            180                 185                 190

Glu Glu Lys Arg Ala Lys Ala Phe Lys Lys Ser Leu Asn Lys Glu Gly
        195                 200                 205

Leu Ala Asp Ile Leu Asp Leu Ala Phe Thr Ser Lys Val Trp Lys Lys
    210                 215                 220

Tyr Ala Glu Lys Cys Leu Gly Cys Gly Asn Cys Thr Ile Val Cys Pro
225                 230                 235                 240

Thr Cys Arg Cys Tyr Glu Val Cys Asp Thr Trp Val Arg Ala Tyr Glu
                245                 250                 255

Ala Leu Arg Met Arg Arg Tyr Asp Ser Cys Phe Met Pro Thr His Gly
            260                 265                 270

Leu Val Ala Gly Gly His Asn Phe Arg Pro Thr Arg Leu Asp Arg Phe
        275                 280                 285
```

Arg His Arg Tyr Tyr Cys Lys Asn Tyr Phe Asp Pro Glu Ala Gly Phe
    290                 295                 300

Asn Cys Val Gly Cys Gly Arg Cys Asp Glu Phe Cys Pro Ala Arg Ile
305                 310                 315                 320

Glu His Val Lys Val Leu Asp Glu Val Arg Glu Gly Leu Ile
                325                 330

<210> SEQ ID NO 12
<211> LENGTH: 604
<212> TYPE: PRT
<213> ORGANISM: Rhodococcus opacus

<400> SEQUENCE: 12

Met Ser Gly Asp Ile Lys Ala Ile Leu Glu Arg Asn Gly Ser Glu Arg
1               5                   10                  15

Thr Arg Leu Ile Asp Ile Leu Trp Asp Val Gln His Leu Tyr Gly His
            20                  25                  30

Ile Pro Asp Glu Val Leu Pro Gln Leu Ala Asp Glu Leu Asn Leu Ser
        35                  40                  45

Pro Leu Asp Ile Leu Glu Thr Ala Ser Phe Tyr His Phe Phe His Arg
    50                  55                  60

Lys Pro Ser Gly Lys Tyr Arg Ile Tyr Leu Ser Asp Thr Val Ile Ala
65                  70                  75                  80

Lys Met Asn Gly Tyr Gln Ala Val His Asp Ser Leu Glu Arg Glu Thr
                85                  90                  95

Gly Ala Arg Phe Gly Gly Thr Asp Lys Thr Gly Met Phe Gly Leu Phe
            100                 105                 110

Glu Thr Pro Cys Ile Gly Leu Ser Asp Gln Glu Pro Ala Met Leu Ile
        115                 120                 125

Asp Asn Val Val Phe Thr Arg Leu Arg Pro Gly Thr Ile Val Asp Ile
    130                 135                 140

Ile Thr Gln Leu Arg Gln Gly Arg Ser Pro Glu Asp Ile Ala Asn Pro
145                 150                 155                 160

Ala Gly Leu Pro Ser Asp Asp Val Ala Tyr Val Asp Gly Val Val Glu
                165                 170                 175

Ser Asn Val Arg Thr Lys Gly Pro Val Phe Phe Arg Gly Leu Thr Asp
            180                 185                 190

Tyr Gly Arg Leu Leu Glu Leu Cys Leu Ala Leu Arg Pro Glu Gln Ile
        195                 200                 205

Ile Asp Arg Ile Ile Glu Ser Lys Leu Arg Gly Arg Gly Gly Ala Gly
    210                 215                 220

Phe Ser Thr Gly Leu Lys Trp Gln Leu Cys Arg Thr Ala Val Ser Asp
225                 230                 235                 240

Asp Lys Tyr Ile Ile Cys Asn Ala Asp Glu Gly Glu Pro Gly Thr Phe
                245                 250                 255

Lys Asp Arg Val Leu Leu Thr Arg Ser Pro Lys Lys Val Phe Met Gly
            260                 265                 270

Met Ile Ile Ala Ala Arg Ala Ile Gly Ser Arg Asn Gly Ile Leu Tyr
        275                 280                 285

Leu Arg Trp Glu Tyr Ile Tyr Leu Lys Asp Tyr Leu Glu Arg Gln Leu
    290                 295                 300

Gln Glu Leu Arg Asp Glu Gly Leu Leu Gly Ala Arg Ile Gly Gly Gln
305                 310                 315                 320

Ser Gly Phe Asp Phe Asp Ile Arg Ile Gln Met Gly Ala Gly Ala Tyr

```
                325                 330                 335

Ile Cys Gly Asp Glu Ser Ala Leu Ile Glu Ser Cys Glu Gly Lys Arg
            340                 345                 350

Gly Thr Pro Arg Val Lys Pro Pro Phe Pro Val Gln Glu Gly Tyr Leu
        355                 360                 365

Gly Lys Pro Thr Cys Val Asn Asn Val Glu Thr Phe Ala Ala Ala Ala
    370                 375                 380

Arg Ile Met Glu Glu Gly Pro Asn Trp Phe Arg Ala Leu Gly Thr Pro
385                 390                 395                 400

Glu Ser Thr Gly Thr Arg Leu Leu Ser Val Ala Gly Asp Cys Ser Arg
                405                 410                 415

Pro Gly Ile Tyr Glu Val Glu Trp Gly Val Thr Leu Asn Glu Val Leu
            420                 425                 430

Thr Thr Val Gly Ala Arg Asp Ala Arg Ala Val Gln Ile Ser Gly Pro
        435                 440                 445

Ser Gly Gln Cys Val Ser Val Ala Glu Asp Gly Glu Arg Arg Met Ala
    450                 455                 460

Tyr Glu Asp Ile Ser Cys Asn Gly Ala Phe Thr Ile Phe Asn Thr Glu
465                 470                 475                 480

Arg Asp Leu Leu Glu Ile Val Lys Asp Phe Met Gln Phe Phe Val Asp
                485                 490                 495

Glu Ser Cys Gly Ile Cys Val Pro Cys Arg Val Gly Asn Ile Asp Leu
            500                 505                 510

His Lys Lys Val Glu Leu Val Ile Ala Gly Lys Ala Cys Gln Lys Asp
        515                 520                 525

Leu Asp Asp Val Val Ser Trp Gly Ala Leu Val Lys Lys Thr Ser Arg
    530                 535                 540

Cys Gly Leu Gly Ala Thr Ser Pro Asn Pro Ile Leu Thr Thr Leu Asp
545                 550                 555                 560

Lys Phe Pro Glu Ile Tyr Thr Lys Arg Leu Arg Lys Gln Lys Lys Glu
                565                 570                 575

Ala Leu Leu Leu Ser Phe Asp Leu Asp Ala Ala Leu Gly Gly Tyr Glu
            580                 585                 590

Lys Ala Leu Glu Gly Leu Ala Lys Glu Glu Ile Lys
        595                 600


<210> SEQ ID NO 13
<211> LENGTH: 234
<212> TYPE: PRT
<213> ORGANISM: Rhodococcus opacus

<400> SEQUENCE: 13

Met Ser Ile Glu Ile Glu Ile Asp Gly Val Thr Val Thr Thr Glu Glu
1               5                   10                  15

Ser Arg Thr Leu Val Asp Val Ala Ala Glu Ala Gly Val Tyr Ile Pro
            20                  25                  30

Thr Leu Cys Tyr Leu Lys Gly Lys Pro Ser Leu Gly Thr Cys Arg Val
        35                  40                  45

Cys Ser Val Lys Leu Asn Gly Thr Val Val Ala Ala Cys Thr Ile Arg
    50                  55                  60

Val Ala Asn Gly Met Lys Ile Glu Val Asp Glu Pro Glu Val Val Asp
65                  70                  75                  80

Met Arg Lys Ala Asn Val Glu Leu Leu Phe Ala Glu Gly Asn His Asn
                85                  90                  95
```

-continued

```
Cys Pro Ser Cys Glu Lys Ser Gly Arg Cys Lys Leu Gln Ala Val Gly
            100                 105                 110

Tyr Glu Val Asp Met Met Val Ser Arg Phe Gln Tyr Arg Phe Pro Glu
        115                 120                 125

Arg Val Gln Asp His Ala Ser Glu Thr Ile Trp Leu Glu Arg Asp Arg
    130                 135                 140

Cys Ile Phe Cys Gln Arg Cys Val Glu Phe Val Arg Asp Lys Ala Thr
145                 150                 155                 160

Gly Lys Lys Ile Phe Ser Ile Ser Asn Arg Gly Gly Asp Ser Arg Ile
                165                 170                 175

Glu Ile Asp Ala Asp Leu Ala Asn Ala Met Pro Pro Glu Gln Val Arg
            180                 185                 190

Glu Ala Val Ala Ile Cys Pro Val Gly Thr Ile Ile Glu Lys Arg Val
        195                 200                 205

Gly Tyr Asp Asp Pro Ile Gly Arg Arg Lys Tyr Glu Ile Glu Thr Val
    210                 215                 220

Arg Ala Arg Ala Leu Gly Gly Glu Glu Glu
225                 230


<210> SEQ ID NO 14
<211> LENGTH: 538
<212> TYPE: PRT
<213> ORGANISM: Allochromatium vinosum

<400> SEQUENCE: 14

Met His Leu Glu Asp Leu Ala Glu Gln Ala Ala Gln Tyr Arg Asn Glu
1               5                   10                  15

Asp Ala His Ile Glu Arg Glu Val Arg Val Cys Val Ala Ala Ser Cys
            20                  25                  30

Gln Ser Ala Ala Ala Val Pro Val Leu Glu Ala Leu Lys Ser Ala Cys
        35                  40                  45

Asp Thr Gln Gly Ala Gly Ser Cys Lys Val Lys Gly Val Gly Cys Met
    50                  55                  60

Gly Leu Cys Ser Ala Gly Pro Leu Val Ala Val Ala Asp Lys Asp Cys
65                  70                  75                  80

Ala Leu Asn Glu Ser Ala Leu Tyr Arg Asp Val Thr Pro Asp Asp Ala
                85                  90                  95

Pro Asp Ile Met Ala Ser Val Cys Ser Thr Pro Val Glu Arg Leu Arg
            100                 105                 110

Cys Pro Thr Asp Gln Pro Phe Phe Ser Arg Gln Gln Arg Ile Val Leu
        115                 120                 125

Glu His Ser Gly Leu Ile Asp Pro Asp Ser Leu Arg Gly Tyr Ile Ala
    130                 135                 140

Val Gly Gly Tyr Ala Ala Leu Val Arg Ala Leu Thr Glu Met Thr Pro
145                 150                 155                 160

Ala Asp Val Leu Arg Glu Val Thr Thr Ser Gly Leu Arg Gly Arg Gly
                165                 170                 175

Gly Gly Gly Tyr Pro Thr Gly Leu Lys Trp Ser Thr Ile Ala Lys Met
            180                 185                 190

Pro Pro Gly Gln Lys Tyr Val Val Cys Asn Ala Asp Glu Gly Asp Pro
        195                 200                 205

Gly Ala Phe Met Asp Arg Ala Val Leu Glu Ser Asp Pro His Arg Val
    210                 215                 220

Leu Glu Gly Met Ala Ile Ala Ala Tyr Ala Val Gly Ala Ser Lys Gly
225                 230                 235                 240
```

```
Tyr Val Tyr Val Arg Ala Glu Tyr Pro Leu Ala Val Glu Arg Leu Glu
                245                 250                 255

Thr Ala Ile Arg Lys Ala Lys Arg Ala Gly Phe Leu Gly Ala Lys Val
            260                 265                 270

Ala Asp Thr Gln Phe Ala Phe Glu Val Glu Ile Arg Leu Gly Ala Gly
        275                 280                 285

Ala Phe Val Cys Gly Glu Glu Thr Ala Leu Met Ala Ser Ile Glu Gly
    290                 295                 300

Leu Arg Gly Gln Pro Arg Pro Arg Pro Pro Tyr Pro Ala Glu Ser Gly
305                 310                 315                 320

Leu Trp Gly Cys Pro Thr Leu Ile Asn Asn Val Glu Thr Phe Ala Asn
                325                 330                 335

Ile Ala Pro Ile Ile Arg Glu Gly Gly Asp Trp Phe Ala Ala Ile Gly
            340                 345                 350

Thr Glu Gly Ser Lys Gly Thr Lys Val Phe Ala Leu Ala Gly Lys Ile
        355                 360                 365

Lys Asn Thr Gly Leu Ile Glu Val Pro Met Gly Thr Ser Leu Arg Asp
    370                 375                 380

Ile Ile Glu Val Ile Gly Gly Gly Ile Pro Asp Gly Arg Ala Phe Lys
385                 390                 395                 400

Ala Val Gln Thr Gly Gly Pro Ser Gly Gly Cys Ile Pro Arg Arg His
                405                 410                 415

Leu Asp Ile Pro Val Asp Tyr Asp Ser Leu Lys Thr Leu Gly Thr Ile
            420                 425                 430

Met Gly Ser Gly Gly Leu Ile Val Met Asp Glu Thr Ser Cys Met Val
        435                 440                 445

Asp Val Ala Arg Phe Met Glu Phe Cys Met Ser Glu Ser Cys Gly Lys
    450                 455                 460

Cys Ile Pro Cys Arg Ala Gly Thr Trp Gln Met His Ala Leu Leu Asp
465                 470                 475                 480

Thr Leu Thr Lys Ala Glu Gly Thr Arg Ala Asp Leu Ala Leu Leu Glu
                485                 490                 495

Asp Leu Cys Asp Val Val Arg Ala Thr Ser Leu Cys Gly Leu Gly Gln
            500                 505                 510

Thr Ala Pro Asn Pro Val Leu Ser Thr Leu Arg Tyr Phe Arg Asp Glu
        515                 520                 525

Tyr Glu Ala Lys Leu Gly Trp Glu Thr Ala
    530                 535


<210> SEQ ID NO 15
<211> LENGTH: 243
<212> TYPE: PRT
<213> ORGANISM: Allochromatium vinosum

<400> SEQUENCE: 15

Met Pro Leu Pro Thr Pro Gln Pro Asn Val Arg Val Val Thr Leu Arg
1               5                   10                  15

Ile Asp Asp Arg Asp Leu Ser Ala Arg Glu Asp Glu Thr Leu Ile Glu
            20                  25                  30

Val Cys Arg Glu Asn Arg Ile Pro Ile Pro Ser Leu Cys His Leu Asp
        35                  40                  45

Gly Leu Ser Val Trp Gly Gly Cys Arg Leu Cys Met Val Glu Ile Ala
    50                  55                  60

Gly Gln Gly Arg Leu Val Ala Ala Cys Ser Thr Arg Val Ala Glu Gly
```

65 70 75 80

Met Thr Val Gln Thr Asp Thr Glu Arg Leu Arg His Tyr Arg Arg Thr
85 90 95

Ile Val Glu Leu Leu Phe Ala Glu Arg Asn His Val Cys Ser Val Cys
100 105 110

Val Ser Asn Gly His Cys Glu Leu Gln Ser Leu Ala Gln Arg Cys Gly
115 120 125

Val Asp His Val Arg Leu Pro Tyr Arg Gln Ala Pro Tyr Pro Val Asp
130 135 140

Ser Ser His Glu Met Phe Arg Leu Asp His Asn Arg Cys Ile Leu Cys
145 150 155 160

Thr Arg Cys Val Arg Val Cys Asp Glu Ile Glu Gly Ala His Thr Trp
165 170 175

Asp Val Met Gly Arg Gly Ser Asp Cys Arg Val Ile Thr Asp Met Ala
180 185 190

Arg Pro Trp Gly Glu Ser Glu Thr Cys Thr Ser Cys Gly Lys Cys Val
195 200 205

Gln Val Cys Pro Thr Gly Ala Leu Val Lys Gln Gly Thr Ser Ala Gly
210 215 220

Glu Met Val Lys Asp Gln His Phe Leu Pro Ile Leu Ala Arg Arg Arg
225 230 235 240

His Ala Arg

<210> SEQ ID NO 16
<211> LENGTH: 536
<212> TYPE: PRT
<213> ORGANISM: Thiocapsa roseopersicina

<400> SEQUENCE: 16

Met Asn Leu Asp Asp Leu Thr Asp Leu Ala Glu Lys Tyr Arg Glu Ala
1 5 10 15

Glu Ala Gly Val Asp Arg Glu Val Arg Val Cys Leu Ala Ala Ser Cys
20 25 30

Gln Ser Ser Gly Ala Val Pro Val Phe Asp Ala Leu Val Ala Glu Leu
35 40 45

Gly Asp Thr Lys Pro Ser Cys Lys Val Lys Gly Val Gly Cys Met Gly
50 55 60

Leu Cys Ser Ala Gly Pro Leu Val Ala Val Ala Asp Arg Glu Ala Asp
65 70 75 80

Leu Gln Gly Ser Val Leu Tyr Arg Asp Val Thr Ala Asp Asp Ala Glu
85 90 95

Asp Ile Val Ala Ser Ile Asp Gly Pro Pro Val Glu Arg Leu Arg Cys
100 105 110

Pro Thr Asn Gln Pro Phe Phe Ala Arg Gln Gln Lys Ile Val Leu Glu
115 120 125

Asn Ala Gly Ile Ile Asp Pro Asp Ser Phe Lys Gly Tyr Val Ala Val
130 135 140

Gly Gly Tyr Ser Ala Leu Ile Arg Ala Leu Ser Glu Met Thr Pro Ala
145 150 155 160

Asp Val Leu Arg Glu Val Thr Asp Ser Gly Leu Arg Gly Arg Gly Gly
165 170 175

Gly Gly Tyr Pro Thr Gly Leu Lys Trp Ser Thr Val Ala Lys Met Pro
180 185 190

Ala Thr Gln Lys Tyr Val Ile Cys Asn Ala Asp Glu Gly Asp Pro Gly

```
        195                 200                 205

Ala Phe Met Asp Arg Ala Ile Leu Glu Ser Asp Pro His Arg Val Leu
    210                 215                 220

Glu Gly Met Ala Ile Ala Ala Tyr Ala Ile Gly Ala Asn Lys Ala Tyr
225                 230                 235                 240

Val Tyr Val Arg Ala Glu Tyr Pro Leu Ala Val Glu Arg Leu Gln Thr
                245                 250                 255

Ala Ile Arg Lys Ala Lys Arg Ser Gly Leu Leu Gly Asn Lys Ile Gly
            260                 265                 270

Asp Thr Gln Phe Ser Leu Glu Val Glu Ile Arg Leu Gly Ala Gly Ala
        275                 280                 285

Phe Val Cys Gly Glu Glu Thr Ala Leu Met Ala Ser Ile Glu Gly Leu
    290                 295                 300

Arg Gly Gln Pro Arg Pro Arg Pro Pro Tyr Pro Ala Glu Ala Gly Leu
305                 310                 315                 320

Trp Gly Tyr Pro Thr Leu Ile Asn Asn Val Glu Thr Phe Ala Asn Ile
                325                 330                 335

Ala Pro Ile Val Arg Glu Gly Gly Asp Trp Phe Ala Ser Ile Gly Thr
            340                 345                 350

Glu Arg Ser Lys Gly Thr Lys Val Phe Ala Leu Ala Gly Thr Ile Thr
        355                 360                 365

Asn Thr Gly Leu Ile Glu Val Pro Met Gly Thr Ser Leu Arg Asp Ile
    370                 375                 380

Ile Glu Val Ile Gly Gly Gly Ile Pro Gly Gly Lys Ala Phe Lys Ala
385                 390                 395                 400

Val Gln Thr Gly Gly Pro Ser Gly Gly Cys Ile Pro Ala Gln His Leu
                405                 410                 415

Asp Ile Ala Val Asp Tyr Asp Ser Leu Lys Thr Leu Gly Thr Met Met
            420                 425                 430

Gly Ser Gly Gly Met Ile Val Met Asp Glu Thr Ser Ser Met Val Asp
        435                 440                 445

Val Ala Arg Tyr Phe Met Glu Phe Cys Met Thr Glu Ser Cys Gly Lys
    450                 455                 460

Cys Ile Pro Cys Arg Thr Gly Thr Gln Gln Met His Ser Ile Leu Asp
465                 470                 475                 480

Arg Leu Ala Lys Ser Gln Ala Thr Arg Ala Glu Leu Thr Leu Leu Glu
                485                 490                 495

Glu Leu Cys Glu Val Val Gln Ala Thr Ser Leu Cys Gly Leu Gly Gln
            500                 505                 510

Thr Ala Pro Asn Pro Val Leu Ser Thr Met Arg Tyr Phe Arg Asp Glu
        515                 520                 525

Tyr Glu Ala Lys Leu Gly Glu Val
    530                 535


<210> SEQ ID NO 17
<211> LENGTH: 243
<212> TYPE: PRT
<213> ORGANISM: Thiocapsa roseopersicina

<400> SEQUENCE: 17

Met Pro Leu Pro Ala Lys Gln Pro Asn Val Arg Val Val Thr Leu Asn
1               5                   10                  15

Ile Asp Gly Arg Asp Leu Ser Ala Arg Glu Asp Glu Thr Ile Ile Glu
            20                  25                  30
```

Val Cys Arg Glu Asn Gln Ile Pro Ile Pro Ser Leu Cys Tyr Leu Glu
35 40 45

Gly Leu Ser Val Trp Gly Ala Cys Arg Leu Cys Leu Val Glu Leu Ser
50 55 60

Gly Gln Gly Arg Leu Leu Ala Ala Cys Ser Thr Arg Val Thr Glu Gly
65 70 75 80

Met Gln Ile Gln Thr Asn Thr Glu Lys Leu Gln Arg Tyr Arg Arg Thr
85 90 95

Ile Val Glu Leu Leu Phe Ala Glu Arg Asn His Val Cys Ser Val Cys
100 105 110

Val Ser Asn Gly His Cys Glu Leu Gln His Met Ala Gln Lys Cys Gly
115 120 125

Val Asp His Val Arg Val Pro Tyr Arg Gln Ala Ser Tyr Pro Val Asp
130 135 140

Ser Ser His Glu Met Phe Arg Leu Asp His Asp Arg Cys Ile Leu Cys
145 150 155 160

Thr Arg Cys Val Arg Val Cys Asp Glu Ile Glu Gly Ala His Thr Trp
165 170 175

Asp Val Met Gly Arg Gly Ser Asp Cys Arg Val Ile Thr Asp Met Ala
180 185 190

Gln Pro Trp Gly Glu Ser Asp Thr Cys Thr Ser Cys Gly Lys Cys Val
195 200 205

Gln Val Cys Pro Thr Gly Ala Leu Val Lys Gln Gly Thr Ser Val Gly
210 215 220

Glu Met Val Lys Asp Gln His Phe Leu Pro Ile Leu Ala Arg Arg Arg
225 230 235 240

His Ser Gln

<210> SEQ ID NO 18
<211> LENGTH: 610
<212> TYPE: PRT
<213> ORGANISM: Thiocapsa roseopersicina

<400> SEQUENCE: 18

Met Asn Ala Ser Ala Thr Val Thr Val Glu Gly Phe Val Ala Glu Ser
1 5 10 15

Leu Ala Thr His Gly Arg Asp Pro Arg His Leu Leu Gln His Leu Ile
20 25 30

Arg Val Gln Gln Arg Phe Ser Tyr Val Pro Asp Ala Ala Val Glu Ala
35 40 45

Leu Ser Val Ala Leu Asp Val Thr Arg Thr Gln Val Arg Ala Ala Ile
50 55 60

Ala Phe Tyr Ala Phe Leu His Asp Arg Pro Arg Gly Ala Phe Glu Ile
65 70 75 80

Arg Phe Ser Asp Asn Ile Thr Asp Arg Met Leu Gly Ser Arg Arg Leu
85 90 95

Ile Arg Leu Leu Ile Glu Arg Leu Gly Leu Thr Gly Leu Pro Ala Trp
100 105 110

Gly Arg Asp Leu Val Arg Pro Asp Gly Arg Ala Ser Val Gly Leu Ala
115 120 125

Ser Cys Thr Gly Met Cys Asp Gln Gly Pro Ala Leu Leu Val Asn Gly
130 135 140

Gln Ala Val Thr Asn Leu Asp Ala Gln Arg Val Asp Arg Ile Ala Asp
145 150 155 160

-continued

```
Leu Val Gln Glu Gly Ile Pro Leu Glu Arg Trp Pro Gly Glu Phe Phe
                165                 170                 175

Arg Val Glu Asn Asn Ile Arg Arg Arg Gly Leu Leu Leu Gly Asn Pro
            180                 185                 190

Ala Thr Asp Gly Ala Ala Val Arg Arg Leu Leu Asp Ala Gly Ala Glu
        195                 200                 205

Ala Ala Leu Ala Glu Val Glu Arg Ser Gly Leu Arg Gly Arg Gly Gly
    210                 215                 220

Ala Gly Phe Thr Thr Ala Leu Lys Trp Arg Phe Cys Arg Glu Ala Pro
225                 230                 235                 240

Gly Thr Asp Arg Tyr Val Val Cys Asn Ala Asp Glu Gly Glu Pro Gly
                245                 250                 255

Thr Phe Lys Asp Arg Val Leu Leu Thr Asp Tyr Thr Asp Leu Val Ile
            260                 265                 270

Glu Gly Met Thr Val Cys Ala Gly Val Ile Gly Ala Arg Arg Gly Phe
        275                 280                 285

Leu Tyr Leu Arg Gly Glu Tyr Arg Tyr Leu Leu Pro His Leu Glu Ser
    290                 295                 300

Val Leu Gln Arg Arg Arg Ala Glu Gly Leu Leu Gly Thr Arg Ile Leu
305                 310                 315                 320

Gly Ala Asp Gly Phe Asp Phe Asp Ile Glu Ile His Leu Gly Ala Gly
                325                 330                 335

Ala Tyr Ile Cys Gly Glu Glu Ser Ala Leu Ile Glu Ser Leu Glu Gly
            340                 345                 350

Lys Arg Gly Val Thr Arg Lys Arg Pro Pro Phe Pro Val Thr Ser Gly
        355                 360                 365

Phe Asp Asp Gln Pro Thr Val Val Asn Asn Val Glu Thr Phe Leu Ala
    370                 375                 380

Ala Ala Arg Val Val Gln Trp Gly Gly Tyr Trp Leu Arg Gly Glu Gly
385                 390                 395                 400

Thr Asp Gln Ser Ala Gly Ser Lys Ile Leu Ser Val Ser Gly Asp Cys
                405                 410                 415

Ala Arg Pro Gly Ile Tyr Glu Tyr Pro Phe Gly Thr Pro Val His Gln
            420                 425                 430

Val Leu Ser Asp Cys Gly Ala Glu Asn Thr Gln Ala Val Gln Ile Ser
        435                 440                 445

Gly Ala Ala Gly Ala Thr Leu Ser Pro Ala Asp Phe Asp Arg Ile Ile
    450                 455                 460

Ala Phe Glu Asp Leu Pro Thr Ala Gly Ser Phe Met Ile Phe Asp His
465                 470                 475                 480

Ser Arg Asp Leu Leu Asp Met Val Arg Asn Phe Ala Ala Phe Phe Ala
                485                 490                 495

His Glu Ser Cys Gly Phe Cys Thr Pro Cys Arg Val Gly Gly Ala Leu
            500                 505                 510

Leu Arg Asn Leu Val Glu Lys Val Ala Ala Gly Gln Gly Ser Glu Tyr
        515                 520                 525

Asp Leu Ser Glu Met Arg Arg Ile Gly Thr Val Met Arg Arg Ala Ser
    530                 535                 540

Tyr Cys Gly Leu Gly His Thr Ala Pro Asn His Val Val Asn Thr Leu
545                 550                 555                 560

Asp Lys Phe Pro Leu Ile Tyr Gly Arg Arg Leu Ala Arg Ala Ser His
                565                 570                 575

Thr Pro Ser Phe Asp Leu Asp Ala Ala Leu Ser Gln Ala Arg Ala Leu
```

580 585 590

Thr Gly Arg Asp Asp Ile Gly Ala His Ile Gly Asp Gly Ser Glu Val
595 600 605

Ser Ala
610

<210> SEQ ID NO 19
<211> LENGTH: 239
<212> TYPE: PRT
<213> ORGANISM: Thiocapsa roseopersicina

<400> SEQUENCE: 19

Met Ser Lys Thr Phe Lys Leu Asp Gly Arg Glu Ile Pro Phe Glu Thr
1 5 10 15

Gly Gln Thr Ile Met Asp Ala Ala Leu Ala Ala Gly Val Tyr Ile Pro
20 25 30

His Leu Cys His Asn Pro Glu Phe Ala Pro His Gly Ser Cys Arg Val
35 40 45

Cys Val Val Asp Ile Gly Gly Arg Gln Val Ser Ala Cys Thr Ala Ala
50 55 60

Ala Ser Glu Gly Leu Glu Val Asp Asn Ser Ser Glu Ala Ile Gln Glu
65 70 75 80

Thr Arg Arg Ala Ile Leu Gln Met Leu Phe Val Glu Gly Asn His Val
85 90 95

Cys Pro Ala Cys Glu Lys Ser Gly Ala Cys Gln Leu Gln Ala Val Ala
100 105 110

Tyr Tyr Thr Gly Met Leu Ala Pro His Phe Thr His Phe Phe Pro Arg
115 120 125

Arg Ser Val Asp Ala Ser His Pro Asp Val Val Ile Asp Phe Asn Arg
130 135 140

Cys Ile Leu Cys Glu Leu Cys Val Arg Ala Ser Arg Asp His Asp Gly
145 150 155 160

Lys Arg Val Phe Ala Ile Ser Gly Arg Gly Leu Glu Ser His Leu Val
165 170 175

Ile Asp Ser His Ser Gly Leu Leu Gly Asp Ser Ser Phe Ala Ala Thr
180 185 190

Asp Lys Ala Ala His Val Cys Pro Thr Gly Ala Ile Leu Pro Lys Gly
195 200 205

Arg Gly Tyr Glu Thr Pro Ile Gly Glu Arg Leu Tyr Asp Arg Glu Pro
210 215 220

Ile Ser Ile Val Gly Asp Val Arg Ala His Glu Glu Glu Val Val
225 230 235

<210> SEQ ID NO 20
<211> LENGTH: 533
<212> TYPE: PRT
<213> ORGANISM: Synechocystis PCC6803

<400> SEQUENCE: 20

Met Asp Ile Lys Glu Leu Lys Glu Ile Ala Thr Lys Ser Arg Glu Lys
1 5 10 15

Gln Thr Lys Ile Arg Ile Arg Cys Cys Ser Ala Ala Gly Cys Leu Ser
20 25 30

Ser Glu Gly Glu Thr Val Lys Lys Asn Leu Thr Thr Ala Ile Ala Ala
35 40 45

Ala Gly Leu Glu Glu Lys Val Glu Val Cys Gly Val Gly Cys Met Lys

```
    50                  55                  60

Phe Cys Gly Arg Gly Pro Leu Val Ala Val Asp Asp Arg Asn Gln Leu
65                  70                  75                  80

Tyr Glu Phe Val Thr Pro Asp Gln Val Gly Asp Ile Val Lys Lys Leu
                85                  90                  95

Gln Lys Pro Asp Ala Val Ala Glu Thr Gly Leu Ile Ser Gly Asp Pro
            100                 105                 110

His His Pro Phe Tyr Ala Leu Gln Arg Asn Ile Ala Leu Glu Asn Ser
        115                 120                 125

Gly Arg Ile Asp Pro Glu Ser Ile Asp Glu Tyr Ile Ala Leu Gly Gly
    130                 135                 140

Tyr Glu Gln Leu His Lys Val Val Tyr Glu Met Thr Pro Glu Glu Val
145                 150                 155                 160

Ile Val Glu Met Asn Lys Ser Gly Leu Arg Gly Arg Gly Gly Gly Gly
                165                 170                 175

Tyr Pro Thr Gly Leu Lys Trp Ala Thr Val Ala Lys Met Pro Gly Gln
            180                 185                 190

Gln Lys Tyr Val Ile Cys Asn Ala Asp Glu Gly Asp Pro Gly Ala Phe
        195                 200                 205

Met Asp Arg Ser Val Leu Glu Ser Asp Pro His Arg Ile Leu Glu Gly
    210                 215                 220

Met Ala Ile Ala Ala Tyr Ala Val Gly Ala Asn His Gly Tyr Ile Tyr
225                 230                 235                 240

Val Arg Ala Glu Tyr Pro Leu Ala Ile Gln Arg Leu Gln Lys Ala Ile
                245                 250                 255

Gln Gln Ala Lys Arg Tyr Gly Leu Met Gly Thr Gln Ile Phe Asp Ser
            260                 265                 270

Pro Ile Asp Phe Lys Ile Asp Ile Arg Val Gly Ala Gly Ala Phe Val
        275                 280                 285

Cys Gly Glu Glu Thr Ala Leu Ile Ala Ser Val Glu Gly Lys Arg Gly
    290                 295                 300

Thr Pro Arg Pro Arg Pro Pro Tyr Pro Ala Gln Ser Gly Leu Trp Gln
305                 310                 315                 320

Ser Pro Thr Leu Ile Asn Asn Val Glu Thr Tyr Ala Asn Val Val Pro
                325                 330                 335

Ile Ile Arg Glu Gly Gly Asp Trp Tyr Gly Ser Ile Gly Thr Glu Lys
            340                 345                 350

Ser Lys Gly Thr Lys Val Phe Ala Leu Thr Gly Lys Val Glu Asn Ala
        355                 360                 365

Gly Leu Ile Glu Val Pro Met Gly Thr Thr Val Arg Gln Val Val Glu
    370                 375                 380

Glu Met Gly Gly Gly Val Pro Asn Gly Gly Gln Val Lys Ala Val Gln
385                 390                 395                 400

Thr Gly Gly Pro Ser Gly Gly Cys Ile Pro Ala Asp Lys Leu Asp Thr
                405                 410                 415

Pro Ile Glu Tyr Asp Thr Leu Leu Ala Leu Gly Thr Met Met Gly Ser
            420                 425                 430

Gly Gly Met Ile Val Met Asp Glu Ser Thr Asn Met Val Asp Val Ala
        435                 440                 445

Gln Phe Tyr Met Asp Phe Cys Lys Ser Glu Ser Cys Gly Lys Cys Ile
    450                 455                 460

Pro Cys Arg Ala Gly Thr Val Gln Leu Tyr Asp Leu Leu Thr Arg Phe
465                 470                 475                 480
```

Leu Glu Gly Glu Ala Thr Gln Glu Asp Leu Ile Lys Leu Glu Asn Leu
485 490 495

Cys His Met Val Lys Glu Thr Ser Leu Cys Gly Leu Gly Met Ser Ala
500 505 510

Pro Asn Pro Val Ile Ser Thr Leu Arg Tyr Phe Arg His Glu Tyr Glu
515 520 525

Glu Leu Leu Lys Val
530

<210> SEQ ID NO 21
<211> LENGTH: 238
<212> TYPE: PRT
<213> ORGANISM: Synechocystis PCC6803

<400> SEQUENCE: 21

Met Ser Val Val Thr Leu Thr Ile Asp Asp Lys Ala Ile Ala Ile Glu
1 5 10 15

Glu Gly Ala Ser Ile Leu Gln Ala Ala Lys Glu Ala Gly Val Pro Ile
20 25 30

Pro Thr Leu Cys His Leu Glu Gly Ile Ser Glu Ala Ala Ala Cys Arg
35 40 45

Leu Cys Met Val Glu Val Glu Gly Thr Asn Lys Leu Met Pro Ala Cys
50 55 60

Val Thr Ala Val Ser Glu Glu Met Val Val His Thr Asn Thr Glu Lys
65 70 75 80

Leu Gln Asn Tyr Arg Arg Met Thr Val Glu Leu Leu Phe Ser Glu Gly
85 90 95

Asn His Val Cys Ala Ile Cys Val Ala Asn Gly Asn Cys Glu Leu Gln
100 105 110

Asp Met Ala Ile Thr Val Gly Met Asp His Ser Arg Phe Lys Tyr Gln
115 120 125

Phe Pro Lys Arg Glu Val Asp Leu Ser His Pro Met Phe Gly Ile Asp
130 135 140

His Asn Arg Cys Ile Leu Cys Thr Arg Cys Val Arg Val Cys Asp Glu
145 150 155 160

Ile Glu Gly Ala His Val Trp Asp Val Ala Tyr Arg Gly Ala Glu Cys
165 170 175

Lys Ile Val Ser Gly Leu Asn Gln Pro Trp Gly Thr Val Asp Ala Cys
180 185 190

Thr Ser Cys Gly Lys Cys Val Asp Ala Cys Pro Thr Gly Ser Ile Phe
195 200 205

His Lys Gly Glu Thr Thr Ala Glu Lys Ile Gly Asp Arg Arg Lys Val
210 215 220

Glu Phe Leu Ala Thr Ala Arg Lys Glu Lys Glu Trp Val Arg
225 230 235

<210> SEQ ID NO 22
<211> LENGTH: 534
<212> TYPE: PRT
<213> ORGANISM: Synechococcus elongatus PCC 6301

<400> SEQUENCE: 22

Met Asp Trp Glu Asp Leu Gly Arg Leu Ala Asn Glu Glu Leu Thr Cys
1 5 10 15

Gln Lys Pro Ile Arg Leu Arg Cys Cys Thr Ala Thr Gly Cys Arg Ala
20 25 30

-continued

```
Asn Gly Ala Glu Ala Val Phe Lys Ala Val Gln Gln Thr Ile Ala Asp
        35                  40                  45

Gln Asn Leu Gly Asp Arg Cys Glu Ala Val Ser Val Gly Cys Leu Gly
    50                  55                  60

Leu Cys Gly Ala Gly Pro Leu Val Gln Cys Asp Pro Ser Asp Arg Leu
65                  70                  75                  80

Tyr Ser Asp Ile Arg Pro Asp Gln Ala Ala Asp Leu Val Ala Ala Ala
                85                  90                  95

Gln Gly Ala Ala Met Asp Leu Pro Glu Val Asp Gln Ala Gln Pro Phe
            100                 105                 110

Phe Ser Gln Gln Leu Lys Ile Val Asn Arg His Ser Gly Leu Ile Asn
        115                 120                 125

Pro Asp Arg Leu Glu Ser Tyr Leu Ala Ala Gly Gly Tyr Arg Ala Leu
    130                 135                 140

Met His Thr Ile Phe Asp Leu Thr Pro Thr Glu Val Val Glu Ile Ile
145                 150                 155                 160

Arg Leu Ser Gly Leu Arg Gly Arg Gly Gly Gly Gly Tyr Pro Thr Gly
                165                 170                 175

Leu Lys Trp Ala Thr Val Ala Lys Met Pro Ser Asp Arg Lys Phe Val
            180                 185                 190

Val Cys Asn Gly Asp Glu Gly Asp Pro Gly Ala Phe Met Asp Arg Ser
        195                 200                 205

Val Leu Glu Ser Asp Pro His Gln Val Ile Glu Gly Met Ala Ile Ala
    210                 215                 220

Ala Tyr Ala Val Gly Ala Asn Phe Gly Tyr Leu Tyr Val Arg Ala Glu
225                 230                 235                 240

Tyr Pro Leu Ala Ile Ala Arg Leu Asn Gln Ala Ile Arg Gln Ala Arg
                245                 250                 255

Arg Arg Gly Leu Leu Gly Asn Ser Val Leu Asp Ser Arg Phe Ser Phe
            260                 265                 270

Asp Leu Glu Val Arg Ile Gly Ala Gly Ala Phe Val Cys Gly Glu Glu
        275                 280                 285

Thr Ala Leu Ile His Ser Ile Gln Gly Glu Arg Gly Val Pro Arg Val
    290                 295                 300

Arg Pro Pro Tyr Pro Ala Glu Ser Gly Leu Trp Gly His Pro Thr Leu
305                 310                 315                 320

Ile Asn Asn Val Glu Thr Phe Ala Asn Ile Ala Pro Ile Val Glu Gln
                325                 330                 335

Gly Ala Asp Trp Phe Ala Ala Ile Gly Thr Pro Thr Ser Lys Gly Thr
            340                 345                 350

Lys Val Phe Ala Leu Thr Gly Lys Leu Arg Asn Asn Gly Leu Ile Glu
        355                 360                 365

Val Pro Met Gly Ile Pro Leu Arg Ser Ile Val Asp Gly Met Gly Ile
    370                 375                 380

Pro Glu Ser Pro Val Lys Ala Val Gln Thr Gly Gly Pro Ser Gly Gly
385                 390                 395                 400

Cys Ile Pro Leu Ala Gln Leu Asp Thr Pro Val Asp Tyr Asp Ser Leu
                405                 410                 415

Ile Gln Leu Gly Ser Met Met Gly Ser Gly Gly Met Val Val Met Asp
            420                 425                 430

Glu Asn Thr Asp Met Val Ala Ile Ala Arg Phe Tyr Met Glu Phe Cys
        435                 440                 445
```

```
Arg Ser Glu Ser Cys Gly Lys Cys Ile Pro Cys Arg Ala Gly Thr Val
    450                 455                 460

Gln Leu His Glu Leu Leu Gly Lys Leu Ser Ser Gly Gln Gly Thr Ala
465                 470                 475                 480

Ile Asp Leu Gln Gln Leu Glu Asp Leu Cys Tyr Leu Val Lys Asp Thr
                485                 490                 495

Ser Leu Cys Gly Leu Gly Met Ser Ala Pro Asn Pro Ile Leu Ser Thr
            500                 505                 510

Leu Arg Trp Phe Arg Gln Glu Tyr Glu Ser Arg Leu Ile Pro Glu Arg
        515                 520                 525

Ala Ile Ala Leu Thr His
    530


<210> SEQ ID NO 23
<211> LENGTH: 238
<212> TYPE: PRT
<213> ORGANISM: Synechococcus elongatus PCC 6301

<400> SEQUENCE: 23

Met Ser Val Val Thr Leu Gln Ile Asp Asp Gln Glu Leu Ala Ala Asn
1               5                   10                  15

Val Gly Gln Thr Val Leu Gln Val Ala Arg Glu Ala Ser Ile Pro Ile
            20                  25                  30

Pro Thr Leu Cys His Leu Gln Gly Val Ser Asp Val Gly Ala Cys Arg
        35                  40                  45

Leu Cys Val Val Glu Val Ala Gly Ser Pro Lys Leu Gln Pro Ala Cys
    50                  55                  60

Leu Leu Thr Val Ser Glu Gly Leu Val Val Gln Thr Arg Ser Pro Arg
65                  70                  75                  80

Leu Glu Arg Tyr Arg Arg Gln Ile Val Glu Leu Phe Phe Ala Glu Gly
                85                  90                  95

Asn His Val Cys Ala Ile Cys Val Ala Asn Gly Asn Cys Glu Leu Gln
            100                 105                 110

Asp Ala Ala Ile Ala Val Gly Met Asp His Ser Arg Tyr Pro Tyr Arg
        115                 120                 125

Phe Pro Lys Arg Asp Val Asp Leu Ser His Arg Phe Phe Gly Leu Asp
    130                 135                 140

His Asn Arg Cys Ile Leu Cys Thr Arg Cys Val Arg Val Cys Asp Glu
145                 150                 155                 160

Ile Glu Gly Ala His Val Trp Asp Val Ala Met Arg Gly Glu His Cys
                165                 170                 175

Arg Ile Val Ala Gly Met Asp Gln Pro Trp Gly Ala Val Asp Ala Cys
            180                 185                 190

Thr Asn Cys Gly Lys Cys Ile Asp Ala Cys Pro Thr Gly Ala Leu Phe
        195                 200                 205

His Lys Gly Glu Thr Thr Gly Glu Ile Glu Arg Asp Arg Asp Lys Leu
    210                 215                 220

Ala Phe Leu Ala Glu Ala Arg Gly Gln Arg Arg Trp Thr Arg
225                 230                 235


<210> SEQ ID NO 24
<211> LENGTH: 488
<212> TYPE: PRT
<213> ORGANISM: Ralstonia eutropha

<400> SEQUENCE: 24
```

-continued

```
Met Ser Arg Lys Leu Val Ile Asp Pro Val Thr Arg Ile Glu Gly His
1               5                   10                  15

Gly Lys Val Val Val His Leu Asp Asp Asp Asn Lys Val Val Asp Ala
            20                  25                  30

Lys Leu His Val Val Glu Phe Arg Gly Phe Glu Lys Phe Val Gln Gly
        35                  40                  45

His Pro Phe Trp Glu Ala Pro Met Phe Leu Gln Arg Ile Cys Gly Ile
    50                  55                  60

Cys Phe Val Ser His His Leu Cys Gly Ala Lys Ala Leu Asp Asp Met
65                  70                  75                  80

Val Gly Val Gly Leu Lys Ser Gly Ile His Val Thr Pro Thr Ala Glu
                85                  90                  95

Lys Met Arg Arg Leu Gly His Tyr Ala Gln Met Leu Gln Ser His Thr
            100                 105                 110

Thr Ala Tyr Phe Tyr Leu Ile Val Pro Glu Met Leu Phe Gly Met Asp
        115                 120                 125

Ala Pro Pro Ala Gln Arg Asn Val Leu Gly Leu Ile Glu Ala Asn Pro
    130                 135                 140

Asp Leu Val Lys Arg Val Val Met Leu Arg Lys Trp Gly Gln Glu Val
145                 150                 155                 160

Ile Lys Ala Val Phe Gly Lys Lys Met His Gly Ile Asn Ser Val Pro
                165                 170                 175

Gly Gly Val Asn Asn Asn Leu Ser Ile Ala Glu Arg Asp Arg Phe Leu
            180                 185                 190

Asn Gly Glu Glu Gly Leu Leu Ser Val Asp Gln Val Ile Asp Tyr Ala
        195                 200                 205

Gln Asp Gly Leu Arg Leu Phe Tyr Asp Phe His Gln Lys His Arg Ala
    210                 215                 220

Gln Val Asp Ser Phe Ala Asp Val Pro Ala Leu Ser Met Cys Leu Val
225                 230                 235                 240

Gly Asp Asp Asp Asn Val Asp Tyr Tyr His Gly Arg Leu Arg Ile Ile
                245                 250                 255

Asp Asp Asp Lys His Ile Val Arg Glu Phe Asp Tyr His Asp Tyr Leu
            260                 265                 270

Asp His Phe Ser Glu Ala Val Glu Glu Trp Ser Tyr Met Lys Phe Pro
        275                 280                 285

Tyr Leu Lys Glu Leu Gly Arg Glu Gln Gly Ser Val Arg Val Gly Pro
    290                 295                 300

Leu Gly Arg Met Asn Val Thr Lys Ser Leu Pro Thr Pro Leu Ala Gln
305                 310                 315                 320

Glu Ala Leu Glu Arg Phe His Ala Tyr Thr Lys Gly Arg Thr Asn Asn
                325                 330                 335

Met Thr Leu His Thr Asn Trp Ala Arg Ala Ile Glu Ile Leu His Ala
            340                 345                 350

Ala Glu Val Val Lys Glu Leu Leu His Asp Pro Asp Leu Gln Lys Asp
        355                 360                 365

Gln Leu Val Leu Thr Pro Pro Pro Asn Ala Trp Thr Gly Glu Gly Val
    370                 375                 380

Gly Val Val Glu Ala Pro Arg Gly Thr Leu Leu His His Tyr Arg Ala
385                 390                 395                 400

Asp Glu Arg Gly Asn Ile Thr Phe Ala Asn Leu Val Val Ala Thr Thr
                405                 410                 415

Gln Asn Asn Gln Val Met Asn Arg Thr Val Arg Ser Val Ala Glu Asp
```

420 425 430

Tyr Leu Gly Gly His Gly Glu Ile Thr Glu Gly Met Met Asn Ala Ile
435 440 445

Glu Val Gly Ile Arg Ala Tyr Asp Pro Cys Leu Ser Cys Ala Thr His
450 455 460

Ala Leu Gly Gln Met Pro Leu Val Val Ser Val Phe Asp Ala Ala Gly
465 470 475 480

Arg Leu Ile Asp Glu Arg Ala Arg
485

<210> SEQ ID NO 25
<211> LENGTH: 209
<212> TYPE: PRT
<213> ORGANISM: Ralstonia eutropha

<400> SEQUENCE: 25

Met Arg Ala Pro His Lys Asp Glu Ile Ala Ser His Glu Leu Pro Ala
1 5 10 15

Thr Pro Met Asp Pro Ala Leu Ala Ala Asn Arg Glu Gly Lys Ile Lys
20 25 30

Val Ala Thr Ile Gly Leu Cys Gly Cys Trp Gly Cys Thr Leu Ser Phe
35 40 45

Leu Asp Met Asp Glu Arg Leu Leu Pro Leu Leu Glu Lys Val Thr Leu
50 55 60

Leu Arg Ser Ser Leu Thr Asp Ile Lys Arg Ile Pro Glu Arg Cys Ala
65 70 75 80

Ile Gly Phe Val Glu Gly Gly Val Ser Ser Glu Glu Asn Ile Glu Thr
85 90 95

Leu Glu His Phe Arg Glu Asn Cys Asp Ile Leu Ile Ser Val Gly Ala
100 105 110

Cys Ala Val Trp Gly Gly Val Pro Ala Met Arg Asn Val Phe Glu Leu
115 120 125

Lys Asp Cys Leu Ala Glu Ala Tyr Val Asn Ser Ala Thr Ala Val Pro
130 135 140

Gly Ala Lys Ala Val Val Pro Phe His Pro Asp Ile Pro Arg Ile Thr
145 150 155 160

Thr Lys Val Tyr Pro Cys His Glu Val Val Lys Met Asp Tyr Phe Ile
165 170 175

Pro Gly Cys Pro Pro Asp Gly Asp Ala Ile Phe Lys Val Leu Asp Asp
180 185 190

Leu Val Asn Gly Arg Pro Phe Asp Leu Pro Ser Ser Ile Asn Arg Tyr
195 200 205

Asp

<210> SEQ ID NO 26
<211> LENGTH: 618
<212> TYPE: PRT
<213> ORGANISM: Ralstonia eutropha

<400> SEQUENCE: 26

Met Ser Ala Tyr Ala Thr Gln Gly Phe Asn Leu Asp Asp Arg Gly Arg
1 5 10 15

Arg Ile Val Val Asp Pro Val Thr Arg Ile Glu Gly His Met Arg Cys
20 25 30

Glu Val Asn Val Asp Ala Asn Asn Val Ile Arg Asn Ala Val Ser Thr
35 40 45

-continued

```
Gly Thr Met Trp Arg Gly Leu Glu Val Ile Leu Lys Gly Arg Asp Pro
    50                  55                  60

Arg Asp Ala Trp Ala Phe Val Glu Arg Ile Cys Gly Val Cys Thr Gly
65                  70                  75                  80

Cys His Ala Leu Ala Ser Val Arg Ala Val Glu Asn Ala Leu Asp Ile
                85                  90                  95

Arg Ile Pro Lys Asn Ala His Leu Ile Arg Glu Ile Met Ala Lys Thr
            100                 105                 110

Leu Gln Val His Asp His Ala Val His Phe Tyr His Leu His Ala Leu
        115                 120                 125

Asp Trp Val Asp Val Met Ser Ala Leu Lys Ala Asp Pro Lys Arg Thr
    130                 135                 140

Ser Glu Leu Gln Gln Leu Val Ser Pro Ala His Pro Leu Ser Ser Ala
145                 150                 155                 160

Gly Tyr Phe Arg Asp Ile Gln Asn Arg Leu Lys Arg Phe Val Glu Ser
                165                 170                 175

Gly Gln Leu Gly Pro Phe Met Asn Gly Tyr Trp Gly Ser Lys Ala Tyr
            180                 185                 190

Val Leu Pro Pro Glu Ala Asn Leu Met Ala Val Thr His Tyr Leu Glu
        195                 200                 205

Ala Leu Asp Leu Gln Lys Glu Trp Val Lys Ile His Thr Ile Phe Gly
    210                 215                 220

Gly Lys Asn Pro His Pro Asn Tyr Leu Val Gly Gly Val Pro Cys Ala
225                 230                 235                 240

Ile Asn Leu Asp Gly Ile Gly Ala Ala Ser Ala Pro Val Asn Met Glu
                245                 250                 255

Arg Leu Ser Phe Val Lys Ala Arg Ile Asp Glu Ile Ile Glu Phe Asn
            260                 265                 270

Lys Asn Val Tyr Val Pro Asp Val Leu Ala Ile Gly Thr Leu Tyr Lys
        275                 280                 285

Gln Ala Gly Trp Leu Tyr Gly Gly Gly Leu Ala Ala Thr Asn Val Leu
    290                 295                 300

Asp Tyr Gly Glu Tyr Pro Asn Val Ala Tyr Asn Lys Ser Thr Asp Gln
305                 310                 315                 320

Leu Pro Gly Gly Ala Ile Leu Asn Gly Asn Trp Asp Glu Val Phe Pro
                325                 330                 335

Val Asp Pro Arg Asp Ser Gln Gln Val Gln Glu Phe Val Ser His Ser
            340                 345                 350

Trp Tyr Lys Tyr Ala Asp Glu Ser Val Gly Leu His Pro Trp Asp Gly
        355                 360                 365

Val Thr Glu Pro Asn Tyr Val Leu Gly Ala Asn Thr Lys Gly Thr Arg
    370                 375                 380

Thr Arg Ile Glu Gln Ile Asp Glu Ser Ala Lys Tyr Ser Trp Ile Lys
385                 390                 395                 400

Ser Pro Arg Trp Arg Gly His Ala Met Glu Val Gly Pro Leu Ser Arg
                405                 410                 415

Tyr Ile Leu Ala Tyr Ala His Ala Arg Ser Gly Asn Lys Tyr Ala Glu
            420                 425                 430

Arg Pro Lys Glu Gln Leu Glu Tyr Ser Ala Gln Met Ile Asn Ser Ala
        435                 440                 445

Ile Pro Lys Ala Leu Gly Leu Pro Glu Thr Gln Tyr Thr Leu Lys Gln
    450                 455                 460
```

```
Leu Leu Pro Ser Thr Ile Gly Arg Thr Leu Ala Arg Ala Leu Glu Ser
465                 470                 475                 480

Gln Tyr Cys Gly Glu Met Met His Ser Asp Trp His Asp Leu Val Ala
                485                 490                 495

Asn Ile Arg Ala Gly Asp Thr Ala Thr Ala Asn Val Asp Lys Trp Asp
            500                 505                 510

Pro Ala Thr Trp Pro Leu Gln Ala Lys Gly Val Gly Thr Val Ala Ala
        515                 520                 525

Pro Arg Gly Ala Leu Gly His Trp Ile Arg Ile Lys Asp Gly Arg Ile
    530                 535                 540

Glu Asn Tyr Gln Cys Val Val Pro Thr Thr Trp Asn Gly Ser Pro Arg
545                 550                 555                 560

Asp Tyr Lys Gly Gln Ile Gly Ala Phe Glu Ala Ser Leu Met Asn Thr
                565                 570                 575

Pro Met Val Asn Pro Glu Gln Pro Val Glu Ile Leu Arg Thr Leu His
            580                 585                 590

Ser Phe Asp Pro Cys Leu Ala Cys Ser Thr His Val Met Ser Ala Glu
        595                 600                 605

Gly Gln Glu Leu Thr Thr Val Lys Val Arg
    610                 615


<210> SEQ ID NO 27
<211> LENGTH: 360
<212> TYPE: PRT
<213> ORGANISM: Ralstonia eutropha

<400> SEQUENCE: 27

Met Val Glu Thr Phe Tyr Glu Val Met Arg Arg Gln Gly Ile Ser Arg
1               5                   10                  15

Arg Ser Phe Leu Lys Tyr Cys Ser Leu Thr Ala Thr Ser Leu Gly Leu
            20                  25                  30

Gly Pro Ser Phe Leu Pro Gln Ile Ala His Ala Met Glu Thr Lys Pro
        35                  40                  45

Arg Thr Pro Val Leu Trp Leu His Gly Leu Glu Cys Thr Cys Cys Ser
    50                  55                  60

Glu Ser Phe Ile Arg Ser Ala His Pro Leu Ala Lys Asp Val Val Leu
65                  70                  75                  80

Ser Met Ile Ser Leu Asp Tyr Asp Asp Thr Leu Met Ala Ala Ala Gly
                85                  90                  95

His Gln Ala Glu Ala Ile Leu Glu Glu Ile Met Thr Lys Tyr Lys Gly
            100                 105                 110

Asn Tyr Ile Leu Ala Val Glu Gly Asn Pro Pro Leu Asn Gln Asp Gly
        115                 120                 125

Met Ser Cys Ile Ile Gly Gly Arg Pro Phe Ile Glu Gln Leu Lys Tyr
    130                 135                 140

Val Ala Lys Asp Ala Lys Ala Ile Ile Ser Trp Gly Ser Cys Ala Ser
145                 150                 155                 160

Trp Gly Cys Val Gln Ala Ala Lys Pro Asn Pro Thr Gln Ala Thr Pro
                165                 170                 175

Val His Lys Val Ile Thr Asp Lys Pro Ile Ile Lys Val Pro Gly Cys
            180                 185                 190

Pro Pro Ile Ala Glu Val Met Thr Gly Val Ile Thr Tyr Met Leu Thr
        195                 200                 205

Phe Asp Arg Ile Pro Glu Leu Asp Arg Gln Gly Arg Pro Lys Met Phe
    210                 215                 220
```

```
Tyr Ser Gln Arg Ile His Asp Lys Cys Tyr Arg Arg Pro His Phe Asp
225                 230                 235                 240

Ala Gly Gln Phe Val Glu Glu Trp Asp Asp Glu Ser Ala Arg Lys Gly
                245                 250                 255

Phe Cys Leu Tyr Lys Met Gly Cys Lys Gly Pro Thr Thr Tyr Asn Ala
            260                 265                 270

Cys Ser Thr Thr Arg Trp Asn Glu Gly Thr Ser Phe Pro Ile Gln Ser
        275                 280                 285

Gly His Gly Cys Ile Gly Cys Ser Glu Asp Gly Phe Trp Asp Lys Gly
    290                 295                 300

Ser Phe Tyr Asp Arg Leu Thr Gly Ile Ser Gln Phe Gly Val Glu Ala
305                 310                 315                 320

Asn Ala Asp Lys Ile Gly Gly Thr Ala Ser Val Val Val Gly Ala Ala
                325                 330                 335

Val Thr Ala His Ala Ala Ala Ser Ala Ile Lys Arg Ala Ser Lys Lys
            340                 345                 350

Asn Glu Thr Ser Gly Ser Glu His
        355                 360


<210> SEQ ID NO 28
<211> LENGTH: 244
<212> TYPE: PRT
<213> ORGANISM: Ralstonia eutropha

<400> SEQUENCE: 28

Met Ser Thr Lys Met Gln Ala Asp Arg Ile Ala Asp Ala Thr Gly Thr
1               5                   10                  15

Asp Glu Gly Ala Val Ala Ser Gly Lys Ser Ile Lys Ala Thr Tyr Val
            20                  25                  30

Tyr Glu Ala Pro Val Arg Leu Trp His Trp Val Asn Ala Leu Ala Ile
        35                  40                  45

Val Val Leu Ala Val Thr Gly Phe Phe Ile Gly Ser Pro Pro Ala Thr
    50                  55                  60

Arg Pro Gly Glu Ala Ser Ala Asn Phe Leu Met Gly Tyr Ile Arg Phe
65                  70                  75                  80

Ala His Phe Val Ala Ala Tyr Ile Phe Ala Ile Gly Met Leu Gly Arg
                85                  90                  95

Ile Tyr Trp Ala Thr Ala Gly Asn His His Ser Arg Glu Leu Phe Ser
            100                 105                 110

Val Pro Val Phe Thr Arg Ala Tyr Trp Gln Glu Val Ile Ser Met Leu
        115                 120                 125

Arg Trp Tyr Ala Phe Leu Ser Ala Arg Pro Ser Arg Tyr Val Gly His
    130                 135                 140

Asn Pro Leu Ala Arg Phe Ala Met Phe Phe Ile Phe Phe Leu Ser Ser
145                 150                 155                 160

Val Phe Met Ile Leu Thr Gly Phe Ala Met Tyr Gly Glu Gly Ala Gln
                165                 170                 175

Met Gly Ser Trp Gln Glu Arg Met Phe Gly Trp Val Ile Pro Leu Leu
            180                 185                 190

Gly Gln Ser Gln Asp Val His Thr Trp His His Leu Gly Met Trp Phe
        195                 200                 205

Ile Val Val Phe Val Ile Val His Val Tyr Ala Ala Ile Arg Glu Asp
    210                 215                 220

Ile Met Gly Arg Gln Ser Val Val Ser Thr Met Val Ser Gly Tyr Arg
```

225 230 235 240

Thr Phe Lys Asp

<210> SEQ ID NO 29
<211> LENGTH: 347
<212> TYPE: PRT
<213> ORGANISM: Ralstonia eutropha

<400> SEQUENCE: 29

Met Asn Ala Pro Val Cys Thr Gly Leu Ala Ser Ala Lys Pro Gly Val
1 5 10 15

Leu Asn Val Leu Trp Ile Gln Ser Gly Gly Cys Gly Gly Cys Ser Met
20 25 30

Ser Leu Leu Cys Ala Asp Thr Thr Asp Phe Thr Gly Met Leu Lys Ser
35 40 45

Ala Gly Ile His Met Leu Trp His Pro Ser Leu Ser Leu Glu Ser Gly
50 55 60

Val Glu Gln Leu Gln Ile Leu Glu Asp Cys Leu Gln Gly Arg Val Ala
65 70 75 80

Leu His Ala Leu Cys Val Glu Gly Ala Met Leu Arg Gly Pro His Gly
85 90 95

Thr Gly Arg Phe His Leu Leu Ala Gly Thr Gly Val Pro Met Ile Glu
100 105 110

Trp Val Ser Arg Leu Ala Ala Val Ala Asp Tyr Thr Leu Ala Val Gly
115 120 125

Thr Cys Ala Ala Tyr Gly Gly Ile Thr Ala Gly Gly Gly Asn Pro Thr
130 135 140

Asp Ala Cys Gly Leu Gln Tyr Glu Gly Asp Gln Pro Gly Gly Leu Leu
145 150 155 160

Gly Leu Asn Tyr Arg Ser Arg Ala Gly Leu Pro Val Ile Asn Val Ala
165 170 175

Gly Cys Pro Thr His Pro Gly Trp Val Thr Asp Ala Leu Ala Leu Leu
180 185 190

Ser Ala Arg Leu Leu Thr Ala Ser Asp Leu Asp Thr Leu Gly Arg Pro
195 200 205

Arg Phe Tyr Ala Asp Gln Leu Val His His Gly Cys Thr Arg Asn Glu
210 215 220

Tyr Tyr Glu Phe Lys Ala Ser Ala Glu Lys Pro Ser Asp Leu Gly Cys
225 230 235 240

Met Met Glu Asn Met Gly Cys Lys Gly Thr Gln Ala His Ala Asp Cys
245 250 255

Asn Thr Arg Leu Trp Asn Gly Glu Gly Ser Cys Thr Arg Gly Gly Tyr
260 265 270

Ala Cys Ile Ser Cys Thr Glu Pro Gly Phe Glu Glu Pro Gly His Pro
275 280 285

Phe His Gln Thr Pro Lys Val Ala Gly Ile Pro Ile Gly Leu Pro Thr
290 295 300

Asp Met Pro Lys Ala Trp Phe Val Ala Leu Ala Ser Leu Ser Lys Ser
305 310 315 320

Ala Thr Pro Lys Arg Val Lys Leu Asn Ala Thr Ala Asp His Pro Leu
325 330 335

Ile Ala Pro Ala Ile Arg Lys Thr Arg Leu Lys
340 345

<210> SEQ ID NO 30
<211> LENGTH: 485
<212> TYPE: PRT
<213> ORGANISM: Ralstonia eutropha

<400> SEQUENCE: 30

```
Met Glu Arg Leu Val Val Gly Pro Phe Asn Arg Val Glu Gly Asp Leu
1               5                   10                  15

Glu Val Asn Leu Glu Val Ala Ser Gly Arg Val Cys Ser Ala Arg Val
            20                  25                  30

Asn Ala Thr Met Tyr Arg Gly Leu Glu Gln Ile Leu Leu His Arg His
        35                  40                  45

Pro Leu Asp Ala Leu Val Tyr Ala Pro Arg Val Cys Gly Ile Cys Ser
    50                  55                  60

Val Ser Gln Ser Val Ala Ala Ser Arg Ala Leu Ala Asp Leu Ala Gly
65                  70                  75                  80

Val Thr Val Pro Ala Asn Gly Met Leu Ala Met Asn Leu Met Leu Ala
                85                  90                  95

Thr Glu Asn Leu Ala Asp His Leu Thr His Phe Tyr Leu Phe Phe Met
            100                 105                 110

Pro Asp Phe Thr Arg Glu Ile Tyr Ala Gly Arg Pro Trp His Thr Asp
        115                 120                 125

Ala Thr Ala Arg Phe Ser Pro Thr His Gly Lys His His Arg Leu Ala
    130                 135                 140

Ile Ala Ala Arg Gln Arg Trp Phe Thr Leu Met Gly Thr Leu Gly Gly
145                 150                 155                 160

Lys Trp Pro His Thr Glu Ser Val Gln Pro Gly Gly Ser Ser Arg Ala
                165                 170                 175

Ile Asp Ala Ala Glu Arg Val Arg Leu Leu Gly Arg Val Arg Glu Phe
            180                 185                 190

Arg Cys Phe Leu Glu Gln Thr Leu Tyr Ala Ala Pro Leu Glu Asp Val
        195                 200                 205

Val Ala Leu Asp Ser Glu Val Ala Leu Trp Arg Trp His Ala Gln Ala
    210                 215                 220

Pro Gln Ala Gly Asp Leu Arg Cys Phe Leu Thr Ile Ala Gln Asp Ala
225                 230                 235                 240

Ala Leu Asp Gln Met Gly Pro Gly Pro Gly Thr Tyr Leu Ser Tyr Gly
                245                 250                 255

Ala Tyr Pro Gln Pro Glu Gly Gly Phe Cys Phe Ala Gln Gly Val Trp
            260                 265                 270

Arg Ser Ala Gln Gly Arg Leu Asp Ala Leu Asp Leu Ala Ala Ile Ser
        275                 280                 285

Glu Asp Ala Thr Ser Ala Trp Leu Val Asp Gln Gly Gly Ala Arg His
    290                 295                 300

Pro Ala Asn Gly Leu Thr Ala Pro Ala Pro Asp Lys Val Gly Ala Tyr
305                 310                 315                 320

Thr Trp Asn Lys Ala Pro Arg Leu Ala Gly Ala Val Leu Glu Thr Gly
                325                 330                 335

Ala Ile Ala Arg Gln Leu Ala Gly Ala Gln Pro Leu Val Arg Asp Ala
            340                 345                 350

Val Ala Arg Cys Gly Ala Thr Val Tyr Thr Arg Val Leu Ala Arg Leu
        355                 360                 365

Val Glu Leu Ala Arg Val Val Pro Leu Met Glu Asp Trp Leu Gln Ser
    370                 375                 380
```

```
Leu Glu Ile Gly Ala Pro Tyr Trp Ala Ser Ala His Leu Pro Asp Gln
385                 390                 395                 400

Gly Ala Gly Val Gly Leu Thr Glu Ala Ala Arg Gly Ser Leu Gly His
                405                 410                 415

Trp Val Ser Val Arg Asp Gly Arg Ile Asp Asn Tyr Gln Ile Val Ala
            420                 425                 430

Pro Thr Ser Trp Asn Phe Ser Pro Arg Asp Ile Ala Gly Gln Pro Gly
        435                 440                 445

Ala Val Glu Lys Ala Leu Glu Gly Ala Pro Val Leu Gln Gly Glu Thr
    450                 455                 460

Thr Pro Val Ala Val Gln His Ile Val Arg Ser Phe Asp Pro Cys Met
465                 470                 475                 480

Val Cys Thr Val His
                485


<210> SEQ ID NO 31
<211> LENGTH: 597
<212> TYPE: PRT
<213> ORGANISM: Escherichia coli

<400> SEQUENCE: 31

Met Ser Thr Gln Tyr Glu Thr Gln Gly Tyr Thr Ile Asn Asn Ala Gly
1               5                   10                  15

Arg Arg Leu Val Val Asp Pro Ile Thr Arg Ile Glu Gly His Met Arg
            20                  25                  30

Cys Glu Val Asn Ile Asn Asp Gln Asn Val Ile Thr Asn Ala Val Ser
        35                  40                  45

Cys Gly Thr Met Phe Arg Gly Leu Glu Ile Ile Leu Gln Gly Arg Asp
    50                  55                  60

Pro Arg Asp Ala Trp Ala Phe Val Glu Arg Ile Cys Gly Val Cys Thr
65                  70                  75                  80

Gly Val His Ala Leu Ala Ser Val Tyr Ala Ile Glu Asp Ala Ile Gly
                85                  90                  95

Ile Lys Val Pro Asp Asn Ala Asn Ile Ile Arg Asn Ile Met Leu Ala
            100                 105                 110

Thr Leu Trp Cys His Asp His Leu Val His Phe Tyr Gln Leu Ala Gly
        115                 120                 125

Met Asp Trp Ile Asp Val Leu Asp Ala Leu Lys Ala Asp Pro Arg Lys
    130                 135                 140

Thr Ser Glu Leu Ala Gln Ser Leu Ser Ser Trp Pro Lys Ser Ser Pro
145                 150                 155                 160

Gly Tyr Phe Phe Asp Val Gln Asn Arg Leu Lys Lys Phe Val Glu Gly
                165                 170                 175

Gly Gln Leu Gly Ile Phe Arg Asn Gly Tyr Trp Gly His Pro Gln Tyr
            180                 185                 190

Lys Leu Pro Pro Glu Ala Asn Leu Met Gly Phe Ala His Tyr Leu Glu
        195                 200                 205

Ala Leu Asp Phe Gln Arg Glu Ile Val Lys Ile His Ala Val Phe Gly
    210                 215                 220

Gly Lys Asn Pro His Pro Asn Trp Ile Val Gly Gly Met Pro Cys Ala
225                 230                 235                 240

Ile Asn Ile Asp Glu Ser Gly Ala Val Gly Ala Val Asn Met Glu Arg
                245                 250                 255

Leu Asn Leu Val Gln Ser Ile Ile Thr Arg Thr Ala Asp Phe Ile Asn
            260                 265                 270
```

Asn Val Met Ile Pro Asp Ala Leu Ala Ile Gly Gln Phe Asn Lys Pro
275 280 285

Trp Ser Glu Ile Gly Thr Gly Leu Ser Asp Lys Cys Val Leu Ser Tyr
290 295 300

Gly Ala Phe Pro Asp Ile Ala Asn Asp Phe Gly Glu Lys Ser Leu Leu
305 310 315 320

Met Pro Gly Gly Ala Val Ile Asn Gly Asp Phe Asn Asn Val Leu Pro
325 330 335

Val Asp Leu Val Asp Pro Gln Gln Val Gln Glu Phe Val Asp His Ala
340 345 350

Trp Tyr Arg Tyr Pro Asn Asp Gln Val Gly Arg His Pro Phe Asp Gly
355 360 365

Ile Thr Asp Pro Trp Tyr Asn Pro Gly Asp Val Lys Gly Ser Asp Thr
370 375 380

Asn Ile Gln Gln Leu Asn Glu Gln Glu Arg Tyr Ser Trp Ile Lys Ala
385 390 395 400

Pro Arg Trp Arg Gly Asn Ala Met Glu Val Gly Pro Leu Ala Arg Thr
405 410 415

Leu Ile Ala Tyr His Lys Gly Asp Ala Ala Thr Val Glu Ser Val Asp
420 425 430

Arg Met Met Ser Ala Leu Asn Leu Pro Leu Ser Gly Ile Gln Ser Thr
435 440 445

Leu Gly Arg Ile Leu Cys Arg Ala His Glu Ala Gln Trp Ala Ala Gly
450 455 460

Lys Leu Gln Tyr Phe Phe Asn Lys Leu Met Thr Asn Leu Lys Asn Gly
465 470 475 480

Asn Leu Ala Thr Ala Ser Thr Glu Lys Trp Glu Pro Thr Thr Trp Pro
485 490 495

Thr Glu Cys Arg Gly Val Gly Phe Thr Glu Ala Pro Arg Gly Ala Leu
500 505 510

Gly His Trp Ala Ala Ile Arg Asp Gly Lys Ile Asp Leu Tyr Gln Cys
515 520 525

Val Val Pro Thr Thr Trp Asn Ala Ser Pro Arg Asp Pro Lys Gly Gln
530 535 540

Ile Gly Ala Tyr Glu Ala Ala Leu Met Asn Thr Lys Met Ala Ile Pro
545 550 555 560

Glu Gln Pro Leu Glu Ile Leu Arg Thr Leu His Ser Phe Asp Pro Cys
565 570 575

Leu Ala Cys Ser Thr His Val Leu Gly Asp Asp Gly Ser Glu Leu Ile
580 585 590

Ser Val Gln Val Arg
595

<210> SEQ ID NO 32
<211> LENGTH: 372
<212> TYPE: PRT
<213> ORGANISM: Escherichia coli

<400> SEQUENCE: 32

Met Asn Asn Glu Glu Thr Phe Tyr Gln Ala Met Arg Arg Gln Gly Val
1 5 10 15

Thr Arg Arg Ser Phe Leu Lys Tyr Cys Ser Leu Ala Ala Thr Ser Leu
20 25 30

Gly Leu Gly Ala Gly Met Ala Pro Lys Ile Ala Trp Ala Leu Glu Asn

```
        35                  40                  45

Lys Pro Arg Ile Pro Val Val Trp Ile His Gly Leu Glu Cys Thr Cys
    50                  55                  60

Cys Thr Glu Ser Phe Ile Arg Ser Ala His Pro Leu Ala Lys Asp Val
65                  70                  75                  80

Ile Leu Ser Leu Ile Ser Leu Asp Tyr Asp Asp Thr Leu Met Ala Ala
                85                  90                  95

Ala Gly Thr Gln Ala Glu Glu Val Phe Glu Asp Ile Ile Thr Gln Tyr
            100                 105                 110

Asn Gly Lys Tyr Ile Leu Ala Val Glu Gly Asn Pro Pro Leu Gly Glu
        115                 120                 125

Gln Gly Met Phe Cys Ile Ser Ser Gly Arg Pro Phe Ile Glu Lys Leu
    130                 135                 140

Lys Arg Ala Ala Ala Gly Ala Ser Ala Ile Ile Ala Trp Gly Thr Cys
145                 150                 155                 160

Ala Ser Trp Gly Cys Val Gln Ala Ala Arg Pro Asn Pro Thr Gln Ala
                165                 170                 175

Thr Ser Ile Asp Lys Val Ile Thr Asp Lys Pro Ile Ile Lys Val Pro
            180                 185                 190

Gly Cys Pro Pro Ile Pro Asp Val Met Ser Ala Ile Ile Thr Tyr Met
        195                 200                 205

Val Thr Phe Asp Arg Leu Pro Asp Val Asp Arg Met Gly Arg Pro Leu
    210                 215                 220

Met Phe Tyr Gly Gln Arg Ile His Asp Lys Cys Tyr Arg Arg Ala His
225                 230                 235                 240

Phe Asp Ala Gly Glu Phe Val Gln Ser Trp Asp Asp Asp Ala Ala Arg
                245                 250                 255

Lys Gly Tyr Cys Leu Tyr Lys Met Gly Cys Lys Gly Pro Thr Thr Tyr
            260                 265                 270

Asn Ala Cys Ser Ser Thr Arg Trp Asn Asp Gly Val Ser Phe Pro Ile
        275                 280                 285

Gln Ser Gly His Gly Cys Leu Gly Cys Ala Glu Asn Gly Phe Trp Asp
    290                 295                 300

Arg Gly Ser Phe Tyr Ser Arg Val Val Asp Ile Pro Gln Met Gly Thr
305                 310                 315                 320

His Ser Thr Ala Asp Thr Val Gly Leu Thr Ala Leu Gly Val Val Ala
                325                 330                 335

Ala Ala Val Gly Val His Ala Val Ala Ser Ala Val Asp Gln Arg Arg
            340                 345                 350

Arg His Asn Gln Gln Pro Thr Glu Thr Glu His Gln Pro Gly Asn Glu
        355                 360                 365

Asp Lys Gln Ala
    370


<210> SEQ ID NO 33
<211> LENGTH: 567
<212> TYPE: PRT
<213> ORGANISM: Escherichia coli

<400> SEQUENCE: 33

Met Ser Gln Arg Ile Thr Ile Asp Pro Val Thr Arg Ile Glu Gly His
1               5                   10                  15

Leu Arg Ile Asp Cys Glu Ile Glu Asn Gly Val Val Ser Lys Ala Trp
            20                  25                  30
```

-continued

```
Ala Ser Gly Thr Met Trp Arg Gly Met Glu Glu Ile Val Lys Asn Arg
        35                  40                  45

Asp Pro Arg Asp Ala Trp Met Ile Val Gln Arg Ile Cys Gly Val Cys
    50                  55                  60

Thr Thr Thr His Ala Leu Ser Ser Val Arg Ala Ala Glu Ser Ala Leu
65                  70                  75                  80

Asn Ile Asp Val Pro Val Asn Ala Gln Tyr Ile Arg Asn Ile Ile Leu
                85                  90                  95

Ala Ala His Thr Thr His Asp His Ile Val His Phe Tyr Gln Leu Ser
            100                 105                 110

Ala Leu Asp Trp Val Asp Ile Thr Ser Ala Leu Gln Ala Asp Pro Thr
        115                 120                 125

Lys Ala Ser Glu Met Leu Lys Gly Val Ser Thr Trp His Leu Asn Ser
    130                 135                 140

Pro Glu Glu Phe Thr Lys Val Gln Asn Lys Ile Lys Asp Leu Val Ala
145                 150                 155                 160

Ser Gly Gln Leu Gly Ile Phe Ala Asn Gly Tyr Trp Gly His Pro Ala
                165                 170                 175

Met Lys Leu Pro Pro Glu Val Asn Leu Ile Ala Val Ala His Tyr Leu
            180                 185                 190

Gln Ala Leu Glu Cys Gln Arg Asp Ala Asn Arg Val Val Ala Leu Leu
        195                 200                 205

Gly Gly Lys Thr Pro His Ile Gln Asn Leu Ala Val Gly Gly Val Ala
    210                 215                 220

Asn Pro Ile Asn Leu Asp Gly Leu Gly Val Leu Asn Leu Glu Arg Leu
225                 230                 235                 240

Met Tyr Ile Lys Ser Phe Ile Asp Lys Leu Ser Asp Phe Val Glu Gln
                245                 250                 255

Val Tyr Lys Val Asp Thr Ala Val Ile Ala Ala Phe Tyr Pro Glu Trp
            260                 265                 270

Leu Thr Arg Gly Lys Gly Ala Val Asn Tyr Leu Ser Val Pro Glu Phe
        275                 280                 285

Pro Thr Asp Ser Lys Asn Gly Ser Phe Leu Phe Pro Gly Gly Tyr Ile
    290                 295                 300

Glu Asn Ala Asp Leu Ser Ser Tyr Arg Pro Ile Thr Ser His Ser Asp
305                 310                 315                 320

Glu Tyr Leu Ile Lys Gly Ile Gln Glu Ser Ala Lys His Ser Trp Tyr
                325                 330                 335

Lys Asp Glu Ala Pro Gln Ala Pro Trp Glu Gly Thr Thr Ile Pro Ala
            340                 345                 350

Tyr Asp Gly Trp Ser Asp Asp Gly Lys Tyr Ser Trp Val Lys Ser Pro
        355                 360                 365

Thr Phe Tyr Gly Lys Thr Val Glu Val Gly Pro Leu Ala Asn Met Leu
    370                 375                 380

Val Lys Leu Ala Ala Gly Arg Glu Ser Thr Gln Asn Lys Leu Asn Glu
385                 390                 395                 400

Ile Val Ala Ile Tyr Gln Lys Leu Thr Gly Asn Thr Leu Glu Val Ala
                405                 410                 415

Gln Leu His Ser Thr Leu Gly Arg Ile Ile Gly Arg Thr Val His Cys
            420                 425                 430

Cys Glu Leu Gln Asp Ile Leu Gln Asn Gln Tyr Ser Ala Leu Ile Thr
        435                 440                 445

Asn Ile Gly Lys Gly Asp His Thr Thr Phe Val Lys Pro Asn Ile Pro
```

```
    450                 455                 460

Ala Thr Gly Glu Phe Lys Gly Val Gly Phe Leu Glu Ala Pro Arg Gly
465                 470                 475                 480

Met Leu Ser His Trp Met Val Ile Lys Asp Gly Ile Ile Ser Asn Tyr
                485                 490                 495

Gln Ala Val Val Pro Ser Thr Trp Asn Ser Gly Pro Arg Asn Phe Asn
            500                 505                 510

Asp Asp Val Gly Pro Tyr Glu Gln Ser Leu Val Gly Thr Pro Val Ala
        515                 520                 525

Asp Pro Asn Lys Pro Leu Glu Val Val Arg Thr Ile His Ser Phe Asp
    530                 535                 540

Pro Cys Met Ala Cys Ala Val His Val Val Asp Ala Asp Gly Asn Glu
545                 550                 555                 560

Val Val Ser Val Lys Val Leu
                565


<210> SEQ ID NO 34
<211> LENGTH: 328
<212> TYPE: PRT
<213> ORGANISM: Escherichia coli

<400> SEQUENCE: 34

Met Asn Arg Arg Asn Phe Ile Lys Ala Ala Ser Cys Gly Ala Leu Leu
1               5                   10                  15

Thr Gly Ala Leu Pro Ser Val Ser His Ala Ala Ala Glu Asn Arg Pro
            20                  25                  30

Pro Ile Pro Gly Ser Leu Gly Met Leu Tyr Asp Ser Thr Leu Cys Val
        35                  40                  45

Gly Cys Gln Ala Cys Val Thr Lys Cys Gln Asp Ile Asn Phe Pro Glu
    50                  55                  60

Arg Asn Pro Gln Gly Glu Gln Thr Trp Ser Asn Asn Asp Lys Leu Ser
65                  70                  75                  80

Pro Tyr Thr Asn Asn Ile Ile Gln Val Trp Thr Ser Gly Thr Gly Val
                85                  90                  95

Asn Lys Asp Gln Glu Glu Asn Gly Tyr Ala Tyr Ile Lys Lys Gln Cys
            100                 105                 110

Met His Cys Val Asp Pro Asn Cys Val Ser Val Cys Pro Val Ser Ala
        115                 120                 125

Leu Lys Lys Asp Pro Lys Thr Gly Ile Val His Tyr Asp Lys Asp Val
    130                 135                 140

Cys Thr Gly Cys Arg Tyr Cys Met Val Ala Cys Pro Tyr Asn Val Pro
145                 150                 155                 160

Lys Tyr Asp Tyr Asn Asn Pro Phe Gly Ala Leu His Lys Cys Glu Leu
                165                 170                 175

Cys Asn Gln Lys Gly Val Glu Arg Leu Asp Lys Gly Gly Leu Pro Gly
            180                 185                 190

Cys Val Glu Val Cys Pro Ala Gly Ala Val Ile Phe Gly Thr Arg Glu
        195                 200                 205

Glu Leu Met Ala Glu Ala Lys Lys Arg Leu Ala Leu Lys Pro Gly Ser
    210                 215                 220

Glu Tyr His Tyr Pro Arg Gln Thr Leu Lys Ser Gly Asp Thr Tyr Leu
225                 230                 235                 240

His Thr Val Pro Lys Tyr Tyr Pro His Leu Tyr Gly Glu Lys Glu Gly
                245                 250                 255
```

Gly Gly Thr Gln Val Leu Val Leu Thr Gly Val Pro Tyr Glu Asn Leu
260 265 270

Asp Leu Pro Lys Leu Asp Asp Leu Ser Thr Gly Ala Arg Ser Glu Asn
275 280 285

Ile Gln His Thr Leu Tyr Lys Gly Met Met Leu Pro Leu Ala Val Leu
290 295 300

Ala Gly Leu Thr Val Leu Val Arg Arg Asn Thr Lys Asn Asp His His
305 310 315 320

Asp Gly Gly Asp Asp His Glu Ser
325

<210> SEQ ID NO 35
<211> LENGTH: 633
<212> TYPE: PRT
<213> ORGANISM: Aquifex aeolicus

<400> SEQUENCE: 35

Met Lys Arg Val Val Val Asp Pro Val Thr Arg Ile Glu Gly His Leu
1 5 10 15

Arg Ile Glu Ile Met Val Asp Glu Glu Thr Gly Gln Val Lys Asp Ala
20 25 30

Leu Ser Ala Gly Thr Met Trp Arg Gly Ile Glu Leu Ile Val Arg Asn
35 40 45

Arg Asp Pro Arg Asp Val Trp Ala Phe Thr Gln Arg Ile Cys Gly Val
50 55 60

Cys Thr Ser Ile His Ala Leu Ala Ser Leu Arg Ala Val Glu Asp Ala
65 70 75 80

Leu Glu Ile Thr Ile Pro Lys Asn Ala Asn Tyr Ile Arg Asn Ile Met
85 90 95

Tyr Gly Ser Leu Gln Val His Asp His Val Val His Phe Tyr His Leu
100 105 110

His Ala Leu Asp Trp Val Ser Pro Val Glu Ala Leu Lys Ala Asp Pro
115 120 125

Val Ala Thr Ala Ala Leu Ala Asn Lys Ile Leu Glu Lys Tyr Gly Val
130 135 140

Leu Asn Glu Phe Met Pro Asp Phe Leu Gly His Arg Ala Tyr Pro Lys
145 150 155 160

Lys Phe Pro Lys Ala Thr Pro Gly Tyr Phe Arg Glu Phe Gln Lys Lys
165 170 175

Ile Lys Lys Leu Val Glu Ser Gly Gln Leu Gly Ile Phe Ala Ala His
180 185 190

Trp Trp Asp His Pro Asp Tyr Gln Met Leu Pro Pro Glu Val His Leu
195 200 205

Ile Gly Ile Ala His Tyr Leu Asn Met Leu Asp Val Gln Arg Glu Leu
210 215 220

Phe Ile Pro Gln Val Val Phe Gly Gly Lys Asn Pro His Pro His Tyr
225 230 235 240

Ile Val Gly Gly Val Asn Cys Ser Ile Ser Met Asp Asp Met Asn Ala
245 250 255

Pro Val Asn Ala Glu Arg Leu Ala Val Val Glu Asp Ala Ile Tyr Thr
260 265 270

Gln Val Glu Ser Thr Asp Phe Phe Tyr Ile Pro Asp Ile Leu Ala Ile
275 280 285

Ala Asp Ile Tyr Leu Asn Gln His Asn Trp Phe Tyr Gly Gly Gly Leu
290 295 300

Ser Lys Lys Arg Val Ile Gly Tyr Gly Asp Tyr Pro Asp Glu Pro Tyr
305 310 315 320

Thr Gly Ile Lys Asn Gly Asp Tyr His Lys Lys Ile Leu Trp His Ser
325 330 335

Asn Gly Val Val Glu Asp Phe Tyr Lys Gly Val Glu Lys Ala Lys Phe
340 345 350

Tyr Asn Leu Glu Gly Lys Asp Phe Thr Asp Pro Glu Gln Ile Gln Glu
355 360 365

Phe Val Thr His Ser Trp Tyr Lys Tyr Pro Asp Glu Thr Lys Gly Leu
370 375 380

His Pro Trp Asp Gly Ile Thr Glu Pro Asn Tyr Thr Gly Pro Lys Glu
385 390 395 400

Gly Thr Lys Thr His Trp Lys Tyr Leu Asp Glu Asn Gly Lys Tyr Ser
405 410 415

Trp Ile Lys Ala Pro Arg Trp Arg Gly Lys Ala Cys Glu Val Gly Pro
420 425 430

Leu Ala Arg Tyr Ile Ile Val Tyr Thr Lys Val Lys Gln Gly His Ile
435 440 445

Lys Pro Thr Trp Val Asp Glu Leu Ile Val Asn Gln Ile Asp Thr Val
450 455 460

Ser Lys Ile Leu Asn Leu Pro Pro Glu Lys Trp Leu Pro Thr Thr Val
465 470 475 480

Gly Arg Thr Ile Ala Arg Ala Leu Glu Ala Gln Met Ser Ala His Thr
485 490 495

Asn Leu Tyr Trp Met Lys Lys Leu Tyr Asp Asn Ile Lys Ala Gly Asp
500 505 510

Thr Ser Val Ala Asn Met Glu Lys Trp Asp Pro Ser Thr Trp Pro Lys
515 520 525

Glu Ala Lys Gly Val Gly Leu Thr Glu Ala Pro Arg Gly Ala Leu Gly
530 535 540

His Trp Val Ile Ile Lys Asp Gly Lys Val Ala Asn Tyr Gln Cys Val
545 550 555 560

Val Pro Thr Thr Trp Asn Gly Ser Pro Lys Asp Pro Lys Gly Gln His
565 570 575

Gly Ala Phe Glu Glu Ser Met Ile Asp Thr Lys Val Lys Val Pro Glu
580 585 590

Lys Pro Leu Glu Val Leu Arg Gly Ile His Ser Phe Asp Pro Cys Leu
595 600 605

Ala Cys Ser Thr His Leu Tyr Asn Glu Lys Gly Glu Glu Ile Ala Ser
610 615 620

Val Arg Val Gln Gly Val Val His Val
625 630

<210> SEQ ID NO 36
<211> LENGTH: 353
<212> TYPE: PRT
<213> ORGANISM: Aquifex aeolicus

<400> SEQUENCE: 36

Met Glu Thr Phe Trp Glu Val Phe Lys Arg His Gly Val Ser Arg Arg
1 5 10 15

Asp Phe Leu Lys Phe Ala Thr Thr Ile Thr Gly Leu Met Gly Leu Ala
20 25 30

Pro Ser Met Val Pro Glu Val Val Arg Ala Met Glu Thr Lys Pro Arg

```
        35                  40                  45

Val Pro Val Leu Trp Ile His Gly Leu Glu Cys Thr Cys Cys Ser Glu
    50                  55                  60

Ser Phe Ile Arg Ser Ala Thr Pro Leu Ala Ser Asp Val Val Leu Ser
65                  70                  75                  80

Met Ile Ser Leu Glu Tyr Asp Asp Thr Leu Ser Ala Ala Ala Gly Glu
                85                  90                  95

Ala Val Glu Lys His Arg Glu Arg Ile Ile Lys Glu Tyr Trp Gly Asn
            100                 105                 110

Tyr Ile Leu Ala Val Glu Gly Asn Pro Pro Leu Gly Glu Asp Gly Met
        115                 120                 125

Tyr Cys Ile Ile Gly Gly Arg Pro Phe Val Glu Ile Leu Lys Glu Ser
    130                 135                 140

Ala Glu Gly Ala Lys Ala Val Ile Ala Trp Gly Ser Cys Ala Ser Trp
145                 150                 155                 160

Gly Cys Val Gln Ala Ala Lys Pro Asn Pro Thr Thr Ala Val Pro Ile
                165                 170                 175

Asp Lys Val Ile Lys Asp Lys Pro Ile Ile Lys Val Pro Gly Cys Pro
            180                 185                 190

Pro Ile Ala Glu Val Met Thr Gly Val Ile Met Tyr Met Val Leu Phe
        195                 200                 205

Asp Arg Ile Pro Pro Leu Asp Ser Gln Gly Arg Pro Lys Met Phe Tyr
    210                 215                 220

Gly Asn Arg Ile His Asp Thr Cys Tyr Arg Arg Ser Phe Phe Asn Ala
225                 230                 235                 240

Gly Gln Phe Val Glu Gln Phe Asp Asp Glu Gly Ala Lys Lys Gly Trp
                245                 250                 255

Cys Leu Tyr Lys Val Gly Cys Arg Gly Pro Thr Thr Tyr Asn Ser Cys
            260                 265                 270

Gly Asn Met Arg Trp Tyr Asn Gly Leu Ser Tyr Pro Ile Gln Ser Gly
        275                 280                 285

His Gly Cys Ile Gly Cys Ala Glu Asn Asn Phe Trp Asp Asn Gly Pro
    290                 295                 300

Phe Tyr Glu Arg Ile Gly Gly Ile Pro Val Pro Gly Ile Glu Ser Lys
305                 310                 315                 320

Ala Asp Lys Val Gly Ala Ile Ala Ala Ala Ala Ala Ala Gly Gly Ala
                325                 330                 335

Ile Ile His Gly Ile Ala Ser Lys Ile Arg Lys Ser Gly Glu Lys Glu
            340                 345                 350

Glu


<210> SEQ ID NO 37
<211> LENGTH: 611
<212> TYPE: PRT
<213> ORGANISM: Hydrogenovibrio marinus

<400> SEQUENCE: 37

Met Ser Val Leu Asn Thr Pro Asn His Tyr Lys Met Asp Asn Ser Gly
1               5                   10                  15

Arg Arg Val Val Ile Asp Pro Val Thr Arg Ile Glu Gly His Met Arg
            20                  25                  30

Cys Glu Val Asn Val Asp Glu Asn Asn Val Ile Gln Asn Ala Val Ser
        35                  40                  45

Thr Gly Thr Met Trp Arg Gly Leu Glu Val Ile Leu Arg Gly Arg Asp
```

-continued

```
    50                  55                  60

Pro Arg Asp Ala Trp Ala Phe Val Glu Arg Ile Cys Gly Val Cys Thr
65                  70                  75                  80

Gly Cys His Ala Leu Ala Ser Val Arg Ala Val Glu Asp Ala Leu Asp
                85                  90                  95

Ile Lys Ile Pro His Asn Ala Thr Leu Ile Arg Glu Ile Met Ala Lys
            100                 105                 110

Thr Leu Gln Ile His Asp His Ile Val His Phe Tyr His Leu His Ala
        115                 120                 125

Leu Asp Trp Val Asn Pro Val Asn Ala Leu Lys Ala Asp Pro Gln Ala
    130                 135                 140

Thr Ser Glu Leu Gln Lys Leu Val Ser Pro His His Pro Met Ser Ser
145                 150                 155                 160

Pro Gly Tyr Phe Lys Asp Ile Gln Ile Arg Ile Gln Lys Phe Val Asp
                165                 170                 175

Ser Gly Gln Leu Gly Ile Phe Lys Asn Gly Tyr Trp Ser Asn Pro Ala
            180                 185                 190

Tyr Lys Leu Ser Pro Glu Ala Asp Leu Met Ala Val Thr His Tyr Leu
        195                 200                 205

Glu Ala Leu Asp Phe Gln Lys Glu Ile Val Lys Ile His Ala Ile Phe
    210                 215                 220

Gly Gly Lys Asn Pro His Pro Asn Tyr Met Val Gly Gly Val Pro Cys
225                 230                 235                 240

Ala Ile Asn Ile Asp Gly Asp Met Ala Ala Gly Ala Pro Ile Asn Met
                245                 250                 255

Glu Arg Leu Asn Phe Val Lys Ser Leu Ile Glu Gln Gly Arg Thr Phe
            260                 265                 270

Asn Thr Asn Val Tyr Val Pro Asp Val Ile Ala Ile Ala Ala Phe Tyr
        275                 280                 285

Arg Asp Trp Leu Tyr Gly Gly Gly Leu Ser Ala Thr Asn Val Met Asp
    290                 295                 300

Tyr Gly Ala Tyr Pro Lys Thr Pro Tyr Asp Lys Ser Thr Asp Gln Leu
305                 310                 315                 320

Pro Gly Gly Ala Ile Ile Asn Gly Asp Trp Gly Lys Ile His Pro Val
                325                 330                 335

Asp Pro Arg Asp Pro Glu Gln Val Gln Glu Phe Val Thr His Ser Trp
            340                 345                 350

Tyr Lys Tyr Pro Asp Glu Thr Lys Gly Leu His Pro Trp Asp Gly Ile
        355                 360                 365

Thr Glu Pro Asn Tyr Glu Leu Gly Ser Lys Thr Lys Gly Ser Arg Thr
    370                 375                 380

Asn Ile Ile Glu Ile Asp Glu Ser Ala Lys Tyr Ser Trp Ile Lys Ser
385                 390                 395                 400

Pro Arg Trp Arg Gly His Ala Val Glu Val Gly Pro Leu Ala Arg Tyr
                405                 410                 415

Ile Leu Ala Tyr Ala Gln Gly Val Glu Tyr Val Lys Thr Gln Val His
            420                 425                 430

Thr Ser Leu Asn Arg Phe Asn Ala Val Cys Arg Leu Leu Asp Pro Asn
        435                 440                 445

His Lys Asp Ile Thr Asp Leu Lys Ala Phe Leu Gly Ser Thr Ile Gly
    450                 455                 460

Arg Thr Leu Ala Arg Ala Leu Glu Ser Glu Tyr Cys Gly Asp Met Met
465                 470                 475                 480
```

```
Leu Asp Asp Phe Asn Gln Leu Ile Ser Asn Ile Lys Asn Gly Asp Ser
                485                 490                 495

Ser Thr Ala Asn Thr Asp Lys Trp Asp Pro Ser Ser Trp Pro Glu His
            500                 505                 510

Ala Lys Gly Val Gly Thr Val Ala Ala Pro Arg Gly Ala Leu Ala His
        515                 520                 525

Trp Ile Val Ile Glu Lys Gly Lys Ile Lys Asn Tyr Gln Cys Val Val
    530                 535                 540

Pro Thr Thr Trp Asn Gly Ser Pro Arg Asp Pro Lys Gly Asn Ile Gly
545                 550                 555                 560

Ala Phe Glu Ala Ser Leu Met Gly Thr Pro Met Glu Arg Pro Asp Glu
                565                 570                 575

Pro Val Glu Val Leu Arg Thr Leu His Ser Phe Asp Pro Cys Leu Ala
            580                 585                 590

Cys Ser Thr His Val Met Ser Glu Glu Gly Glu Glu Met Ala Thr Val
        595                 600                 605

Lys Val Arg
    610
```

<210> SEQ ID NO 38
<211> LENGTH: 361
<212> TYPE: PRT
<213> ORGANISM: Hydrogenovibrio marinus

<400> SEQUENCE: 38

```
Met Ser Ser Gln Val Glu Thr Phe Tyr Glu Val Met Arg Arg Gln Gly
1               5                   10                  15

Ile Thr Arg Arg Ser Phe Leu Lys Tyr Cys Ser Leu Thr Ala Ala Ala
            20                  25                  30

Leu Gly Leu Ser Pro Ala Tyr Ala Asn Lys Ile Ala His Ala Met Glu
        35                  40                  45

Thr Lys Pro Arg Thr Pro Val Ile Trp Leu His Gly Leu Glu Cys Thr
    50                  55                  60

Cys Cys Ser Glu Ser Phe Ile Arg Ser Ala His Pro Leu Ala Lys Asp
65                  70                  75                  80

Val Val Leu Ser Met Ile Ser Leu Asp Tyr Asp Asp Thr Leu Met Ala
                85                  90                  95

Ala Ser Gly His Ala Ala Glu Ala Ile Leu Asp Glu Ile Lys Glu Lys
            100                 105                 110

Tyr Lys Gly Asn Tyr Ile Leu Ala Val Glu Gly Asn Pro Pro Leu Asn
        115                 120                 125

Gln Asp Gly Met Ser Cys Ile Ile Gly Gly Arg Pro Phe Ser Glu Gln
    130                 135                 140

Leu Lys Arg Met Ala Asp Asp Ala Lys Ala Ile Ile Ser Trp Gly Ser
145                 150                 155                 160

Cys Ala Ser Trp Gly Cys Val Gln Ala Ala Lys Pro Asn Pro Thr Gln
                165                 170                 175

Ala Thr Pro Val His Lys Phe Leu Gly Gly Gly Tyr Asp Lys Pro Ile
            180                 185                 190

Ile Lys Val Pro Gly Cys Pro Pro Ile Ala Glu Val Met Thr Gly Val
        195                 200                 205

Ile Thr Tyr Met Leu Thr Phe Asp Arg Ile Pro Glu Leu Asp Arg Gln
    210                 215                 220

Gly Arg Pro Lys Met Phe Tyr Ser Gln Arg Ile His Asp Lys Cys Tyr
```

225 230 235 240

Arg Arg Pro His Phe Asp Ala Gly Gln Phe Val Glu Glu Trp Asp Asp
245 250 255

Glu Gly Ala Arg Lys Gly Tyr Cys Leu Tyr Lys Val Gly Cys Lys Gly
260 265 270

Pro Thr Thr Tyr Asn Ala Cys Ser Thr Val Arg Trp Asn Gly Gly Thr
275 280 285

Ser Phe Pro Ile Gln Ser Gly His Gly Cys Ile Gly Cys Ser Glu Asp
290 295 300

Gly Phe Trp Asp Lys Gly Ser Phe Tyr Ser Arg Asp Thr Glu Met Asn
305 310 315 320

Ala Phe Gly Ile Glu Ala Thr Ala Asp Asp Ile Gly Lys Thr Ala Ile
325 330 335

Gly Val Val Gly Ala Ala Val Val Ala His Ala Ala Ile Ser Ala Val
340 345 350

Lys Ala Ala Gln Lys Lys Gly Asp Lys
355 360

<210> SEQ ID NO 39
<211> LENGTH: 596
<212> TYPE: PRT
<213> ORGANISM: Thiocapsa roseopersicina

<400> SEQUENCE: 39

Met Ser Val Thr Thr Ala Asn Gly Phe Glu Leu Asp Thr Ala Gly Arg
1 5 10 15

Arg Leu Val Val Asp Pro Val Thr Arg Ile Glu Gly His Leu Arg Cys
20 25 30

Glu Val Asn Leu Asp Glu Asn Asn Val Ile Arg Asn Ala Val Ser Thr
35 40 45

Gly Thr Met Trp Arg Gly Leu Glu Val Ile Leu Arg Gly Arg Asp Pro
50 55 60

Arg Asp Ala Trp Ala Phe Thr Glu Arg Ile Cys Gly Val Cys Thr Gly
65 70 75 80

Thr His Ala Leu Thr Ser Val Arg Ala Val Glu Asp Ala Leu Gly Ile
85 90 95

Pro Ile Pro Glu Asn Ala Asn Ser Ile Arg Asn Ile Met His Val Thr
100 105 110

Leu Gln Ala His Asp His Leu Val His Phe Tyr His Leu His Ala Leu
115 120 125

Asp Trp Val Asp Val Val Ser Ala Leu Gly Ala Asp Pro Lys Ala Thr
130 135 140

Ser Ala Leu Ala Gln Ser Ile Ser Asp Trp Pro Lys Ser Ser Pro Gly
145 150 155 160

Tyr Phe Arg Asp Val Gln Asn Arg Leu Lys Arg Phe Val Glu Ser Gly
165 170 175

Gln Leu Gly Pro Phe Met Asn Gly Tyr Trp Gly Ser Pro Ala Tyr Lys
180 185 190

Leu Pro Pro Glu Ala Asn Leu Met Ala Val Thr His Tyr Leu Glu Ala
195 200 205

Leu Asp Phe Gln Lys Glu Ile Val Lys Ile His Thr Val Tyr Gly Gly
210 215 220

Lys Asn Pro His Pro Asn Trp Leu Val Gly Gly Met Pro Cys Ala Ile
225 230 235 240

```
Asn Val Asp Gly Thr Gly Ala Val Gly Ala Ile Asn Met Glu Arg Leu
                245                 250                 255

Asn Leu Val Ser Ser Ile Ile Asp Gln Thr Ile Ala Phe Ile Asp Lys
            260                 265                 270

Val Tyr Ile Pro Asp Leu Ile Ala Ile Ala Ser Phe Tyr Lys Asp Trp
        275                 280                 285

Thr Tyr Gly Gly Gly Leu Ser Ser Gln Ala Val Met Ser Tyr Gly Asp
    290                 295                 300

Ile Pro Asp His Ala Asn Asp Met Ser Ser Lys Asn Leu Leu Leu Pro
305                 310                 315                 320

Arg Gly Ala Ile Ile Asn Gly Asn Leu Asn Glu Ile His Glu Ile Asp
                325                 330                 335

Leu Arg Asn Pro Glu Glu Ile Gln Glu Phe Val Asp His Ser Trp Phe
            340                 345                 350

Ser Tyr Lys Asp Glu Thr Arg Gly Leu His Pro Trp Asp Gly Val Thr
        355                 360                 365

Glu Pro Asn Phe Val Leu Gly Pro Asn Ala Val Gly Ser Arg Thr Arg
    370                 375                 380

Ile Glu Ala Leu Asp Glu Gln Ala Lys Tyr Ser Trp Ile Lys Ala Pro
385                 390                 395                 400

Arg Trp Arg Gly His Ala Met Glu Val Gly Pro Leu Ala Arg Tyr Val
                405                 410                 415

Ile Gly Tyr Ala Lys Gly Ile Pro Glu Phe Lys Glu Pro Val Asp Lys
            420                 425                 430

Val Leu Thr Asp Leu Gly Gln Pro Leu Glu Ala Ile Phe Ser Thr Leu
        435                 440                 445

Gly Arg Thr Ala Ala Arg Gly Leu Glu Ala Ser Trp Ala Ala His Lys
    450                 455                 460

Met Arg Tyr Phe Gln Asp Lys Leu Val Ala Asn Ile Arg Ala Gly Asp
465                 470                 475                 480

Thr Ala Thr Ala Asn Val Asp Asn Trp Asp Pro Lys Thr Trp Pro Lys
                485                 490                 495

Glu Ala Arg Gly Val Gly Thr Thr Glu Ala Pro Arg Gly Ala Leu Gly
            500                 505                 510

His Trp Ile Val Ile Lys Asp Gly Lys Ile Asp Asn Tyr Gln Ala Val
        515                 520                 525

Val Pro Thr Thr Trp Asn Gly Ser Pro Arg Asp Pro Ala Gly Asn Ile
    530                 535                 540

Gly Ala Phe Glu Ala Ser Leu Leu Asn Thr Pro Leu Ala Lys Ala Asp
545                 550                 555                 560

Glu Pro Leu Glu Ile Leu Arg Thr Leu His Ser Phe Asp Pro Cys Leu
                565                 570                 575

Ala Cys Ala Thr His Ile Met Gly Pro Asp Gly Glu Glu Leu Thr Arg
            580                 585                 590

Ile Lys Val Arg
        595


<210> SEQ ID NO 40
<211> LENGTH: 360
<212> TYPE: PRT
<213> ORGANISM: Thiocapsa roseopersicina

<400> SEQUENCE: 40

Met Pro Thr Thr Glu Thr Tyr Tyr Glu Val Met Arg Arg Gln Gly Ile
1               5                   10                  15
```

-continued

```
Thr Arg Arg Ser Phe Leu Lys Phe Cys Ser Leu Thr Ala Thr Ala Leu
            20                  25                  30

Gly Leu Ser Pro Thr Phe Ala Gly Lys Ile Ala His Ala Met Glu Thr
        35                  40                  45

Lys Pro Arg Ile Pro Val Val Trp Leu His Gly Leu Glu Cys Thr Cys
    50                  55                  60

Cys Ser Glu Ser Phe Ile Arg Ser Ala His Pro Leu Val Ser Asp Val
65                  70                  75                  80

Ile Leu Ser Met Ile Ser Leu Asp Tyr Thr Ile Leu Ile Met Ala Ala
                85                  90                  95

Ala Gly His Gln Ala Glu Ala Ile Leu Glu Glu Val Arg His Lys His
            100                 105                 110

Ala Gly Asn Tyr Ile Leu Ala Val Glu Gly Asn Pro Pro Leu Asn Gln
        115                 120                 125

Asp Gly Met Ser Cys Ile Ile Gly Gly Arg Pro Phe Leu Glu Gln Leu
    130                 135                 140

Leu Glu Met Ala Asp Ser Cys Lys Ala Val Ile Ser Trp Gly Ser Cys
145                 150                 155                 160

Ala Ser Trp Gly Cys Val Gln Ala Ala Arg Pro Asn Pro Thr Arg Ala
                165                 170                 175

Thr Pro Val His Glu Val Ile Arg Asp Lys Pro Val Ile Lys Val Pro
            180                 185                 190

Gly Cys Pro Pro Ile Ala Glu Val Met Thr Gly Val Leu Thr Tyr Ile
        195                 200                 205

Leu Thr Phe Asp Arg Leu Pro Glu Leu Asp Arg Gln Gly Arg Pro Leu
    210                 215                 220

Met Phe Tyr Gly Gln Arg Ile His Asp Lys Cys Tyr Arg Arg Pro His
225                 230                 235                 240

Phe Asp Ala Gly Gln Phe Val Glu Ser Trp Asp Asp Glu Gly Ala Arg
                245                 250                 255

Arg Gly Tyr Cys Leu Tyr Lys Val Gly Cys Lys Gly Pro Thr Thr Tyr
            260                 265                 270

Asn Ala Cys Ser Thr Ile Arg Trp Asn Gly Gly Val Ser Phe Pro Ile
        275                 280                 285

Gln Ser Gly His Gly Cys Ile Gly Cys Ser Glu Asp Gly Phe Trp Asp
    290                 295                 300

Lys Gly Ser Phe Tyr Gln His Val Thr Asp Thr His Ala Phe Gly Ile
305                 310                 315                 320

Glu Ala Asn Ala Asp Arg Thr Gly Ile Ala Val Ala Thr Arg Arg Gly
                325                 330                 335

Ala Ala His Arg Ala His Ala Ala Val Ser Val Val Lys Arg Val Gln
            340                 345                 350

Gln Lys Lys Glu Glu Asp Gln Ser
        355                 360


<210> SEQ ID NO 41
<211> LENGTH: 332
<212> TYPE: PRT
<213> ORGANISM: Alteromonas macleodii

<400> SEQUENCE: 41

Met Ala Leu Pro Thr Leu Asn Lys Gln Leu Gln Ala Ser Gly Ile Ser
1               5                   10                  15

Arg Arg Thr Phe Leu Lys Phe Cys Ala Thr Thr Ala Ser Leu Leu Ala
```

20 25 30

Leu Pro Gln Ser Ala Val Ala Asp Leu Ala Thr Ala Leu Gly Asn Ala
35 40 45

Arg Arg Pro Ser Val Ile Trp Leu Pro Phe Gln Glu Cys Thr Gly Cys
50 55 60

Thr Glu Ala Ile Leu Arg Ser His Ala Pro Thr Leu Glu Ser Leu Ile
65 70 75 80

Phe Asp His Ile Ser Leu Asp Tyr Gln His Thr Ile Met Ala Ala Ala
85 90 95

Gly Glu Gln Ala Glu Asp Ala Arg Arg Ala Ala Met Asn Ala His Lys
100 105 110

Gly Gln Tyr Leu Leu Leu Val Asp Gly Ser Val Pro Val Gly Asn Pro
115 120 125

Gly Tyr Ser Thr Ile Ser Gly Met Ser Asn Val Asp Met Leu Arg Glu
130 135 140

Ser Ala Lys Asp Ala Ala Gly Ile Ile Ala Ile Gly Thr Cys Ala Ser
145 150 155 160

Phe Gly Gly Ile Pro Lys Ala Asn Pro Asn Pro Thr Gly Ala Val Ala
165 170 175

Val Ser Asp Ile Ile Thr Asp Lys Pro Ile Val Asn Ile Ser Gly Cys
180 185 190

Pro Pro Leu Pro Ile Ala Ile Thr Ala Val Leu Val His Tyr Leu Thr
195 200 205

Phe Lys Arg Phe Pro Asp Leu Asp Glu Leu Gln Arg Pro Leu Ala Phe
210 215 220

Phe Gly Glu Ser Ile His Asp Arg Cys Tyr Arg Arg Pro Phe Phe Glu
225 230 235 240

Gln Arg Lys Phe Ala Lys Ser Phe Asp Asp Glu Gly Ala Lys Asn Gly
245 250 255

Trp Cys Leu Phe Glu Leu Gly Cys Lys Gly Pro Glu Thr Phe Asn Ala
260 265 270

Cys Ala Thr Val Lys Trp Asn Gln Gly Thr Ser Phe Pro Ile Glu Ser
275 280 285

Gly His Pro Cys Leu Gly Cys Ser Glu Pro Asp Phe Trp Asp Lys Ser
290 295 300

Ser Phe Tyr Gln Ala Leu Gly Pro Trp Glu Trp Tyr Lys Ser Lys Pro
305 310 315 320

Gly Lys Gly Ala Gln Lys His Ala Gly Lys Asn Ser
325 330

<210> SEQ ID NO 42
<211> LENGTH: 625
<212> TYPE: PRT
<213> ORGANISM: Alteromonas macleodii

<400> SEQUENCE: 42

Met Glu Asn Thr Ala Ser Asn Asn Arg Leu Val Val Asp Pro Ile Thr
1 5 10 15

Arg Ile Glu Gly His Leu Arg Ile Glu Ala Glu Met Asp Gly Asn Thr
20 25 30

Ile Lys Gln Ala Phe Ser Ser Gly Thr Ser Val Arg Gly Ile Glu Leu
35 40 45

Ile Leu Gln Gly Arg Asp Pro Arg Asp Ala Trp Ala Phe Ala Gln Arg
50 55 60

-continued

```
Ile Cys Gly Val Cys Thr Leu Val His Gly Met Ala Ser Val Arg Ala
65                  70                  75                  80

Val Glu Asp Ala Ile Arg Lys Ala Trp Arg Ser Asn Ala Lys Leu Gly
                85                  90                  95

Val Ala Ile Gly Lys Pro Ser Met Thr Ser Met Pro Lys Gly Pro Met
            100                 105                 110

Gln His Gly Lys Lys Gly His Arg Gln Ser Arg Thr Ser Ile Gly Val
        115                 120                 125

Leu Ser Glu Ala Glu Met Ala Ile Pro Gln Asn Ala Gln Leu Ile Arg
    130                 135                 140

Asn Ile Met Ile Ala Thr Gln Tyr Val His Asp His Val Met His Phe
145                 150                 155                 160

Tyr His Leu His Ala Leu Asp Trp Val Asp Val Val Ser Ala Leu Asp
                165                 170                 175

Ala Asp Pro Thr Arg Thr Ala Thr Leu Ala Gly Gln Leu Ser Asp Tyr
            180                 185                 190

Pro Arg Ser Ser Pro Gly Tyr Phe Lys Asp Val Lys Gln Lys Val Lys
        195                 200                 205

Thr Leu Val Glu Ser Gly Gln Leu Gly Ile Phe Ser Asn Ala Tyr Trp
    210                 215                 220

Gly His Pro Gly Tyr Lys Leu Pro Pro Glu Val Asn Leu Met Ala Leu
225                 230                 235                 240

Ala His Tyr Leu Asp Ala Leu Thr Trp Gln Arg Glu Val Val Lys Val
                245                 250                 255

His Thr Ile Phe Gly Gly Lys Asn Pro His Pro Asn Phe Val Val Gly
            260                 265                 270

Gly Val Pro Ser Pro Ile Asn Leu Asn Ala Ser Thr Gly Ile Asn Thr
        275                 280                 285

Ser Arg Leu Val Gln Leu Gln Asp Ala Ile Thr Gln Met Lys Ser Phe
    290                 295                 300

Val Asp Gln Val Tyr Tyr Pro Asp Ile Val Ala Ile Ala Gly Tyr Tyr
305                 310                 315                 320

Lys Glu Trp Gly Thr Arg Gly Glu Gly Leu Gly Asn Phe Leu Thr Tyr
                325                 330                 335

Gly Asp Leu Pro Met Thr Ser Met Asp Asp Pro Asp Ser Phe Leu Phe
            340                 345                 350

Pro Arg Gly Ala Ile Leu Gly Arg Asp Leu Ser Lys Val His Asp Leu
        355                 360                 365

Asp Leu Asp Asp Pro Ser Glu Ile Gln Glu Phe Val Ser Ser Ser Trp
    370                 375                 380

Tyr Arg Tyr Ser Gly Gly Asn Ala Ser Gly Leu His Pro Phe Asn Gly
385                 390                 395                 400

Gln Thr Thr Leu Glu Tyr Thr Gly Pro Lys Pro Pro Tyr Lys His Leu
                405                 410                 415

Asn Val Gly Ala Glu Tyr Ser Trp Leu Lys Ser Pro Arg Trp Lys Gly
            420                 425                 430

His Ala Met Glu Val Gly Pro Leu Ala Arg Val Leu Met Met Tyr Ala
        435                 440                 445

Lys Lys Asp Ala Ala Ala Gln Asp Ile Val Asn Arg Ser Leu Ser Ile
    450                 455                 460

Leu Asp Leu Glu Thr Ser Ala Leu Phe Ser Thr Leu Gly Arg Thr Leu
465                 470                 475                 480

Ala Arg Ala Val Glu Thr Lys Ile Val Val Asn Gln Leu Gln Ser Trp
```

-continued 485 490 495

Tyr Asp Gln Leu Leu Asp Asn Ile Ala Lys Gly Asp Thr Asp Thr Phe
500 505 510

Asn Pro Leu Tyr Phe Asp Pro Thr Asn Trp Pro Ile Lys Gly Gln Gly
515 520 525

Val Gly Val Met Glu Ala Pro Arg Gly Ala Leu Gly His Trp Leu Val
530 535 540

Met Gln Asn Gly Lys Ile Glu Asn Tyr Gln Cys Val Val Pro Thr Thr
545 550 555 560

Trp Asn Ala Gly Pro Arg Asp Pro Asn Ser Gln Ala Gly Ala Tyr Glu
565 570 575

Ala Ala Leu Gln Asp Lys His Thr Leu His Asp Pro Asp Gln Pro Leu
580 585 590

Glu Ile Leu Arg Thr Leu His Ser Phe Asp Pro Cys Leu Ala Cys Ala
595 600 605

Val His Val Met Asp Glu Thr Gly Glu Glu Arg Leu Arg Leu Lys Val
610 615 620

Arg
625

<210> SEQ ID NO 43
<211> LENGTH: 488
<212> TYPE: PRT
<213> ORGANISM: Rhodococcus opacus

<400> SEQUENCE: 43

Met Ser Thr Lys Leu Val Ile Asp Pro Val Thr Arg Ile Glu Gly His
1 5 10 15

Gly Lys Val Thr Val His Leu Asp Asp Asn Asn Asn Val Val Asp Ala
20 25 30

His Leu His Val Val Glu Phe Arg Gly Phe Glu Lys Leu Val Gln Gly
35 40 45

His Pro Phe Trp Glu Ala Pro Met Leu Met Gln Arg Ile Cys Gly Ile
50 55 60

Cys Phe Val Ser His His Leu Cys Gly Ala Lys Ala Leu Asp Asp Met
65 70 75 80

Val Gly Val Gly Leu Lys Ser Gly Ile Asp Val Thr Pro Thr Ala Glu
85 90 95

Lys Ile Arg Arg Leu Gly His Tyr Ala Gln Met Leu Gln Ser His Ala
100 105 110

Thr Ala Tyr Phe Tyr Leu Ile Val Pro Glu Met Leu Phe Gly Met Asp
115 120 125

Ala Ala Pro Glu Gln Arg Asn Val Leu Gly Leu Ile Glu Ala Asn Pro
130 135 140

Glu Leu Val Lys Arg Val Val Met Leu Arg Lys Trp Gly Gln Glu Val
145 150 155 160

Ile Lys Ala Val Phe Gly Arg Arg Met His Gly Ile Ser Ser Val Pro
165 170 175

Gly Gly Val Asn Lys Asn Leu Ser Val Ala Glu Cys Gln Arg Phe Leu
180 185 190

Lys Gly Glu Glu Gly Leu Pro Ser Val Asp Glu Val Ile Glu Tyr Ala
195 200 205

Gln Glu Gly Val Gln Leu Phe Tyr Asp Phe His Glu Gln Asn Arg Val
210 215 220

Gln Val Asp Ser Phe Ala Asn Val Ser Ala Leu Ser Met Ser Leu Val
225 230 235 240

Asp Ala Asp Gly Asn Val Asp Tyr Tyr His Gly Lys Leu Arg Ile Ile
245 250 255

Asp Asp Asp Lys Asn Val Val Gln Glu Phe Asp Tyr His Asp Tyr Leu
260 265 270

Asp His Phe Ser Glu Ala Val Glu Glu Trp Ser Tyr Met Lys Phe Pro
275 280 285

Phe Leu Lys Ala Leu Gly Arg Glu Arg Gly Ser Val Arg Val Gly Pro
290 295 300

Leu Gly Arg Leu Asn Val Thr Asn Ser Leu Ser Thr Pro Leu Ala Gln
305 310 315 320

Glu Ala Leu Glu Arg Phe His Ala Tyr Thr Asn Gly Lys Ala Asn Asn
325 330 335

Met Thr Leu His Thr Asn Trp Ala Arg Ala Ile Glu Ile Leu His Ala
340 345 350

Ala Glu Leu Ile Lys Glu Leu Leu Asn Asp Pro Asp Leu Gln Lys Glu
355 360 365

Gln Leu Leu Leu Thr Pro Ala Asp Asn Ala Trp Thr Gly Glu Gly Val
370 375 380

Gly Val Val Glu Ala Pro Arg Gly Thr Leu Leu His His Tyr Arg Ala
385 390 395 400

Asp Gln Glu Gly Asp Ile Thr Phe Ala Asn Leu Val Val Ala Thr Thr
405 410 415

Gln Asn Asn Gln Val Met Asn Arg Thr Val Arg Ser Val Ala Glu Asp
420 425 430

Tyr Leu Gly Gly Gln Gly Glu Val Thr Glu Gly Met Met Asn Ala Ile
435 440 445

Glu Val Gly Ile Arg Ala Tyr Asp Pro Cys Leu Ser Cys Ala Thr His
450 455 460

Ala Leu Gly Gln Met Pro Leu Ile Val Ser Val His Asp Thr Glu Gly
465 470 475 480

His Val Ile Asn Glu Arg Val Arg
485

<210> SEQ ID NO 44
<211> LENGTH: 209
<212> TYPE: PRT
<213> ORGANISM: Rhodococcus opacus

<400> SEQUENCE: 44

Met Lys His Ser Glu Lys Asn Glu Ile Ala Ser His Glu Leu Pro Thr
1 5 10 15

Thr Pro Leu Asp Pro Val Leu Ala Ala Gly Arg Glu Ser Lys Ile Lys
20 25 30

Val Ala Met Ile Gly Leu Cys Gly Cys Trp Gly Cys Thr Leu Ser Phe
35 40 45

Leu Asp Met Asp Glu Arg Leu Leu Val Leu Leu Asp Lys Val Thr Leu
50 55 60

His Arg Ser Ser Leu Ser Asp Ile Lys Arg Ile Thr Glu Arg Cys Ala
65 70 75 80

Ile Gly Phe Ile Glu Gly Gly Val Ala Asn Glu Glu Asn Ile Glu Thr
85 90 95

Leu Glu His Tyr Arg Glu Asn Cys Asp Val Leu Ile Ser Val Gly Ala
100 105 110

```
Cys Ala Val Trp Gly Gly Val Pro Ala Met Arg Asn Val Phe Glu Leu
        115                 120                 125

Lys Asp Cys Leu Ser Glu Val Tyr Ile Asp Ser Ala Thr Ser Val Pro
    130                 135                 140

Gly Ala Lys Pro Val Val Pro Phe His Pro Asp Ile Pro Arg Ile Thr
145                 150                 155                 160

Asp Lys Val Tyr Pro Cys His Glu Val Val Lys Met Asp Tyr Phe Ile
                165                 170                 175

Pro Gly Cys Pro Pro Asp Ala Asp Ala Ile Phe Lys Val Leu Asp Asp
            180                 185                 190

Leu Val Asn Gly Arg Pro Phe Asp Leu Pro Ser Ser Ile Asn Gln Tyr
        195                 200                 205

Asp


<210> SEQ ID NO 45
<211> LENGTH: 576
<212> TYPE: PRT
<213> ORGANISM: Allochromatium vinosum

<400> SEQUENCE: 45

Met Ser Glu Arg Ile Val Val Asp Pro Val Thr Arg Ile Glu Gly His
1               5                   10                  15

Leu Arg Ile Glu Ala Gln Met Asp Gly Glu Asn Ile Ala Gln Ala Tyr
            20                  25                  30

Ser Ser Gly Thr Ser Val Arg Gly Leu Glu Thr Ile Leu Lys Gly Arg
        35                  40                  45

Asp Pro Arg Asp Ala Trp Ala Phe Ala Gln Arg Ile Cys Gly Val Cys
    50                  55                  60

Thr Leu Val His Gly Ile Ala Ser Val Arg Ser Val Glu Asp Ala Leu
65                  70                  75                  80

Lys Ile Glu Leu Pro Pro Asn Ala Gln Leu Ile Arg Asn Leu Met Ile
                85                  90                  95

Ser Ser Gln Phe Val His Asp His Val Met His Phe Tyr His Leu His
            100                 105                 110

Ala Leu Asp Trp Val Asp Val Val Ser Ala Leu Ser Ala Asp Pro Lys
        115                 120                 125

Ala Thr Ser Asp Leu Ala Gln Ser Ile Ser Ser Trp Pro Lys Ser Ser
    130                 135                 140

Pro Gly Tyr Phe Ala Asp Thr Gln Lys Arg Ile Lys Thr Phe Val Glu
145                 150                 155                 160

Ser Gly Gln Leu Gly Ile Phe Ala Asn Gly Tyr Trp Gly His Pro Ala
                165                 170                 175

Tyr Lys Leu Pro Pro Glu Ala Asn Leu Met Ala Val Ala His Tyr Leu
            180                 185                 190

Glu Ala Leu Ala Trp Gln Arg Asp Val Ala Arg Leu His Ala Ile Phe
        195                 200                 205

Gly Gly Lys Asn Pro His Pro Asn Phe Val Val Gly Gly Val Pro Ser
    210                 215                 220

Pro Ile Asp Ile Asp Ser Asp Ser Ala Ile Asn Ala Lys Arg Leu Ala
225                 230                 235                 240

Glu Val Gln Gln Ile Leu Gln Ser Met Gln Thr Phe Val Asp Gln Val
                245                 250                 255

Tyr Val Pro Asp Thr Leu Ala Ile Ala Ser Phe Tyr Lys Asp Trp Gly
            260                 265                 270
```

Glu Arg Gly Glu Gly Leu Gly Asn Phe Met Ser Tyr Gly Asp Leu Pro
275 280 285

Ala Thr Gly Thr Met Asp Pro Ala Gln Phe Leu Phe Pro Arg Gly Val
290 295 300

Ile Leu Asn Arg Asp Leu Ser Thr Ile His Glu Ile Asp Leu His Asp
305 310 315 320

Ala Gly Gln Ile Gln Glu Tyr Val Ala His Ser Trp Tyr Glu Tyr Ser
325 330 335

Gly Gly Asn Asp Gln Gly Leu His Pro Tyr Asp Gly Glu Thr Asn Leu
340 345 350

Glu Tyr Asp Ala Arg Gly Gly Val Lys Pro Pro Tyr Thr Gln Leu Asp
355 360 365

Val Asn Asp Gly Tyr Ser Trp Met Lys Ala Pro Arg Trp Lys Gly His
370 375 380

Ala Met Glu Val Gly Pro Leu Ala Arg Val Leu Leu Leu Tyr Ala Ser
385 390 395 400

Gly His Glu Gln Thr Lys Glu Leu Val Glu Met Thr Leu Thr Thr Leu
405 410 415

Asp Leu Pro Val Arg Ala Leu Tyr Ser Thr Leu Gly Arg Thr Ala Ala
420 425 430

Arg Thr Leu Glu Thr Lys Ile Leu Thr Asp Thr Ala Gln Asp Trp Tyr
435 440 445

Asn Gln Leu Ile Ala Asn Ile Lys Ala Gly Asp Ser Arg Thr Phe Asn
450 455 460

Glu Thr Leu Trp Glu Pro Ser Ser Trp Pro Ala Glu Ala Arg Gly Ala
465 470 475 480

Gly Tyr Met Glu Ala Pro Arg Gly Ala Leu Gly His Trp Ile Val Ile
485 490 495

Lys Asp Arg Lys Ile Ala Asn Tyr Gln Ala Val Val Pro Ser Thr Trp
500 505 510

Asn Ala Gly Pro Arg Asp Pro Ser Asp Gln Pro Gly Ala Tyr Glu Ala
515 520 525

Ala Leu Gln Asp Asn His Gln Leu Val Asp Val Lys Gln Pro Ile Glu
530 535 540

Ile Leu Arg Thr Ile His Ser Phe Asp Pro Cys Ile Ala Cys Ala Val
545 550 555 560

His Leu Thr Asp Pro Glu Thr Gly Glu Gln Met Glu Ile Lys Ile Thr
565 570 575

<210> SEQ ID NO 46
<211> LENGTH: 314
<212> TYPE: PRT
<213> ORGANISM: Allochromatium vinosum

<400> SEQUENCE: 46

Pro Ser Val Val Trp Leu Ser Phe Gln Glu Cys Thr Gly Cys Thr Glu
1 5 10 15

Ser Leu Thr Arg Ala His Ala Pro Thr Leu Glu Asp Leu Ile Leu Asp
20 25 30

Phe Ile Ser Leu Asp Tyr His His Thr Leu Gln Ala Ala Ser Gly Glu
35 40 45

Ala Ala Glu Ala Ala Arg Leu Gln Ala Met Asp Glu Asn Arg Gly Gln
50 55 60

Tyr Leu Val Ile Val Asp Gly Ser Ile Pro Gly Pro Asp Ala Asn Pro

```
65                  70                  75                  80

Gly Phe Ser Thr Val Ala Gly His Ser Asn Tyr Ser Ile Leu Met Glu
                85                  90                  95

Thr Val Glu His Ala Ala Ala Val Ile Ala Val Gly Thr Cys Ala Ala
            100                 105                 110

Phe Gly Gly Leu Pro Gln Ala Arg Pro Asn Pro Thr Gly Ala Met Ser
        115                 120                 125

Val Met Asp Leu Val Arg Asp Lys Pro Val Ile Asn Val Pro Gly Cys
    130                 135                 140

Pro Pro Ile Pro Met Val Ile Thr Gly Val Ile Ala His Tyr Leu Val
145                 150                 155                 160

Phe Gly Arg Leu Pro Glu Val Asp Gly Tyr Gly Arg Pro Leu Ala Phe
                165                 170                 175

Tyr Gly Gln Ser Ile His Asp Arg Cys Tyr Arg Arg Pro Phe Tyr Asp
            180                 185                 190

Lys Gly Leu Phe Ala Glu Ser Phe Asp Asp Glu Gly Ala Lys Gln Gly
        195                 200                 205

Trp Cys Leu Tyr Arg Leu Gly Cys Lys Gly Pro Thr Thr Tyr Asn Ala
    210                 215                 220

Cys Ala Thr Met Lys Trp Asn Asp Gly Thr Ser Trp Pro Val Glu Ala
225                 230                 235                 240

Gly His Pro Cys Leu Gly Cys Ser Glu Pro Gln Phe Trp Asp Ala Gly
                245                 250                 255

Gly Phe Tyr Glu Pro Val Ser Val Pro Leu Thr Leu Gly Pro Ala Thr
            260                 265                 270

Leu Leu Gly Ala Gly Ala Ala Gly Ala Val Val Gly Gly Gly Leu Ala
        275                 280                 285

Ala Leu Ser Arg Lys Lys Gly Arg Asp Ala Ala Ala Thr Arg Gln Pro
    290                 295                 300

Val Thr Val Asp Glu Leu Glu Gln Lys Leu
305                 310


<210> SEQ ID NO 47
<211> LENGTH: 564
<212> TYPE: PRT
<213> ORGANISM: Desulfovibrio fructosovorans

<400> SEQUENCE: 47

Met Ala Glu Ser Lys Pro Thr Pro Gln Ser Thr Phe Thr Gly Pro Ile
1               5                   10                  15

Val Val Asp Pro Ile Thr Arg Ile Glu Gly His Leu Arg Ile Met Val
            20                  25                  30

Glu Val Glu Asn Gly Lys Val Lys Asp Ala Trp Ser Ser Ser Gln Leu
        35                  40                  45

Phe Arg Gly Leu Glu Ile Ile Leu Lys Gly Arg Asp Pro Arg Asp Ala
    50                  55                  60

Gln His Phe Thr Gln Arg Ala Cys Gly Val Cys Thr Tyr Val His Ala
65                  70                  75                  80

Leu Ala Ser Ser Arg Cys Val Asp Asp Ala Val Lys Val Ser Ile Pro
                85                  90                  95

Ala Asn Ala Arg Met Met Arg Asn Leu Val Met Ala Ser Gln Tyr Leu
            100                 105                 110

His Asp His Leu Val His Phe Tyr His Leu His Ala Leu Asp Trp Val
        115                 120                 125
```

```
Asp Val Thr Ala Ala Leu Lys Ala Asp Pro Asn Lys Ala Ala Lys Leu
    130                 135                 140

Ala Ala Ser Ile Asp Thr Ala Arg Thr Gly Asn Ser Glu Lys Ala Leu
145                 150                 155                 160

Lys Ala Val Gln Asp Lys Leu Lys Ala Phe Val Glu Ser Gly Gln Leu
                165                 170                 175

Gly Ile Phe Thr Asn Ala Tyr Phe Leu Gly Gly His Lys Ala Tyr Tyr
            180                 185                 190

Leu Pro Pro Glu Val Asn Leu Ile Ala Thr Ala His Tyr Leu Glu Ala
        195                 200                 205

Leu His Met Gln Val Lys Ala Ala Ser Ala Met Ala Ile Leu Gly Gly
    210                 215                 220

Lys Asn Pro His Thr Gln Phe Thr Val Val Gly Gly Cys Ser Asn Tyr
225                 230                 235                 240

Gln Gly Leu Thr Lys Asp Pro Leu Ala Asn Tyr Leu Ala Leu Ser Lys
                245                 250                 255

Glu Val Cys Gln Phe Val Asn Glu Cys Tyr Ile Pro Asp Leu Leu Ala
            260                 265                 270

Val Ala Gly Phe Tyr Lys Asp Trp Gly Gly Ile Gly Gly Thr Ser Asn
        275                 280                 285

Tyr Leu Ala Phe Gly Glu Phe Ala Thr Asp Asp Ser Ser Pro Glu Lys
    290                 295                 300

His Leu Ala Thr Ser Gln Phe Pro Ser Gly Val Ile Thr Gly Arg Asp
305                 310                 315                 320

Leu Gly Lys Val Asp Asn Val Asp Leu Gly Ala Ile Tyr Glu Asp Val
                325                 330                 335

Lys Tyr Ser Trp Tyr Ala Pro Gly Gly Asp Gly Lys His Pro Tyr Asp
            340                 345                 350

Gly Val Thr Asp Pro Lys Tyr Thr Lys Leu Asp Asp Lys Asp His Tyr
        355                 360                 365

Ser Trp Met Lys Ala Pro Arg Tyr Lys Gly Lys Ala Met Glu Val Gly
    370                 375                 380

Pro Leu Ala Arg Thr Phe Ile Ala Tyr Ala Lys Gly Gln Pro Asp Phe
385                 390                 395                 400

Lys Lys Val Val Asp Met Val Leu Gly Lys Leu Ser Val Pro Ala Thr
                405                 410                 415

Ala Leu His Ser Thr Leu Gly Arg Thr Ala Ala Arg Gly Ile Glu Thr
            420                 425                 430

Ala Ile Val Cys Ala Asn Met Glu Lys Trp Ile Lys Glu Met Ala Asp
        435                 440                 445

Ser Gly Ala Lys Asp Asn Thr Leu Cys Ala Lys Trp Glu Met Pro Glu
    450                 455                 460

Glu Ser Lys Gly Val Gly Leu Ala Asp Ala Pro Arg Gly Ser Leu Ser
465                 470                 475                 480

His Trp Ile Arg Ile Lys Gly Lys Lys Ile Asp Asn Phe Gln Leu Val
                485                 490                 495

Val Pro Ser Thr Trp Asn Leu Gly Pro Arg Gly Pro Gln Gly Asp Lys
            500                 505                 510

Ser Pro Val Glu Glu Ala Leu Ile Gly Thr Pro Ile Ala Asp Pro Lys
        515                 520                 525

Arg Pro Val Glu Ile Leu Arg Thr Val His Ala Phe Asp Pro Cys Ile
    530                 535                 540

Ala Cys Gly Val His Val Ile Glu Pro Glu Thr Asn Glu Ile Leu Lys
```

545 550 555 560

Phe Lys Val Cys

<210> SEQ ID NO 48
<211> LENGTH: 314
<212> TYPE: PRT
<213> ORGANISM: Desulfovibrio fructosovorans

<400> SEQUENCE: 48

```
Met Asn Phe Ser Val Gly Leu Gly Arg Asp Asp Ala Glu Lys Arg Leu
1               5                   10                  15

Val Gln Asn Gly Val Ser Arg Arg Asp Phe Met Lys Phe Cys Ala Thr
            20                  25                  30

Val Ala Ala Ala Met Gly Met Gly Pro Ala Phe Ala Pro Lys Val Ala
        35                  40                  45

Glu Ala Leu Thr Ala Lys His Arg Pro Ser Val Val Trp Leu His Asn
    50                  55                  60

Ala Glu Cys Thr Gly Cys Thr Glu Ala Ala Ile Arg Thr Ile Lys Pro
65                  70                  75                  80

Tyr Ile Asp Ala Leu Ile Leu Asp Thr Ile Ser Leu Asp Tyr Gln Glu
                85                  90                  95

Thr Ile Met Ala Ala Ala Gly Glu Ala Ala Glu Ala Ala Leu His Gln
            100                 105                 110

Ala Leu Glu Gly Lys Asp Gly Tyr Tyr Leu Val Val Glu Gly Gly Leu
        115                 120                 125

Pro Thr Ile Asp Gly Gly Gln Trp Gly Met Val Ala Gly His Pro Met
    130                 135                 140

Ile Glu Thr Thr Lys Lys Ala Ala Ala Lys Ala Lys Gly Ile Ile Cys
145                 150                 155                 160

Ile Gly Thr Cys Ser Ala Tyr Gly Gly Val Gln Lys Ala Lys Pro Asn
                165                 170                 175

Pro Ser Gln Ala Lys Gly Val Ser Glu Ala Leu Gly Val Lys Thr Ile
            180                 185                 190

Asn Ile Pro Gly Cys Pro Pro Asn Pro Ile Asn Phe Val Gly Ala Val
        195                 200                 205

Val His Val Leu Thr Lys Gly Ile Pro Asp Leu Asp Glu Asn Gly Arg
    210                 215                 220

Pro Lys Leu Phe Tyr Gly Glu Leu Val His Asp Asn Cys Pro Arg Leu
225                 230                 235                 240

Pro His Phe Glu Ala Ser Glu Phe Ala Pro Ser Phe Asp Ser Glu Glu
                245                 250                 255

Ala Lys Lys Gly Phe Cys Leu Tyr Glu Leu Gly Cys Lys Gly Pro Val
            260                 265                 270

Thr Tyr Asn Asn Cys Pro Lys Val Leu Phe Asn Gln Val Asn Trp Pro
        275                 280                 285

Val Gln Ala Gly His Pro Cys Leu Gly Cys Ser Glu Pro Asp Phe Trp
    290                 295                 300

Asp Thr Met Thr Pro Phe Tyr Glu Gln Gly
305                 310
```

<210> SEQ ID NO 49
<211> LENGTH: 574
<212> TYPE: PRT
<213> ORGANISM: Clostridium pasteurianum

<400> SEQUENCE: 49

-continued

```
Met Lys Thr Ile Ile Ile Asn Gly Val Gln Phe Asn Thr Asp Glu Asp
1               5                   10                  15

Thr Thr Ile Leu Lys Phe Ala Arg Asp Asn Asn Ile Asp Ile Ser Ala
            20                  25                  30

Leu Cys Phe Leu Asn Asn Cys Asn Asn Asp Ile Asn Lys Cys Glu Ile
        35                  40                  45

Cys Thr Val Glu Val Glu Gly Thr Gly Leu Val Thr Ala Cys Asp Thr
    50                  55                  60

Leu Ile Glu Asp Gly Met Ile Ile Asn Thr Asn Ser Asp Ala Val Asn
65                  70                  75                  80

Glu Lys Ile Lys Ser Arg Ile Ser Gln Leu Leu Asp Ile His Glu Phe
                85                  90                  95

Lys Cys Gly Pro Cys Asn Arg Arg Glu Asn Cys Glu Phe Leu Lys Leu
            100                 105                 110

Val Ile Lys Tyr Lys Ala Arg Ala Ser Lys Pro Phe Leu Pro Lys Asp
        115                 120                 125

Lys Thr Glu Tyr Val Asp Glu Arg Ser Lys Ser Leu Thr Val Asp Arg
    130                 135                 140

Thr Lys Cys Leu Leu Cys Gly Arg Cys Val Asn Ala Cys Gly Lys Asn
145                 150                 155                 160

Thr Glu Thr Tyr Ala Met Lys Phe Leu Asn Lys Asn Gly Lys Thr Ile
                165                 170                 175

Ile Gly Ala Glu Asp Glu Lys Cys Phe Asp Asp Thr Asn Cys Leu Leu
            180                 185                 190

Cys Gly Gln Cys Ile Ile Ala Cys Pro Val Ala Ala Leu Ser Glu Lys
        195                 200                 205

Ser His Met Asp Arg Val Lys Asn Ala Leu Asn Ala Pro Glu Lys His
    210                 215                 220

Val Ile Val Ala Met Ala Pro Ser Val Arg Ala Ser Ile Gly Glu Leu
225                 230                 235                 240

Phe Asn Met Gly Phe Gly Val Asp Val Thr Gly Lys Ile Tyr Thr Ala
                245                 250                 255

Leu Arg Gln Leu Gly Phe Asp Lys Ile Phe Asp Ile Asn Phe Gly Ala
            260                 265                 270

Asp Met Thr Ile Met Glu Glu Ala Thr Glu Leu Val Gln Arg Ile Glu
        275                 280                 285

Asn Asn Gly Pro Phe Pro Met Phe Thr Ser Cys Cys Pro Gly Trp Val
    290                 295                 300

Arg Gln Ala Glu Asn Tyr Tyr Pro Glu Leu Leu Asn Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Leu Asp Pro Lys Asn Val Phe Thr Val Thr Val
            340                 345                 350

Met Pro Cys Thr Ser Lys Lys Phe Glu Ala Asp Arg Pro Gln Met Glu
        355                 360                 365

Lys Asp Gly Leu Arg Asp Ile Asp Ala Val Ile Thr Thr Arg Glu Leu
    370                 375                 380

Ala Lys Met Ile Lys Asp Ala Lys Ile Pro Phe Ala Lys Leu Glu Asp
385                 390                 395                 400

Ser Glu Ala Asp Pro Ala Met Gly Glu Tyr Ser Gly Ala Gly Ala Ile
                405                 410                 415
```

-continued

Phe Gly Ala Thr Gly Gly Val Met Glu Ala Ala Leu Arg Ser Ala Lys
420 425 430

Asp Phe Ala Glu Asn Ala Glu Leu Glu Asp Ile Glu Tyr Lys Gln Val
435 440 445

Arg Gly Leu Asn Gly Ile Lys Glu Ala Glu Val Glu Ile Asn Asn Asn
450 455 460

Lys Tyr Asn Val Ala Val Ile Asn Gly Ala Ser Asn Leu Phe Lys Phe
465 470 475 480

Met Lys Ser Gly Met Ile Asn Glu Lys Gln Tyr His Phe Ile Glu Val
485 490 495

Met Ala Cys His Gly Gly Cys Val Asn Gly Gly Gly Gln Pro His Val
500 505 510

Asn Pro Lys Asp Leu Glu Lys Val Asp Ile Lys Lys Val Arg Ala Ser
515 520 525

Val Leu Tyr Asn Gln Asp Glu His Leu Ser Lys Arg Lys Ser His Glu
530 535 540

Asn Thr Ala Leu Val Lys Met Tyr Gln Asn Tyr Phe Gly Lys Pro Gly
545 550 555 560

Glu Gly Arg Ala His Glu Ile Leu His Phe Lys Tyr Lys Lys
565 570

<210> SEQ ID NO 50
<211> LENGTH: 582
<212> TYPE: PRT
<213> ORGANISM: Clostridium acetobutylicum

<400> SEQUENCE: 50

Met Lys Thr Ile Ile Leu Asn Gly Asn Glu Val His Thr Asp Lys Asp
1 5 10 15

Ile Thr Ile Leu Glu Leu Ala Arg Glu Asn Asn Val Asp Ile Pro Thr
20 25 30

Leu Cys Phe Leu Lys Asp Cys Gly Asn Phe Gly Lys Cys Gly Val Cys
35 40 45

Met Val Glu Val Glu Gly Lys Gly Phe Arg Ala Ala Cys Val Ala Lys
50 55 60

Val Glu Asp Gly Met Val Ile Asn Thr Glu Ser Asp Glu Val Lys Glu
65 70 75 80

Arg Ile Lys Lys Arg Val Ser Met Leu Leu Asp Lys His Glu Phe Lys
85 90 95

Cys Gly Gln Cys Ser Arg Arg Glu Asn Cys Glu Phe Leu Lys Leu Val
100 105 110

Ile Lys Thr Lys Ala Lys Ala Ser Lys Pro Phe Leu Pro Glu Asp Lys
115 120 125

Asp Ala Leu Val Asp Asn Arg Ser Lys Ala Ile Val Ile Asp Arg Ser
130 135 140

Lys Cys Val Leu Cys Gly Arg Cys Val Ala Ala Cys Lys Gln His Thr
145 150 155 160

Ser Thr Cys Ser Ile Gln Phe Ile Lys Lys Asp Gly Gln Arg Ala Val
165 170 175

Gly Thr Val Asp Asp Val Cys Leu Asp Asp Ser Thr Cys Leu Leu Cys
180 185 190

Gly Gln Cys Val Ile Ala Cys Pro Val Ala Ala Leu Lys Glu Lys Ser
195 200 205

His Ile Glu Lys Val Gln Glu Ala Leu Asn Asp Pro Lys Lys His Val
210 215 220

```
Ile Val Ala Met Ala Pro Ser Val Arg Thr Ala Met Gly Glu Leu Phe
225                 230                 235                 240

Lys Met Gly Tyr Gly Lys Asp Val Thr Gly Lys Leu Tyr Thr Ala Leu
                245                 250                 255

Arg Met Leu Gly Phe Asp Lys Val Phe Asp Ile Asn Phe Gly Ala Asp
            260                 265                 270

Met Thr Ile Met Glu Glu Ala Thr Glu Leu Leu Gly Arg Val Lys Asn
        275                 280                 285

Asn Gly Pro Phe Pro Met Phe Thr Ser Cys Cys Pro Ala Trp Val Arg
    290                 295                 300

Leu Ala Gln Asn Tyr His Pro Glu Leu Leu Asp Asn Leu Ser Ser Ala
305                 310                 315                 320

Lys Ser Pro Gln Gln Ile Phe Gly Thr Ala Ser Lys Thr Tyr Tyr Pro
                325                 330                 335

Ser Ile Ser Gly Ile Ala Pro Glu Asp Val Tyr Thr Val Thr Ile Met
            340                 345                 350

Pro Cys Asn Asp Lys Lys Tyr Glu Ala Asp Ile Pro Phe Met Glu Thr
        355                 360                 365

Asn Ser Leu Arg Asp Ile Asp Ala Ser Leu Thr Thr Arg Glu Leu Ala
    370                 375                 380

Lys Met Ile Lys Asp Ala Lys Ile Lys Phe Ala Asp Leu Glu Asp Gly
385                 390                 395                 400

Glu Val Asp Pro Ala Met Gly Thr Tyr Ser Gly Ala Gly Ala Ile Phe
                405                 410                 415

Gly Ala Thr Gly Gly Val Met Glu Ala Ala Ile Arg Ser Ala Lys Asp
            420                 425                 430

Phe Ala Glu Asn Lys Glu Leu Glu Asn Val Asp Tyr Thr Glu Val Arg
        435                 440                 445

Gly Phe Lys Gly Ile Lys Glu Ala Glu Val Glu Ile Ala Gly Asn Lys
    450                 455                 460

Leu Asn Val Ala Val Ile Asn Gly Ala Ser Asn Phe Phe Glu Phe Met
465                 470                 475                 480

Lys Ser Gly Lys Met Asn Glu Lys Gln Tyr His Phe Ile Glu Val Met
                485                 490                 495

Ala Cys Pro Gly Gly Cys Ile Asn Gly Gly Gly Gln Pro His Val Asn
            500                 505                 510

Ala Leu Asp Arg Glu Asn Val Asp Tyr Arg Lys Leu Arg Ala Ser Val
        515                 520                 525

Leu Tyr Asn Gln Asp Lys Asn Val Leu Ser Lys Arg Lys Ser His Asp
    530                 535                 540

Asn Pro Ala Ile Ile Lys Met Tyr Asp Ser Tyr Phe Gly Lys Pro Gly
545                 550                 555                 560

Glu Gly Leu Ala His Lys Leu Leu His Val Lys Tyr Thr Lys Asp Lys
                565                 570                 575

Asn Val Ser Lys His Glu
            580
```

<210> SEQ ID NO 51
<211> LENGTH: 505
<212> TYPE: PRT
<213> ORGANISM: Chlamydomonas reinhardtii

<400> SEQUENCE: 51

```
Met Ala Leu Gly Leu Leu Ala Glu Leu Arg Ala Gly Gln Ala Val Ala
```

-continued

```
1               5                   10                  15

Cys Ala Arg Arg Thr Asn Ala Pro Ala His Pro Ala Ala Val Val Pro
            20                  25                  30

Cys Leu Pro Ser Arg Ala Gly Lys Phe Phe Asn Leu Ser Gln Lys Val
        35                  40                  45

Pro Ser Ser Gln Ser Ala Arg Gly Ser Thr Ile Arg Val Ala Ala Thr
    50                  55                  60

Ala Thr Asp Ala Val Pro His Trp Lys Leu Ala Leu Glu Glu Leu Asp
65                  70                  75                  80

Lys Pro Lys Asp Gly Gly Arg Lys Val Leu Ile Ala Gln Val Ala Pro
                85                  90                  95

Ala Val Arg Val Ala Ile Ala Glu Ser Phe Gly Leu Ala Pro Gly Ala
            100                 105                 110

Val Ser Pro Gly Lys Leu Ala Thr Gly Leu Arg Ala Leu Gly Phe Asp
        115                 120                 125

Gln Val Phe Asp Thr Leu Phe Ala Ala Asp Leu Thr Ile Met Glu Glu
    130                 135                 140

Gly Thr Glu Leu Leu His Arg Leu Lys Glu His Leu Glu Ala His Pro
145                 150                 155                 160

His Ser Asp Glu Pro Leu Pro Met Phe Thr Ser Cys Cys Pro Gly Trp
                165                 170                 175

Val Ala Met Met Glu Lys Ser Tyr Pro Glu Leu Ile Pro Phe Val Ser
            180                 185                 190

Ser Cys Lys Ser Pro Gln Met Met Met Gly Ala Met Val Lys Thr Tyr
        195                 200                 205

Leu Ser Glu Lys Gln Gly Ile Pro Ala Lys Asp Ile Val Met Val Ser
    210                 215                 220

Val Met Pro Cys Val Arg Lys Gln Gly Glu Ala Asp Arg Glu Trp Phe
225                 230                 235                 240

Cys Val Ser Glu Pro Gly Val Arg Asp Val Asp His Val Ile Thr Thr
                245                 250                 255

Ala Glu Leu Gly Asn Ile Phe Lys Glu Arg Gly Ile Asn Leu Pro Glu
            260                 265                 270

Leu Pro Asp Ser Asp Trp Asp Gln Pro Leu Gly Leu Gly Ser Gly Ala
        275                 280                 285

Gly Val Leu Phe Gly Thr Thr Gly Gly Val Met Glu Ala Ala Leu Arg
    290                 295                 300

Thr Ala Tyr Glu Ile Val Thr Lys Glu Pro Leu Pro Arg Leu Asn Leu
305                 310                 315                 320

Ser Glu Val Arg Gly Leu Asp Gly Ile Lys Glu Ala Ser Val Thr Leu
                325                 330                 335

Val Pro Ala Pro Gly Ser Lys Phe Ala Glu Leu Val Ala Glu Arg Leu
            340                 345                 350

Ala His Lys Val Glu Glu Ala Ala Ala Ala Glu Ala Ala Ala Ala Val
        355                 360                 365

Glu Gly Ala Val Lys Pro Pro Ile Ala Tyr Asp Gly Gly Gln Gly Phe
    370                 375                 380

Ser Thr Asp Asp Gly Lys Gly Gly Leu Lys Leu Arg Val Ala Val Ala
385                 390                 395                 400

Asn Gly Leu Gly Asn Ala Lys Lys Leu Ile Gly Lys Met Val Ser Gly
                405                 410                 415

Glu Ala Lys Tyr Asp Phe Val Glu Ile Met Ala Cys Pro Ala Gly Cys
            420                 425                 430
```

Val Gly Gly Gly Gly Gln Pro Arg Ser Thr Asp Lys Gln Ile Thr Gln
435 440 445

Lys Arg Gln Ala Ala Leu Tyr Asp Leu Asp Glu Arg Asn Thr Leu Arg
450 455 460

Arg Ser His Glu Asn Glu Ala Val Asn Gln Leu Tyr Lys Glu Phe Leu
465 470 475 480

Gly Glu Pro Leu Ser His Arg Ala His Glu Leu Leu His Thr His Tyr
485 490 495

Val Pro Gly Gly Ala Glu Ala Asp Ala
500 505

<210> SEQ ID NO 52
<211> LENGTH: 514
<212> TYPE: PRT
<213> ORGANISM: Desulfomicrobium baculatus
<220> FEATURE:
<221> NAME/KEY: SITE
<222> LOCATION: (493)..(493)
<223> OTHER INFORMATION: Xaa is selenocysteine

<400> SEQUENCE: 52

Met Ser Gln Ala Ala Thr Pro Ala Ala Asp Gly Lys Val Lys Ile Ser
1 5 10 15

Ile Asp Pro Leu Thr Arg Val Glu Gly His Leu Lys Ile Glu Val Glu
20 25 30

Val Lys Asp Gly Lys Val Val Asp Ala Lys Cys Ser Gly Gly Met Phe
35 40 45

Arg Gly Phe Glu Gln Ile Leu Arg Gly Arg Asp Pro Arg Asp Ser Ser
50 55 60

Gln Ile Val Gln Arg Ile Cys Gly Val Cys Pro Thr Ala His Cys Thr
65 70 75 80

Ala Ser Val Met Ala Gln Asp Asp Ala Phe Gly Val Lys Val Thr Thr
85 90 95

Asn Gly Arg Ile Thr Arg Asn Leu Ile Phe Gly Ala Asn Tyr Leu Gln
100 105 110

Ser His Ile Leu His Phe Tyr His Leu Ala Ala Leu Asp Tyr Val Lys
115 120 125

Gly Pro Asp Val Ser Pro Phe Val Pro Arg Tyr Ala Asn Ala Asp Leu
130 135 140

Leu Thr Asp Arg Ile Lys Asp Gly Ala Lys Ala Asp Ala Thr Asn Thr
145 150 155 160

Tyr Gly Leu Asn Gln Tyr Leu Lys Ala Leu Glu Ile Arg Arg Ile Cys
165 170 175

His Glu Met Val Ala Met Phe Gly Gly Arg Met Pro His Val Gln Gly
180 185 190

Met Val Val Gly Gly Ala Thr Glu Ile Pro Thr Ala Asp Lys Val Ala
195 200 205

Glu Tyr Ala Ala Arg Phe Lys Glu Val Gln Lys Phe Val Ile Glu Glu
210 215 220

Tyr Leu Pro Leu Ile Tyr Thr Leu Gly Ser Val Tyr Thr Asp Leu Phe
225 230 235 240

Glu Thr Gly Ile Gly Trp Lys Asn Val Ile Ala Phe Gly Val Phe Pro
245 250 255

Glu Asp Asp Asp Tyr Lys Thr Phe Leu Leu Lys Pro Gly Val Tyr Ile
260 265 270

```
Asp Gly Lys Asp Glu Glu Phe Asp Ser Lys Leu Val Lys Glu Tyr Val
        275                 280                 285

Gly His Ser Phe Phe Asp His Ser Ala Pro Gly Gly Leu His Tyr Ser
    290                 295                 300

Val Gly Glu Thr Asn Pro Asn Pro Asp Lys Pro Gly Ala Tyr Ser Phe
305                 310                 315                 320

Val Lys Ala Pro Arg Tyr Lys Asp Lys Pro Cys Glu Val Gly Pro Leu
                325                 330                 335

Ala Arg Met Trp Val Gln Asn Pro Glu Leu Ser Pro Val Gly Gln Lys
            340                 345                 350

Leu Leu Lys Glu Leu Tyr Gly Ile Glu Ala Lys Lys Phe Arg Asp Leu
        355                 360                 365

Gly Asp Lys Ala Phe Ser Ile Met Gly Arg His Val Leu Val Ala Glu
    370                 375                 380

Glu Thr Trp Leu Thr Ala Val Ala Val Glu Lys Trp Leu Lys Gln Val
385                 390                 395                 400

Gln Pro Gly Ala Glu Thr Tyr Val Lys Ser Glu Ile Pro Asp Ala Ala
                405                 410                 415

Glu Gly Thr Gly Phe Thr Glu Ala Pro Arg Gly Ala Leu Leu His Tyr
            420                 425                 430

Leu Lys Ile Lys Asp Lys Lys Ile Glu Asn Tyr Gln Ile Val Ser Ala
        435                 440                 445

Thr Leu Trp Asn Ala Asn Pro Arg Asp Asp Met Gly Gln Arg Gly Pro
    450                 455                 460

Ile Glu Glu Ala Leu Ile Gly Val Pro Val Pro Asp Ile Lys Asn Pro
465                 470                 475                 480

Val Asn Val Gly Arg Leu Val Arg Ser Tyr Asp Pro Xaa Leu Gly Cys
                485                 490                 495

Ala Val His Val Leu His Ala Glu Thr Gly Glu Glu His Val Val Asn
            500                 505                 510

Ile Asp


<210> SEQ ID NO 53
<211> LENGTH: 315
<212> TYPE: PRT
<213> ORGANISM: Desulfomicrobium baculatus

<400> SEQUENCE: 53

Met Ser Leu Ser Arg Arg Glu Phe Val Lys Leu Cys Ser Ala Gly Val
1               5                   10                  15

Ala Gly Leu Gly Ile Ser Gln Ile Tyr His Pro Gly Ile Val His Ala
            20                  25                  30

Met Thr Glu Gly Ala Lys Lys Ala Pro Val Ile Trp Val Gln Gly Gln
        35                  40                  45

Gly Cys Thr Gly Cys Ser Val Ser Leu Leu Asn Ala Val His Pro Arg
    50                  55                  60

Ile Lys Glu Ile Leu Leu Asp Val Ile Ser Leu Glu Phe His Pro Thr
65                  70                  75                  80

Val Met Ala Ser Glu Gly Glu Met Ala Leu Ala His Met Tyr Glu Ile
                85                  90                  95

Ala Glu Lys Phe Asn Gly Asn Phe Phe Leu Leu Val Glu Gly Ala Ile
            100                 105                 110

Pro Thr Ala Lys Glu Gly Arg Tyr Cys Ile Val Gly Glu Thr Leu Asp
        115                 120                 125
```

```
Ala Lys Gly His His His Glu Val Thr Met Met Glu Leu Ile Arg Asp
    130                 135                 140

Leu Ala Pro Lys Ser Leu Ala Thr Val Ala Val Gly Thr Cys Ser Ala
145                 150                 155                 160

Tyr Gly Gly Ile Pro Ala Ala Glu Gly Asn Val Thr Gly Ser Lys Ser
                165                 170                 175

Val Arg Asp Phe Phe Ala Asp Glu Lys Ile Glu Lys Leu Leu Val Asn
            180                 185                 190

Val Pro Gly Cys Pro Pro His Pro Asp Trp Met Val Gly Thr Leu Val
        195                 200                 205

Ala Ala Trp Ser His Val Leu Asn Pro Thr Glu His Pro Leu Pro Glu
    210                 215                 220

Leu Asp Asp Asp Gly Arg Pro Leu Leu Phe Phe Gly Asp Asn Ile His
225                 230                 235                 240

Glu Asn Cys Pro Tyr Leu Asp Lys Tyr Asp Asn Ser Glu Phe Ala Glu
                245                 250                 255

Thr Phe Thr Lys Pro Gly Cys Lys Ala Glu Leu Gly Cys Lys Gly Pro
            260                 265                 270

Ser Thr Tyr Ala Asp Cys Ala Lys Arg Arg Trp Asn Asn Gly Ile Asn
        275                 280                 285

Trp Cys Val Glu Asn Ala Val Cys Ile Gly Cys Val Glu Pro Asp Phe
    290                 295                 300

Pro Asp Gly Lys Ser Pro Phe Tyr Val Ala Glu
305                 310                 315


<210> SEQ ID NO 54
<211> LENGTH: 602
<212> TYPE: PRT
<213> ORGANISM: Artificial Sequence
<220> FEATURE:
<223> OTHER INFORMATION: Synthetic sequence

<400> SEQUENCE: 54

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175
```

-continued

Ser Asn Val Arg Thr Lys Gly Pro Val Phe Phe Arg Gly Arg Thr Asp
180 185 190

Leu Arg Ser Leu Leu Asp Gln Cys Leu Leu Leu Lys Pro Glu Gln Val
195 200 205

Ile Glu Thr Ile Val Asp Ser Arg Leu Arg Gly Arg Gly Gly Ala Gly
210 215 220

Phe Ser Thr Gly Leu Lys Trp Arg Leu Cys Arg Asp Ala Glu Ser Glu
225 230 235 240

Gln Lys Tyr Val Ile Cys Asn Ala Asp Glu Gly Glu Pro Gly Thr Phe
245 250 255

Lys Asp Arg Val Leu Leu Thr Arg Ala Pro Lys Lys Val Phe Val Gly
260 265 270

Met Val Ile Ala Ala Tyr Ala Ile Gly Cys Arg Lys Gly Ile Val Tyr
275 280 285

Leu Arg Gly Glu Tyr Phe Tyr Leu Lys Asp Tyr Leu Glu Arg Gln Leu
290 295 300

Gln Glu Leu Arg Glu Asp Gly Leu Leu Gly Arg Ala Ile Gly Gly Arg
305 310 315 320

Ala Gly Phe Asp Phe Lys Ile Arg Ile Gln Met Gly Ala Gly Ala Tyr
325 330 335

Ile Cys Gly Asp Glu Ser Ala Leu Ile Glu Ser Cys Glu Gly Lys Arg
340 345 350

Gly Thr Pro Arg Val Lys Pro Pro Phe Pro Val Gln Gln Gly Tyr Leu
355 360 365

Gly Lys Pro Thr Ser Val Asn Asn Val Glu Thr Phe Ala Ala Val Ser
370 375 380

Arg Ile Met Glu Glu Gly Ala Asp Trp Phe Arg Ala Met Gly Thr Pro
385 390 395 400

Asp Ser Ala Gly Thr Arg Leu Leu Ser Val Ala Gly Asp Cys Ser Lys
405 410 415

Pro Gly Ile Tyr Glu Val Glu Trp Gly Val Thr Leu Asn Glu Val Leu
420 425 430

Ala Met Val Gly Ala Arg Asp Ala Arg Ala Val Gln Ile Ser Gly Pro
435 440 445

Ser Gly Glu Cys Val Ser Val Ala Lys Asp Gly Glu Arg Lys Leu Ala
450 455 460

Tyr Glu Asp Leu Ser Cys Asn Gly Ala Phe Thr Ile Phe Asn Cys Lys
465 470 475 480

Arg Asp Leu Leu Glu Ile Val Arg Asp His Met Gln Phe Phe Val Glu
485 490 495

Glu Ser Cys Gly Ile Cys Val Pro Cys Arg Ala Gly Asn Val Asp Leu
500 505 510

His Arg Lys Val Glu Trp Val Ile Ala Gly Lys Ala Cys Gln Lys Asp
515 520 525

Leu Asp Asp Met Val Ser Trp Gly Ala Leu Val Arg Arg Thr Ser Arg
530 535 540

Cys Gly Leu Gly Ala Thr Ser Pro Lys Pro Ile Leu Thr Thr Leu Glu
545 550 555 560

Lys Phe Pro Glu Ile Tyr Gln Asn Lys Leu Val Arg His Glu Gly Pro
565 570 575

Leu Leu Pro Ser Phe Asp Leu Asp Thr Ala Leu Gly Gly Tyr Glu Lys
580 585 590

Ala Leu Lys Asp Leu Glu Glu Val Thr Arg

```
        595                 600


<210> SEQ ID NO 55
<211> LENGTH: 602
<212> TYPE: PRT
<213> ORGANISM: Artificial Sequence
<220> FEATURE:
<223> OTHER INFORMATION: Synthetic sequence

<400> SEQUENCE: 55

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asp Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
```

355 360 365

Gly Lys Pro Thr Ser Val Asn Asn Val Glu Thr Phe Ala Ala Val Ser
370 375 380

Arg Ile Met Glu Glu Gly Ala Asp Trp Phe Arg Ala Met Gly Thr Pro
385 390 395 400

Lys Ser Ala Gly Thr Arg Leu Leu Ser Val Ala Gly Asp Cys Ser Lys
405 410 415

Pro Gly Ile Tyr Glu Val Glu Trp Gly Val Thr Leu Asn Glu Val Leu
420 425 430

Ala Met Val Gly Ala Arg Asp Ala Arg Ala Val Gln Ile Ser Gly Pro
435 440 445

Ser Gly Glu Cys Val Ser Val Ala Lys Asp Gly Glu Arg Lys Leu Ala
450 455 460

Tyr Glu Asp Leu Ser Cys Asn Gly Ala Phe Thr Ile Phe Asn Cys Lys
465 470 475 480

Arg Asp Leu Leu Glu Ile Val Arg Asp His Met Gln Phe Phe Val Glu
485 490 495

Glu Ser Cys Gly Ile Cys Val Pro Cys Arg Ala Gly Asn Val Asp Leu
500 505 510

His Arg Lys Val Glu Trp Val Ile Ala Gly Lys Ala Cys Gln Lys Asp
515 520 525

Leu Asp Asp Met Val Ser Trp Gly Ala Leu Val Arg Arg Thr Ser Arg
530 535 540

Cys Gly Leu Gly Ala Thr Ser Pro Lys Pro Ile Leu Thr Thr Leu Glu
545 550 555 560

Lys Phe Pro Glu Ile Tyr Gln Asn Lys Leu Val Arg His Glu Gly Pro
565 570 575

Leu Leu Pro Ser Phe Asp Leu Asp Thr Ala Leu Gly Gly Tyr Glu Lys
580 585 590

Ala Leu Lys Asp Leu Glu Glu Val Thr Arg
595 600

<210> SEQ ID NO 56
<211> LENGTH: 602
<212> TYPE: PRT
<213> ORGANISM: Artificial Sequence
<220> FEATURE:
<223> OTHER INFORMATION: Synthetic sequence

<400> SEQUENCE: 56

Met Asp Ser Arg Ile Thr Thr Ile Leu Glu Arg Tyr Arg Ser Asp Arg
1 5 10 15

Thr Arg Leu Ile Asp Ile Leu Trp Asp Val Gln His Glu Tyr Gly His
20 25 30

Ile Pro Asp Ala Val Leu Pro Gln Leu Gly Ala Gly Leu Lys Leu Ser
35 40 45

Pro Leu Asp Ile Arg Glu Thr Ala Ser Phe Tyr His Phe Phe Leu Asp
50 55 60

Lys Pro Ser Gly Lys Tyr Arg Ile Tyr Leu Cys Asn Ser Val Ile Ala
65 70 75 80

Lys Ile Asn Gly Tyr Gln Ala Val Arg Glu Ala Leu Glu Arg Glu Thr
85 90 95

Gly Ile Arg Phe Gly Glu Thr Asp Pro Asn Gly Met Phe Gly Leu Phe
100 105 110

Asp Thr Pro Cys Ile Gly Leu Ser Asp Gln Glu Pro Ala Met Leu Ile

-continued

```
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asp Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Ser Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540
```

```
Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600


<210> SEQ ID NO 57
<211> LENGTH: 602
<212> TYPE: PRT
<213> ORGANISM: Artificial Sequence
<220> FEATURE:
<223> OTHER INFORMATION: Synthetic sequence

<400> SEQUENCE: 57

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300
```

Gln Glu Leu Arg Glu Asp Gly Leu Leu Gly Arg Ala Ile Gly Gly Arg
305 310 315 320

Ala Gly Phe Asp Phe Asp Ile Arg Ile Gln Met Gly Ala Gly Ala Tyr
325 330 335

Ile Cys Gly Ala Glu Ser Ala Leu Ile Glu Ser Cys Glu Gly Lys Arg
340 345 350

Gly Thr Pro Arg Val Lys Pro Pro Phe Pro Val Gln Gln Gly Tyr Leu
355 360 365

Gly Lys Pro Thr Ser Val Asn Asn Val Glu Thr Phe Ala Ala Val Ser
370 375 380

Arg Ile Met Glu Glu Gly Ala Asp Trp Phe Arg Ala Met Gly Thr Pro
385 390 395 400

Asp Ser Ala Gly Thr Arg Leu Leu Ser Val Ala Gly Asp Cys Ser Lys
405 410 415

Pro Gly Ile Tyr Glu Val Glu Trp Gly Val Thr Leu Asn Glu Val Leu
420 425 430

Ala Met Val Gly Ala Arg Asp Ala Arg Ala Val Gln Ile Ser Gly Pro
435 440 445

Ser Gly Glu Cys Val Ser Val Ala Lys Asp Gly Glu Arg Lys Leu Ala
450 455 460

Tyr Glu Asp Leu Ser Cys Asn Gly Ala Phe Thr Ile Phe Asn Cys Lys
465 470 475 480

Arg Asp Leu Leu Glu Ile Val Arg Asp His Met Gln Phe Phe Val Glu
485 490 495

Glu Ser Cys Gly Ile Cys Val Pro Cys Arg Ala Gly Asn Val Asp Leu
500 505 510

His Arg Lys Val Glu Trp Val Ile Ala Gly Lys Ala Cys Gln Lys Asp
515 520 525

Leu Asp Asp Met Val Ser Trp Gly Ala Leu Val Arg Arg Thr Ser Arg
530 535 540

Cys Gly Leu Gly Ala Thr Ser Pro Lys Pro Ile Leu Thr Thr Leu Glu
545 550 555 560

Lys Phe Pro Glu Ile Tyr Gln Asn Lys Leu Val Arg His Glu Gly Pro
565 570 575

Leu Leu Pro Ser Phe Asp Leu Asp Thr Ala Leu Gly Gly Tyr Glu Lys
580 585 590

Ala Leu Lys Asp Leu Glu Glu Val Thr Arg
595 600

<210> SEQ ID NO 58
<211> LENGTH: 602
<212> TYPE: PRT
<213> ORGANISM: Artificial Sequence
<220> FEATURE:
<223> OTHER INFORMATION: Synthetic sequence

<400> SEQUENCE: 58

Met Asp Ser Arg Ile Thr Thr Ile Leu Glu Arg Tyr Arg Ser Asp Arg
1 5 10 15

Thr Arg Leu Ile Asp Ile Leu Trp Asp Val Gln His Glu Tyr Gly His
20 25 30

Ile Pro Asp Ala Val Leu Pro Gln Leu Gly Ala Gly Leu Lys Leu Ser
35 40 45

Pro Leu Asp Ile Arg Glu Thr Ala Ser Phe Tyr His Phe Phe Leu Asp
50 55 60

```
Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asp Ala Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Asp Leu Ser Cys Asn Gly Ala Phe Thr Ile Phe Asn Cys Lys
465                 470                 475                 480
```

-continued

```
Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600


<210> SEQ ID NO 59
<211> LENGTH: 602
<212> TYPE: PRT
<213> ORGANISM: Artificial Sequence
<220> FEATURE:
<223> OTHER INFORMATION: Synthetic sequence

<400> SEQUENCE: 59

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240
```

```
Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Ala Ala Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Asp Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600
```

<210> SEQ ID NO 60
<211> LENGTH: 602
<212> TYPE: PRT
<213> ORGANISM: Artificial Sequence
<220> FEATURE:
<223> OTHER INFORMATION: Synthetic sequence

<400> SEQUENCE: 60

```
Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Ala Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Lys Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
```

-continued

```
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Asp Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600


<210> SEQ ID NO 61
<211> LENGTH: 602
<212> TYPE: PRT
<213> ORGANISM: Artificial Sequence
<220> FEATURE:
<223> OTHER INFORMATION: Synthetic sequence

<400> SEQUENCE: 61

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
```

```
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Lys Ile Arg Ile Gln Met Gly Ala Gly Ala Tyr
                325                 330                 335

Ile Cys Gly Asp Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Lys Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Asp Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600
```

<210> SEQ ID NO 62
<211> LENGTH: 602
<212> TYPE: PRT
<213> ORGANISM: Artificial Sequence
<220> FEATURE:
<223> OTHER INFORMATION: Synthetic sequence

<400> SEQUENCE: 62

```
Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asp Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365
```

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Lys Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Ser Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600

<210> SEQ ID NO 63
<211> LENGTH: 602
<212> TYPE: PRT
<213> ORGANISM: Artificial Sequence
<220> FEATURE:
<223> OTHER INFORMATION: Synthetic sequence

<400> SEQUENCE: 63

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

-continued

```
Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asn Glu Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Ser Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540
```

```
Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600
```

<210> SEQ ID NO 64
<211> LENGTH: 602
<212> TYPE: PRT
<213> ORGANISM: Artificial Sequence
<220> FEATURE:
<223> OTHER INFORMATION: Synthetic sequence

<400> SEQUENCE: 64

```
Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60

Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300
```

-continued

```
Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asp Ala Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Ser Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600


<210> SEQ ID NO 65
<211> LENGTH: 602
<212> TYPE: PRT
<213> ORGANISM: Artificial Sequence
<220> FEATURE:
<223> OTHER INFORMATION: Synthetic sequence

<400> SEQUENCE: 65

Met Asp Ser Arg Ile Thr Thr Ile Leu Glu Arg Tyr Arg Ser Asp Arg
1               5                   10                  15

Thr Arg Leu Ile Asp Ile Leu Trp Asp Val Gln His Glu Tyr Gly His
            20                  25                  30

Ile Pro Asp Ala Val Leu Pro Gln Leu Gly Ala Gly Leu Lys Leu Ser
        35                  40                  45

Pro Leu Asp Ile Arg Glu Thr Ala Ser Phe Tyr His Phe Phe Leu Asp
    50                  55                  60
```

-continued

```
Lys Pro Ser Gly Lys Tyr Arg Ile Tyr Leu Cys Asn Ser Val Ile Ala
65                  70                  75                  80

Lys Ile Asn Gly Tyr Gln Ala Val Arg Glu Ala Leu Glu Arg Glu Thr
                85                  90                  95

Gly Ile Arg Phe Gly Glu Thr Asp Pro Asn Gly Met Phe Gly Leu Phe
            100                 105                 110

Asp Thr Pro Cys Ile Gly Leu Ser Asp Gln Glu Pro Ala Met Leu Ile
        115                 120                 125

Asp Lys Val Val Phe Thr Arg Leu Arg Pro Gly Lys Ile Thr Asp Ile
    130                 135                 140

Ile Ala Gln Leu Lys Gln Gly Arg Ser Pro Ala Glu Ile Ala Asn Pro
145                 150                 155                 160

Ala Gly Leu Pro Ser Gln Asp Ile Ala Tyr Val Asp Ala Met Val Glu
                165                 170                 175

Ser Asn Val Arg Thr Lys Gly Pro Val Phe Phe Arg Gly Arg Thr Asp
            180                 185                 190

Leu Arg Ser Leu Leu Asp Gln Cys Leu Leu Leu Lys Pro Glu Gln Val
        195                 200                 205

Ile Glu Thr Ile Val Asp Ser Arg Leu Arg Gly Arg Gly Gly Ala Gly
    210                 215                 220

Phe Ser Thr Gly Leu Lys Trp Arg Leu Cys Arg Asp Ala Glu Ser Glu
225                 230                 235                 240

Gln Lys Tyr Val Ile Cys Asn Ala Asp Glu Gly Glu Pro Gly Thr Phe
                245                 250                 255

Lys Asp Arg Val Leu Leu Thr Arg Ala Pro Lys Lys Val Phe Val Gly
            260                 265                 270

Met Val Ile Ala Ala Tyr Ala Ile Gly Cys Arg Lys Gly Ile Val Tyr
        275                 280                 285

Leu Arg Gly Glu Tyr Phe Tyr Leu Lys Asp Tyr Leu Glu Arg Gln Leu
    290                 295                 300

Gln Glu Leu Arg Glu Asp Gly Leu Leu Gly Arg Ala Ile Gly Gly Arg
305                 310                 315                 320

Ala Gly Phe Asp Phe Asp Ile Arg Ile Gln Met Gly Ala Gly Ala Tyr
                325                 330                 335

Ile Cys Gly Asp His Ser Ala Leu Ile Glu Ser Cys Glu Gly Lys Arg
            340                 345                 350

Gly Thr Pro Arg Val Lys Pro Pro Phe Pro Val Gln Gln Gly Tyr Leu
        355                 360                 365

Gly Lys Pro Thr Ser Val Asn Asn Val Glu Thr Phe Ala Ala Val Ser
    370                 375                 380

Arg Ile Met Glu Glu Gly Ala Asp Trp Phe Arg Ala Met Gly Thr Pro
385                 390                 395                 400

Asp Ser Ala Gly Thr Arg Leu Leu Ser Val Ala Gly Asp Cys Ser Lys
                405                 410                 415

Pro Gly Ile Tyr Glu Val Glu Trp Gly Val Thr Leu Asn Glu Val Leu
            420                 425                 430

Ala Met Val Gly Ala Arg Asp Ala Arg Ala Val Gln Ile Ser Gly Pro
        435                 440                 445

Ser Gly Glu Cys Val Ser Val Ala Lys Asp Gly Glu Arg Lys Leu Ala
    450                 455                 460

Tyr Glu Asp Leu Ser Cys Asn Gly Ala Phe Thr Ile Phe Asn Cys Lys
465                 470                 475                 480

Arg Asp Leu Leu Glu Ile Val Arg Asp His Met Gln Phe Phe Val Glu
```

-continued

```
                485                 490                 495

Glu Ser Cys Gly Ile Cys Val Pro Cys Arg Ala Gly Asn Val Asp Leu
            500                 505                 510

His Arg Lys Val Glu Trp Val Ile Ala Gly Lys Ala Cys Gln Lys Asp
        515                 520                 525

Leu Asp Asp Met Val Ser Trp Gly Ala Leu Val Arg Arg Thr Ser Arg
    530                 535                 540

Cys Gly Leu Gly Ala Thr Ser Pro Lys Pro Ile Leu Thr Thr Leu Glu
545                 550                 555                 560

Lys Phe Pro Glu Ile Tyr Gln Asn Lys Leu Val Arg His Glu Gly Pro
                565                 570                 575

Leu Leu Pro Ser Phe Asp Leu Asp Thr Ala Leu Gly Gly Tyr Glu Lys
            580                 585                 590

Ala Leu Lys Asp Leu Glu Glu Val Thr Arg
        595                 600


<210> SEQ ID NO 66
<211> LENGTH: 500
<212> TYPE: PRT
<213> ORGANISM: Rhodobacter capsulatus

<400> SEQUENCE: 66

Met Lys Ile Trp Leu Pro Cys Asp Ala Ala Ala Lys Ala Cys Gly Ala
1               5                   10                  15

Glu Ala Val Leu Ala Ala Leu Arg Leu Glu Ala Glu Lys Arg Gly Gly
            20                  25                  30

Ala Leu Asp Ile Ala Arg Asn Gly Ser Arg Gly Met Ile Trp Leu Glu
        35                  40                  45

Pro Leu Leu Glu Val Glu Thr Pro Ala Gly Arg Ile Gly Phe Gly Pro
    50                  55                  60

Met Thr Pro Ala Asp Val Pro Ala Leu Phe Asp Ala Leu Glu Ser His
65                  70                  75                  80

Pro Lys Ala Leu Gly Leu Val Glu Glu Ile Pro Phe Phe Lys Arg Gln
                85                  90                  95

Thr Arg Leu Thr Phe Ala Arg Cys Gly Arg Ile Glu Pro Leu Ser Leu
            100                 105                 110

Ala Gln Phe Ala Ala Ala Glu Gly Trp Ala Gly Leu Arg Lys Ala Leu
        115                 120                 125

Lys Met Thr Pro Ala Glu Val Val Glu Glu Val Leu Ala Ser Gly Leu
    130                 135                 140

Arg Gly Arg Gly Gly Ala Gly Phe Pro Thr Gly Ile Lys Trp Arg Thr
145                 150                 155                 160

Val Ala Ala Ala Gln Ala Asp Gln Lys Tyr Ile Val Cys Asn Val Asp
                165                 170                 175

Glu Gly Asp Ser Gly Ser Phe Ala Asp Arg Met Leu Ile Glu Gly Asp
            180                 185                 190

Pro Phe Cys Leu Val Glu Gly Met Ala Ile Ala Gly His Ala Val Gly
        195                 200                 205

Ala Thr Arg Gly Tyr Val Tyr Ile Arg Ser Glu Tyr Pro Asp Ala Ile
    210                 215                 220

Ala Val Met Arg Ala Ala Ile Ala Met Ala Lys Pro Phe Leu Ala Glu
225                 230                 235                 240

Ala Gly Phe Glu Met Glu Val Arg Val Gly Ala Gly Ala Tyr Val Cys
                245                 250                 255
```

Gly Glu Glu Thr Ser Leu Leu Asn Ser Leu Glu Gly Lys Arg Gly Thr
260 265 270

Val Arg Ala Lys Pro Pro Leu Pro Ala Leu Lys Gly Leu Phe Gly Lys
275 280 285

Pro Thr Val Val Asn Asn Leu Leu Ser Leu Ala Ala Val Pro Trp Ile
290 295 300

Ile Ala His Gly Ala Lys Ala Tyr Glu Ser Phe Gly Met Asp Arg Ser
305 310 315 320

Arg Gly Thr Ile Pro Leu Gln Ile Gly Gly Asn Val Lys Arg Gly Gly
325 330 335

Leu Phe Glu Thr Gly Phe Gly Ile Thr Leu Gly Glu Leu Val Glu Asp
340 345 350

Ile Cys Gly Gly Thr Ala Ser Gly Arg Pro Val Lys Ala Val Gln Val
355 360 365

Gly Gly Pro Leu Gly Ala Tyr His Pro Val Ser Asp Tyr His Leu Pro
370 375 380

Phe Cys Tyr Glu Gln Phe Ala Gly Gln Gly Gly Leu Val Gly His Ala
385 390 395 400

Gly Leu Val Val His Asp Asp Thr Ala Asp Met Leu Lys Leu Ala Arg
405 410 415

Phe Ala Met Glu Phe Cys Ala Ile Glu Ser Cys Gly Thr Cys Thr Pro
420 425 430

Cys Arg Ile Gly Ala Val Arg Gly Val Glu Val Ile Asp Arg Ile Ala
435 440 445

Ala Gly Asp Ala Ser Ala Met Pro Leu Leu Asp Asp Leu Cys Gln Thr
450 455 460

Met Lys Leu Gly Ser Leu Cys Ala Leu Gly Gly Phe Thr Pro Tyr Pro
465 470 475 480

Val Gln Ser Ala Ile Arg His Phe Pro Ala Asp Phe Pro Cys Ala Arg
485 490 495

Glu Ala Ala Glu
500

<210> SEQ ID NO 67
<211> LENGTH: 150
<212> TYPE: PRT
<213> ORGANISM: Rhodobacter capsulatus

<400> SEQUENCE: 67

Met Thr Asp Thr Ala Arg Leu Arg Ala Ile Leu Ala Ala His Arg Gly
1 5 10 15

Arg Glu Gly Ala Leu Leu Pro Ile Leu His Asp Val Gln Ala Ala Phe
20 25 30

Gly Phe Ile Pro Glu Asp Ala Tyr Ala Pro Ile Ala Ala Asp Leu Gly
35 40 45

Leu Thr Arg Ala Glu Val Ala Gly Val Val Gly Phe Tyr His Asp Phe
50 55 60

Arg Lys Ala Pro Ala Gly Arg His Val Ile Lys Leu Cys Arg Ala Glu
65 70 75 80

Ala Cys Gln Ala Met Gly Met Asp Ala Val Gln Ala Arg Leu Glu Ser
85 90 95

Ala Leu Gly Leu Arg Leu Gly Asp Ser Ser Glu Ala Val Thr Leu Glu
100 105 110

Ala Val Tyr Cys Leu Gly Leu Cys Ala Cys Ala Pro Ala Ala Met Val
115 120 125

Asp Asp Arg Leu Val Gly Arg Leu Asp Ala Ala Ala Val Ala Gly Ile
    130                 135                 140

Val Ala Glu Leu Gly Ala
145                 150

<210> SEQ ID NO 68
<211> LENGTH: 488
<212> TYPE: PRT
<213> ORGANISM: Artificial Sequence
<220> FEATURE:
<223> OTHER INFORMATION: Synthetic sequence

<400> SEQUENCE: 68

Met Ser Arg Lys Leu Val Ile Asp Pro Val Thr Arg Ile Glu Gly His
1               5                   10                  15

Gly Lys Val Val Val His Leu Asp Asp Asp Asn Lys Val Val Asp Ala
            20                  25                  30

Lys Leu His Val Val Glu Phe Arg Gly Phe Glu Lys Phe Val Gln Gly
        35                  40                  45

His Pro Phe Trp Glu Ala Pro Met Phe Leu Gln Arg Ile Cys Gly Ala
    50                  55                  60

Cys Phe Val Ser His His Leu Cys Gly Ala Lys Ala Leu Asp Asp Met
65                  70                  75                  80

Val Gly Val Gly Leu Lys Ser Gly Ile His Val Thr Pro Thr Ala Glu
                85                  90                  95

Lys Met Arg Arg Leu Gly His Tyr Ala Gln Met Leu Gln Ser His Thr
            100                 105                 110

Thr Ala Tyr Phe Tyr Leu Ile Val Pro Glu Met Leu Phe Gly Met Asp
        115                 120                 125

Ala Pro Pro Ala Gln Arg Asn Val Leu Gly Leu Ile Glu Ala Asn Pro
    130                 135                 140

Asp Leu Val Lys Arg Val Val Met Leu Arg Lys Trp Gly Gln Glu Val
145                 150                 155                 160

Ile Lys Ala Val Phe Gly Lys Lys Met His Gly Ile Asn Ser Val Pro
                165                 170                 175

Gly Gly Val Asn Asn Asn Leu Ser Ile Ala Glu Arg Asp Arg Phe Leu
            180                 185                 190

Asn Gly Glu Glu Gly Leu Leu Ser Val Asp Gln Val Ile Asp Tyr Ala
        195                 200                 205

Gln Asp Gly Leu Arg Leu Phe Tyr Asp Phe His Gln Lys His Arg Ala
    210                 215                 220

Gln Val Asp Ser Phe Ala Asp Val Pro Ala Leu Ser Met Cys Leu Val
225                 230                 235                 240

Gly Asp Asp Asp Asn Val Asp Tyr Tyr His Gly Arg Leu Arg Ile Ile
                245                 250                 255

Asp Asp Asp Lys His Ile Val Arg Glu Phe Asp Tyr His Asp Tyr Leu
            260                 265                 270

Asp His Phe Ser Glu Ala Val Glu Glu Trp Ser Tyr Met Lys Phe Pro
        275                 280                 285

Tyr Leu Lys Glu Leu Gly Arg Glu Gln Gly Ser Val Arg Val Gly Pro
    290                 295                 300

Leu Gly Arg Met Asn Val Thr Lys Ser Leu Pro Thr Pro Leu Ala Gln
305                 310                 315                 320

Glu Ala Leu Glu Arg Phe His Ala Tyr Thr Lys Gly Arg Thr Asn Asn
                325                 330                 335

Met Thr Leu His Thr Asn Trp Ala Arg Ala Ile Glu Ile Leu His Ala
340 345 350

Ala Glu Val Val Lys Glu Leu Leu His Asp Pro Asp Leu Gln Lys Asp
355 360 365

Gln Leu Val Leu Thr Pro Pro Pro Asn Ala Trp Thr Gly Glu Gly Val
370 375 380

Gly Val Val Glu Ala Pro Arg Gly Thr Leu Leu His His Tyr Arg Ala
385 390 395 400

Asp Glu Arg Gly Asn Ile Thr Phe Ala Asn Leu Val Val Ala Thr Thr
405 410 415

Gln Asn Asn Gln Val Met Asn Arg Thr Val Arg Ser Val Ala Glu Asp
420 425 430

Tyr Leu Gly Gly His Gly Glu Ile Thr Glu Gly Met Met Asn Ala Ile
435 440 445

Glu Val Gly Ile Arg Ala Tyr Asp Pro Cys Leu Ser Cys Ala Thr His
450 455 460

Ala Leu Gly Gln Met Pro Leu Val Val Ser Val Phe Asp Ala Ala Gly
465 470 475 480

Arg Leu Ile Asp Glu Arg Ala Arg
485

<210> SEQ ID NO 69
<211> LENGTH: 317
<212> TYPE: PRT
<213> ORGANISM: Desulfovibrio vulgaris

<400> SEQUENCE: 69

Met Lys Ile Ser Ile Gly Leu Gly Lys Glu Gly Val Glu Glu Arg Leu
1 5 10 15

Ala Glu Arg Gly Val Ser Arg Arg Asp Phe Leu Lys Phe Cys Thr Ala
20 25 30

Ile Ala Val Thr Met Gly Met Gly Pro Ala Phe Ala Pro Glu Val Ala
35 40 45

Arg Ala Leu Met Gly Pro Arg Arg Pro Ser Val Val Tyr Leu His Asn
50 55 60

Ala Glu Cys Thr Gly Cys Ser Glu Ser Val Leu Arg Ala Phe Glu Pro
65 70 75 80

Tyr Ile Asp Thr Leu Ile Leu Asp Thr Leu Ser Leu Asp Tyr His Glu
85 90 95

Thr Ile Met Ala Ala Ala Gly Asp Ala Ala Glu Ala Ala Leu Glu Gln
100 105 110

Ala Val Asn Ser Pro His Gly Phe Ile Ala Val Val Glu Gly Gly Ile
115 120 125

Pro Thr Ala Ala Asn Gly Ile Tyr Gly Lys Val Ala Asn His Thr Met
130 135 140

Leu Asp Ile Cys Ser Arg Ile Leu Pro Lys Ala Gln Ala Val Ile Ala
145 150 155 160

Tyr Gly Thr Cys Ala Thr Phe Gly Gly Val Gln Ala Ala Lys Pro Asn
165 170 175

Pro Thr Gly Ala Lys Gly Val Asn Asp Ala Leu Lys His Leu Gly Val
180 185 190

Lys Ala Ile Asn Ile Ala Gly Cys Pro Pro Asn Pro Tyr Asn Leu Val
195 200 205

Gly Thr Ile Val Tyr Tyr Leu Lys Asn Lys Ala Ala Pro Glu Leu Asp

-continued

```
    210                 215                 220

Ser Leu Asn Arg Pro Thr Met Phe Phe Gly Gln Thr Val His Glu Gln
225                 230                 235                 240

Cys Pro Arg Leu Pro His Phe Asp Ala Gly Glu Phe Ala Pro Ser Phe
                245                 250                 255

Glu Ser Glu Glu Ala Arg Lys Gly Trp Cys Leu Tyr Glu Leu Gly Cys
            260                 265                 270

Lys Gly Pro Val Thr Met Asn Asn Cys Pro Lys Ile Lys Phe Asn Gln
        275                 280                 285

Thr Asn Trp Pro Val Asp Ala Gly His Pro Cys Ile Gly Cys Ser Glu
    290                 295                 300

Pro Asp Phe Trp Asp Ala Met Thr Pro Phe Tyr Gln Asn
305                 310                 315


<210> SEQ ID NO 70
<211> LENGTH: 567
<212> TYPE: PRT
<213> ORGANISM: Desulfovibrio vulgaris

<400> SEQUENCE: 70

Met Ser Gly Cys Arg Ala Gln Asn Ala Pro Gly Gly Ile Pro Val Thr
1               5                   10                  15

Pro Lys Ser Ser Tyr Ser Gly Pro Ile Val Val Asp Pro Val Thr Arg
            20                  25                  30

Ile Glu Gly His Leu Arg Ile Glu Val Glu Val Glu Asn Gly Lys Val
        35                  40                  45

Lys Asn Ala Tyr Ser Ser Ser Thr Leu Phe Arg Gly Leu Glu Ile Ile
    50                  55                  60

Leu Lys Gly Arg Asp Pro Arg Asp Ala Gln His Phe Thr Gln Arg Thr
65                  70                  75                  80

Cys Gly Val Cys Thr Tyr Thr His Ala Leu Ala Ser Thr Arg Cys Val
                85                  90                  95

Asp Asn Ala Val Gly Val His Ile Pro Lys Asn Ala Thr Tyr Ile Arg
            100                 105                 110

Asn Leu Val Leu Gly Ala Gln Tyr Leu His Asp His Ile Val His Phe
        115                 120                 125

Tyr His Leu His Ala Leu Asp Phe Val Asp Val Thr Ala Ala Leu Lys
    130                 135                 140

Ala Asp Pro Ala Lys Ala Ala Lys Val Ala Ser Ser Ile Ser Pro Arg
145                 150                 155                 160

Lys Thr Thr Ala Ala Asp Leu Lys Ala Val Gln Asp Lys Leu Lys Thr
                165                 170                 175

Phe Val Glu Thr Gly Gln Leu Gly Pro Phe Thr Asn Ala Tyr Phe Leu
            180                 185                 190

Gly Gly His Pro Ala Tyr Tyr Leu Asp Pro Glu Thr Asn Leu Ile Ala
        195                 200                 205

Thr Ala His Tyr Leu Glu Ala Leu Arg Leu Gln Val Lys Ala Ala Arg
    210                 215                 220

Ala Met Ala Val Phe Gly Ala Lys Asn Pro His Thr Gln Phe Thr Val
225                 230                 235                 240

Val Gly Gly Val Thr Cys Tyr Asp Ala Leu Thr Pro Gln Arg Ile Ala
                245                 250                 255

Glu Phe Glu Ala Leu Trp Lys Glu Thr Lys Ala Phe Val Asp Glu Val
            260                 265                 270
```

Tyr Ile Pro Asp Leu Leu Val Val Ala Ala Ala Tyr Lys Asp Trp Thr
275 280 285

Gln Tyr Gly Gly Thr Asp Asn Phe Ile Thr Phe Gly Glu Phe Pro Lys
290 295 300

Asp Glu Tyr Asp Leu Asn Ser Arg Phe Phe Lys Pro Gly Val Val Phe
305 310 315 320

Lys Arg Asp Phe Lys Asn Ile Lys Pro Phe Asp Lys Met Gln Ile Glu
325 330 335

Glu His Val Arg His Ser Trp Tyr Glu Gly Ala Glu Ala Arg His Pro
340 345 350

Trp Lys Gly Gln Thr Gln Pro Lys Tyr Thr Asp Leu His Gly Asp Asp
355 360 365

Arg Tyr Ser Trp Met Lys Ala Pro Arg Tyr Met Gly Glu Pro Met Glu
370 375 380

Thr Gly Pro Leu Ala Gln Val Leu Ile Ala Tyr Ser Gln Gly His Pro
385 390 395 400

Lys Val Lys Ala Val Thr Asp Ala Val Leu Ala Lys Leu Gly Val Gly
405 410 415

Pro Glu Ala Leu Phe Ser Thr Leu Gly Arg Thr Ala Ala Arg Gly Ile
420 425 430

Glu Thr Ala Val Ile Ala Glu Tyr Val Gly Val Met Leu Gln Glu Tyr
435 440 445

Lys Asp Asn Ile Ala Lys Gly Asp Asn Val Ile Cys Ala Pro Trp Glu
450 455 460

Met Pro Lys Gln Ala Glu Gly Val Gly Phe Val Asn Ala Pro Arg Gly
465 470 475 480

Gly Leu Ser His Trp Ile Arg Ile Glu Asp Gly Lys Ile Gly Asn Phe
485 490 495

Gln Leu Val Val Pro Ser Thr Trp Thr Leu Gly Pro Arg Cys Asp Lys
500 505 510

Asn Asn Val Ser Pro Val Glu Ala Ser Leu Ile Gly Thr Pro Val Ala
515 520 525

Asp Ala Lys Arg Pro Val Glu Ile Leu Arg Thr Val His Ser Phe Asp
530 535 540

Pro Cys Ile Ala Cys Gly Val His Val Ile Asp Gly His Thr Asn Glu
545 550 555 560

Val His Lys Phe Arg Ile Leu
565

<210> SEQ ID NO 71
<211> LENGTH: 288
<212> TYPE: PRT
<213> ORGANISM: Desulfovibrio gigas

<400> SEQUENCE: 71

Met Lys Phe Cys Thr Ala Val Ala Val Ala Met Gly Met Gly Pro Ala
1 5 10 15

Phe Ala Pro Lys Val Ala Glu Ala Leu Thr Ala Lys Lys Arg Pro Ser
20 25 30

Val Val Tyr Leu His Asn Ala Glu Cys Thr Gly Cys Ser Glu Ser Leu
35 40 45

Leu Arg Thr Val Asp Pro Tyr Val Asp Glu Leu Ile Leu Asp Val Ile
50 55 60

Ser Met Asp Tyr His Glu Thr Leu Met Ala Gly Ala Gly His Ala Val
65 70 75 80

Glu Glu Ala Leu His Glu Ala Ile Lys Gly Asp Phe Val Cys Val Ile
85 90 95

Glu Gly Gly Ile Pro Met Gly Asp Gly Gly Tyr Trp Gly Lys Val Gly
100 105 110

Arg Arg Asn Met Tyr Asp Ile Cys Ala Glu Val Ala Pro Lys Ala Lys
115 120 125

Ala Val Ile Ala Ile Gly Thr Cys Ala Thr Tyr Gly Gly Val Gln Ala
130 135 140

Ala Lys Pro Asn Pro Thr Gly Thr Val Gly Val Asn Glu Ala Leu Gly
145 150 155 160

Lys Leu Gly Val Lys Ala Ile Asn Ile Ala Gly Cys Pro Pro Asn Pro
165 170 175

Met Asn Phe Val Gly Thr Val Val His Leu Leu Thr Lys Gly Met Pro
180 185 190

Glu Leu Asp Lys Gln Gly Arg Pro Val Met Phe Phe Gly Glu Thr Val
195 200 205

His Asp Asn Cys Pro Arg Leu Lys His Phe Glu Ala Gly Glu Phe Ala
210 215 220

Thr Ser Phe Gly Ser Pro Glu Ala Lys Lys Gly Tyr Cys Leu Tyr Glu
225 230 235 240

Leu Gly Cys Lys Gly Pro Asp Thr Tyr Asn Asn Cys Pro Lys Gln Leu
245 250 255

Phe Asn Gln Val Asn Trp Pro Val Gln Ala Gly His Pro Cys Ile Ala
260 265 270

Cys Ser Glu Pro Asn Phe Trp Asp Leu Tyr Ser Pro Phe Tyr Ser Ala
275 280 285

<210> SEQ ID NO 72
<211> LENGTH: 551
<212> TYPE: PRT
<213> ORGANISM: Desulfovibrio gigas

<400> SEQUENCE: 72

Met Ser Glu Met Gln Gly Asn Lys Ile Val Val Asp Pro Ile Thr Arg
1 5 10 15

Ile Glu Gly His Leu Arg Ile Glu Val Glu Val Glu Gly Gly Lys Ile
20 25 30

Lys Asn Ala Trp Ser Met Ser Thr Leu Phe Arg Gly Leu Glu Met Ile
35 40 45

Leu Lys Gly Arg Asp Pro Arg Asp Ala Gln His Phe Thr Gln Arg Ala
50 55 60

Cys Gly Val Cys Thr Tyr Val His Ala Leu Ala Ser Val Arg Ala Val
65 70 75 80

Asp Asn Cys Val Gly Val Lys Ile Pro Glu Asn Ala Thr Leu Met Arg
85 90 95

Asn Leu Thr Met Gly Ala Gln Tyr Met His Asp His Leu Val His Phe
100 105 110

Tyr His Leu His Ala Leu Asp Trp Val Asn Val Ala Asn Ala Leu Asn
115 120 125

Ala Asp Pro Ala Lys Ala Ala Arg Leu Ala Asn Asp Leu Ser Pro Arg
130 135 140

Lys Thr Thr Thr Glu Ser Leu Lys Ala Val Gln Ala Lys Val Lys Ala
145 150 155 160

Leu Val Glu Ser Gly Gln Leu Gly Ile Phe Thr Asn Ala Tyr Phe Leu

```
                165                 170                 175

Gly Gly His Pro Ala Tyr Val Leu Pro Ala Glu Val Asp Leu Ile Ala
            180                 185                 190

Thr Ala His Tyr Leu Glu Ala Leu Arg Val Gln Val Lys Ala Ala Arg
        195                 200                 205

Ala Met Ala Ile Phe Gly Ala Lys Asn Pro His Thr Gln Phe Thr Val
    210                 215                 220

Val Gly Gly Cys Thr Asn Tyr Asp Ser Leu Arg Pro Glu Arg Ile Ala
225                 230                 235                 240

Glu Phe Arg Lys Leu Tyr Lys Glu Val Arg Glu Phe Ile Glu Gln Val
                245                 250                 255

Tyr Ile Thr Asp Leu Leu Ala Val Ala Gly Phe Tyr Lys Asn Trp Ala
            260                 265                 270

Gly Ile Gly Lys Thr Ser Asn Phe Leu Thr Cys Gly Glu Phe Pro Thr
        275                 280                 285

Asp Glu Tyr Asp Leu Asn Ser Arg Tyr Thr Pro Gln Gly Val Ile Trp
    290                 295                 300

Gly Asn Asp Leu Ser Lys Val Asp Asp Phe Asn Pro Asp Leu Ile Glu
305                 310                 315                 320

Glu His Val Lys Tyr Ser Trp Tyr Glu Gly Ala Asp Ala His His Pro
                325                 330                 335

Tyr Lys Gly Val Thr Lys Pro Lys Trp Thr Glu Phe His Gly Glu Asp
            340                 345                 350

Arg Tyr Ser Trp Met Lys Ala Pro Arg Tyr Lys Gly Glu Ala Phe Glu
        355                 360                 365

Val Gly Pro Leu Ala Ser Val Leu Val Ala Tyr Ala Lys Lys His Glu
    370                 375                 380

Pro Thr Val Lys Ala Val Asp Leu Val Leu Lys Thr Leu Gly Val Gly
385                 390                 395                 400

Pro Glu Ala Leu Phe Ser Thr Leu Gly Arg Thr Ala Ala Arg Gly Ile
                405                 410                 415

Gln Cys Leu Thr Ala Ala Gln Glu Val Glu Val Trp Leu Asp Lys Leu
            420                 425                 430

Glu Ala Asn Val Lys Ala Gly Lys Asp Asp Leu Tyr Thr Asp Trp Gln
        435                 440                 445

Tyr Pro Thr Glu Ser Gln Gly Val Gly Phe Val Asn Ala Pro Arg Gly
    450                 455                 460

Met Leu Ser His Trp Ile Val Gln Arg Gly Gly Lys Ile Glu Asn Phe
465                 470                 475                 480

Gln His Val Val Pro Ser Thr Trp Asn Leu Gly Pro Arg Cys Ala Glu
                485                 490                 495

Arg Lys Leu Ser Ala Val Glu Gln Ala Leu Ile Gly Thr Pro Ile Ala
            500                 505                 510

Asp Pro Lys Arg Pro Val Glu Ile Leu Arg Thr Val His Ser Tyr Asp
        515                 520                 525

Pro Cys Ile Ala Cys Gly Val His Val Ile Asp Pro Glu Ser Asn Gln
    530                 535                 540

Val His Lys Phe Arg Ile Leu
545                 550
```

<210> SEQ ID NO 73
<211> LENGTH: 1809
<212> TYPE: DNA
<213> ORGANISM: Ralstonia eutropha

<400> SEQUENCE: 73
atggatagtc gtatcacgac aatactcgag cgctaccgct cagaccgtac acggctgatc 60
gacatacttt gggatgttca gcatgagtat gggcacattc ccgatgcggt actgccgcaa 120
ctgggggctg ggttgaagct gtccccgctg gacattcgcg aaacggcgtc gttctaccac 180
tttttccttg acaagccgtc gggcaagtat cggatttact tgtgcaattc cgtgattgcc 240
aagatcaacg gctatcaggc ggtgcgtgag gcgctcgaac gcgagactgg gattcgcttc 300
ggcgaaaccg acccgaatgg gatgtttggc ctgttcgaca ccccctgtat cggactcagc 360
gatcaggaac cggcgatgct gatcgataag gtggtattca cccgcctgcg acccggaaag 420
atcacggaca tcatcgcgca gttgaaacaa ggacgatcgc cggccgagat cgcgaacccg 480
gccggtttgc ccagtcagga catcgcctat gtcgatgcca tggtcgagtc caatgtccgc 540
accaaggggc cggtgttctt ccgtggccgg acggatttga gatctttgct cgaccaatgc 600
ctgctgctca agcccgaaca agtgattgag accatcgtcg actccaggct gcgcggacgt 660
ggcggcgcag ggttctcgac cgggctgaag tggcggctgt gtcgggatgc cgaaagcgag 720
cagaagtatg taatctgcaa cgccgacgaa ggtgagcccg gcacgttcaa ggatagggtc 780
ctcctgacac gcgctcccaa gaaggttttc gtcggaatgg ttatcgccgc gtatgcgatc 840
ggctgccgca agggtatcgt ctatctgcgg ggggaatact tctacctcaa ggattatctg 900
gagcgacagc ttcaggaact tcgggaggac gggttgctgg ggcgcgctat cggtggccgg 960
gcgggctttg atttcgatat ccgtattcag atgggggccg gcgcttatat ctgcggcgac 1020
gaatcggcgc tcatcgagtc ctgcgagggg aaacggggca cgccacgggt gaaacctccg 1080
ttcccggtgc agcaagggta tctgggcaag cccaccagcg tcaacaacgt tgagaccttt 1140
gccgccgtgt cgcggatcat ggaggaaggc gcggactggt tccgggcgat gggaacgcca 1200
gactcggccg gcacccggct gctgagcgtg gctggcgatt gcagcaagcc tggcatctac 1260
gaggtggaat ggggggtcac cctcaacgaa gtgctggcga tggtcggagc gcgggacgcg 1320
cgggccgtcc agatcagcgg tccttccggt gaatgcgtgt cggtggcaaa ggacggtgag 1380
cgcaagctcg cgtacgaaga tctttcgtgc aatggcgcct tcaccatttt caactgcaag 1440
cgcgacctgc tggaaatcgt gcgtgaccac atgcagttct tcgtcgaaga gtcctgcggc 1500
atttgtgtgc catgtcgcgc cggcaacgtt gatctgcacc ggaaggtcga atgggtcatc 1560
gcgggcaagg cctgccagaa ggatctggac gatatggtca gttggggagc gctggtgcgg 1620
aggaccagtc gatgtggcct tggggccaca tcgcccaagc ccatcctgac gacgctggag 1680
aaattccccg agatctatca gaacaagctg gtgaggcacg agggcccgct gctgccatcg 1740
ttcgatctcg ataccgcctt gggcgggtat gagaaggcgc tgaaggatct ggaagaggtg 1800
acaagatga 1809

<210> SEQ ID NO 74
<211> LENGTH: 705
<212> TYPE: DNA
<213> ORGANISM: Ralstonia eutropha

<400> SEQUENCE: 74
atgagcattc aaattacgat cgacggcaag acgctcacga ccgaggaagg acgaacgctg 60
gtggatgttg ccgcagagaa cggcgtttac atcccgacgc tgtgctacct caaggacaag 120
ccctgcctcg gcacctgccg ggtgtgttcg gtcaaggtga atggcaatgt cgccgcggca 180

```
tgtacggtgc gggtctcgaa gggcctgaat gtcgaggtca acgaccccga attggtcgac    240

atgcgcaagg cgctggtcga attcctgttc gcggaaggca accacaactg cccgagttgc    300

gagaagagcg gccgttgcca gttgcaggcg gtcggctacg aggtggacat gatggtctcg    360

cgctttccgt accggttccc ggtccgcgtg gtggaccacg cgtccgaaaa gatctggctc    420

gagcgggatc ggtgcatctt ctgtcagcgc tgtgtcgagt tcatccgcga caaggcaagc    480

ggccggaaga tcttcagcat cagccatcgg ggtcccgagt cgcgcatcga gatcgatgcc    540

gaactggcga acgccatgcc gccggagcaa gtcaaagagg cggttgcgat ctgcccggtg    600

ggcaccattc tcgagaaacg ggtcggttat gacgatccca tcggacgacg caagtacgaa    660

atccagtcgg tgcgcgcacg cgcgctggaa ggagaagaca aatga                   705
```

<210> SEQ ID NO 75
<211> LENGTH: 1083
<212> TYPE: DNA
<213> ORGANISM: Ralstonia eutropha

<400> SEQUENCE: 75

```
atggtcgaaa cattttatga agtcatgcgc aggcagggca tttcgcgacg aagtttcctg     60

aagtactgtt ccctgacagc cacatcctta ggactgggac cttcctttct gccgcagatc    120

gcgcacgcga tggaaaccaa gccgcgtaca ccagtacttt ggctgcacgg tctcgaatgt    180

acctgttgct cggaatcgtt cattcgctcg gcccatccgc tggcaaagga cgtcgtgcta    240

tcgatgatct cactggacta tgacgacaca ctgatggcgg ctgccggcca ccaggccgag    300

gccatcctcg aggagatcat gacgaagtac aagggcaact atattctggc ggtggagggg    360

aatccgccac tcaatcagga tggcatgagc tgcatcatcg gtgggcggcc attcattgag    420

cagctcaaat acgtggccaa ggatgccaag gccattatct cctggggttc ctgcgcatcc    480

tggggatgcg tgcaggcagc caaacctaat cccactcagg ccacaccggt tcacaaggtg    540

atcaccgaca agccgattat caaggtcccg gggtgccctc cgattgccga agtgatgacg    600

ggtgtcatta cctacatgct caccttcgat cgtattcccg aactggatcg acagggtcgg    660

ccgaagatgt tctatagcca gcgcatccac gacaaatgct accggcgtcc acacttcgat    720

gccggccagt tcgtcgagga atgggacgac gaatcagccc gcaaaggctt ctgcttatac    780

aagatgggct gtaaaggccc gaccacgtac aacgcctgct ccaccacgcg ctggaacgag    840

gggacgagtt tccccattca gtcgggccac ggttgcattg gttgctccga ggatggcttt    900

tgggacaaag gctcattcta cgatcgtctg accggcatca gccagttcgg cgttgaggcc    960

aacgccgaca agattggcgg aacggcctcc gtcgtggtgg gggcggccgt gacggcgcat   1020

gccgcagcgt ctgcgatcaa gcgtgcgtcg aagaagaacg aaaccagcgg cagtgaacac   1080

taa                                                                1083
```

<210> SEQ ID NO 76
<211> LENGTH: 1857
<212> TYPE: DNA
<213> ORGANISM: Ralstonia eutropha

<400> SEQUENCE: 76

```
atgtcagctt acgcaaccca aggcttcaat cttgacgacc gcggccgtcg cattgtcgtc     60

gatcccgtca cccgcatcga gggtcatatg cgctgcgagg tgaatgtcga tgccaacaat    120

gtcattcgca acgctgtttc cactggtacc atgtggcgcg gactggaagt gattctcaag    180

ggccgcgatc cgcgcgacgc ctgggcgttc gtagaacgca tctgcggtgt ttgtaccggt    240
```

tgtcacgcgc ttgcgtcggt gcgtgccgtg gaaaacgcgc tcgacatcag aattccaaag 300
aacgcccatc tgatccgaga gatcatggcc aagacgttgc aggtgcatga ccatgcggtg 360
catttctatc acctgcatgc gctggattgg gtggatgtca tgtcagccct gaaagccgac 420
ccgaagagga cttccgagtt gcagcagtta gtttcgcctg cgcatccgct gtcctcggca 480
ggctatttcc gcgatattca aaatcgactc aagcgctttg tcgagagtgg tcagcttggc 540
cctttcatga atgggtactg gggatccaag gcttatgtgc tgccgccgga ggccaatctg 600
atggcggtca cgcattattt ggaagcgctg gacctacaga aggagtgggt gaaaatccac 660
accatcttcg gcggcaagaa tccgcacccg aactacttgg tcggtggcgt gccgtgcgcg 720
atcaatctcg atggtatcgg ggctgccagc gcgccggtaa atatggagcg cttgagcttc 780
gttaaggcgc gcatcgacga gatcatcgaa ttcaataaga atgtatacgt gccagacgtg 840
ctcgccatcg gcacactgta taaacaggcc gggtggctgt acggcggcgg gctggcagcc 900
accaacgtgc ttgactacgg cgagtacccg aacgttgcct acaacaagag cactgaccaa 960
ctgcccggcg gcgcgatcct caacggcaac tgggacgaag tatttccagt ggatccgcgc 1020
gactcccaac aggtgcagga attcgtgtcg cacagctggt acaagtatgc cgacgagagc 1080
gtaggtctgc atccctggga cggcgtgact gagcccaatt acgtgctcgg tgcaaacact 1140
aagggtacac gcacgcgcat cgagcaaatc gacgagagcg cgaagtactc gtggattaaa 1200
tcgccgcgct ggcgcggcca cgcgatggag gtagggccgc tgtcgcgcta catccttgcc 1260
tatgcccatg cgcggagcgg caacaagtac gctgagcgtc ccaaggagca gcttgagtac 1320
tccgcgcaga tgatcaacag tgcgatacca aaggcattgg gattgccaga aacacaatac 1380
acgctcaagc agttgttgcc cagcacgatc ggtcgtacgc tggcgcgcgc actcgagagc 1440
caatattgcg gagaaatgat gcatagcgac tggcatgatc tggtcgccaa catccgggcg 1500
ggcgatacgg caaccgccaa cgttgacaag tgggatcctg ccacctggcc gctgcaagcc 1560
aagggcgttg ggaccgtcgc tgcgccgcgc ggcgctctcg gacactggat tcgtatcaag 1620
gacggccgga tcgagaacta tcagtgcgta gtgcctacca cgtggaatgg cagtccgcgt 1680
gattacaagg ggcagatcgg cgcatttgag gcttcgctga tgaacacccc gatggtcaac 1740
ccggagcagc cggtggaaat cttgcgcacg ctgcattcgt tcgatccctg tctggcgtgt 1800
tcgactcacg tcatgagcgc ggaaggccag gaactcacta cagtcaaggt gcgataa 1857

<210> SEQ ID NO 77
<211> LENGTH: 735
<212> TYPE: DNA
<213> ORGANISM: Ralstonia eutropha

<400> SEQUENCE: 77
atgagcacaa aaatgcaggc ggatcgcatt gcagatgcga ccgggaccga cgaaggagcg 60
gtagccagcg ggaagtcaat caaggccact tatgtttatg aggcgccagt gaggctgtgg 120
cactgggtca atgcgctggc gatcgtagtg ctggcagtga ccggattttt tatcggctcg 180
ccgcccgcga ccaggccggg ggaggccagc gcaaactttc tgatgggcta tattcgcttt 240
gcccactttg tcgcagctta catattcgcg atcggcatgc tgggccgcat ctactgggcg 300
acggcaggga atcatcattc ccgcgaactc ttctccgtgc cggtgttcac tcgggcgtac 360
tggcaggagg tgatttcgat gctgcgttgg tacgccttcc tatctgcgcg tccaagccgg 420
tatgtcggtc acaatccgct ggcccgtttc gcgatgttct tcatcttctt cctgagttcg 480

-continued

| | |
|---|---|
| gtgttcatga tcctcacggg cttcgcgatg tacggcgaag gcgcacagat gggctcgtgg | 540 |
| caggagcgca tgttcggctg ggtcattcct ttgctcggtc aatctcagga tgtgcatacc | 600 |
| tggcatcatt tgggtatgtg gttcattgtg gtgtttgtga tcgtccatgt ctatgcagcg | 660 |
| attcgcgagg acatcatggg ccgccagagc gtagtgagca cgatggtctc gggctatcgg | 720 |
| acctttaagg actga | 735 |